United States Patent
Kobayashi et al.

(10) Patent No.: US 8,461,305 B2
(45) Date of Patent: Jun. 11, 2013

(54) L-FUCOSE α1→6 SPECIFIC LECTIN

(75) Inventors: Yuka Kobayashi, Tokyo (JP); Jun Hirabayashi, Tsukuba (JP); Hiroaki Tateno, Tsukuba (JP); Hirokazu Kawagishi, Shizuoka (JP); Hideo Dohra, Shizuoka (JP)

(73) Assignees: J-Oil Mills, Inc., Tokyo (JP); National Institute of Advanced Industrial Science and Technology, Tokyo (JP); National University Corporation Shizuoka University, Shizuoka (JP)

(*) Notice: Subject to any disclaimer, the term of this patent is extended or adjusted under 35 U.S.C. 154(b) by 238 days.

(21) Appl. No.: 13/054,940

(22) PCT Filed: Jul. 15, 2009

(86) PCT No.: PCT/JP2009/003346
§ 371 (c)(1),
(2), (4) Date: Jan. 20, 2011

(87) PCT Pub. No.: WO2010/010674
PCT Pub. Date: Jan. 28, 2010

(65) Prior Publication Data
US 2011/0129938 A1    Jun. 2, 2011

(30) Foreign Application Priority Data
Jul. 22, 2008 (JP) .................... 2008-188390

(51) Int. Cl.
*C07K 16/00* (2006.01)

(52) U.S. Cl.
USPC .................. 530/387.1; 530/387.3; 530/387.5

(58) Field of Classification Search
None
See application file for complete search history.

(56) References Cited

FOREIGN PATENT DOCUMENTS

| JP | H02-083337 | 3/1990 |
|----|------------|--------|
| JP | 2002-112786 | 4/2002 |
| JP | 2007-161633 | 6/2007 |
| WO | 0230954 A1 | 4/2002 |
| WO | 03084569 A1 | 10/2003 |

OTHER PUBLICATIONS

Tashiro et al. (The Third Symposium on Pharmaceutical Food Science Abstracts Oct. 21, 2009 p. 101-103.*
Wimmerova, M., et al., Crystal structure of fungal lectin, J.Biol. Chem., 2003, 278(29), p. 27059-67.
Matsumura, K. et al., Carbohydrate binding specificity of a fucose-specific lectin from *Aspergillus oryzae*: a novel probe for core fucose, J.Biol.Chem., 2007, 282(21), p. 15700-8.
Clynes RA et al., Inhibitory Fc receptors modulate in vivo cytoxicity against tumor targets. Nature Med Apr. 2000; 6 (4): 443-446.
Toyohide Shinkawa et al., The absence of L-fucose but not the presence of galactose or bisecting N-acetyl glucosamine of human IgG1 complex-type oligosaccharides shows the critical role of enhancing antibody-dependent cellular cytotoxicity. J Biol Chem. Jan. 31, 2003; 278(5): 3466-73. Epub Nov. 8, 2002.

\* cited by examiner

*Primary Examiner* — Jacob Cheu

(57) ABSTRACT

Disclosed is a novel lectin which can bind specifically to an L-fucose α1→6 sugar chain. Also disclosed is use of the lectin. The L-fucose α1→6 specific lectin of the present invention is characterized in that: (1) the lectin is extracted from a basidiomycete or an ascomycete; (2) the lectin has a molecular weight by sodium dodecyl sulfate-polyacrylamide gel electrophoresis (SDS-PAGE) of 4,000 to 40,000; and (3) the lectin has an affinity to an L-fucose α1→6 sugar chain, the affinity being represented by an association constant of $1.0 \times 10^4 M^{-1}$ or more (at 25 degrees C.). The lectin can be used for detecting an L-fucose α1→6 sugar chain specifically, and is effective for the purification of an L-fucose α1→6 sugar chain or a non L-fucose α1→6 sugar chain.

16 Claims, 36 Drawing Sheets

Figure 3

Fruiting bodies of *Pholiota terrestris*

↓ extracted with 10mM Tris-HCl buffer

↓ centrifuged

Extraction

↓ Ion-exchange chromatography (DEAE-sepharose)

↓ eluted with 10mM Tris-HCl buffer including 0.1M NaCl

Active fractions

↓ Affinity chromatography (thyroglobulin-agarose)

↓ eluted with 0.2M ammonia

Active fractions

↓ dialyzed

↓ lyophilized

PTL

Figure 7

Fruiting bodies of *Stropharia rugosoannulata*

↓ extracted with PBS

↓ centrifuged

Extraction

↓ precipitated with 80% ammonium

80% ammonium sulfate precipitation fraction

↓ Hydrophobic chromatography (Butyl-TOYOPEARL)

Active fractions

↓ Reversed-phase chromatography (C8)

↓ evaporated

SRL

Figure 29

Fruiting bodies of *Hypholoma sublateritium*

↓ extracted with PBS

↓ centrifuged

Extraction

↓ precipitated with 80% ammonium

80% ammonium sulfate precipitation fraction

↓ Hydrophobic chromatography (Butyl-TOYOPEARL)

Active fractions

↓ Reversed-phase chromatography (C8)

↓ evaporated

NSL

Figure 33

Fruiting bodies of *Lepista sordida*

↓ extracted with PBS

↓ centrifuged

Extraction

↓ precipitated with 80% ammonium

80% ammonium sulfate precipitation fraction

↓ Hydrophobic chromatography (Butyl-TOYOPEARL)

Active fractions

↓ Reversed-phase chromatography (C8)

↓ evaporated

LSL

SEQUENCE LISTING

<160> NUMBER OF SEQ ID NOS: 6

<210> SEQ ID NO 1
<211> LENGTH: 8
<212> TYPE: PRT
<213> ORGANISM: Artificial sequence
<220> FEATURE:
<223> OTHER INFORMATION: common part of sequence No.2 to No.5
<220> FEATURE:
<221> NAME/KEY: MISC_FEATURE
<222> LOCATION: (4)..(4)
<223> OTHER INFORMATION: X stands for Asp/Asn/Glu/Thr.
<220> FEATURE:
<221> NAME/KEY: MISC_FEATURE
<222> LOCATION: (5)..(5)
<223> OTHER INFORMATION: X stands for Thr/Ser/Ala.
<220> FEATURE:
<221> NAME/KEY: MISC_FEATURE
<222> LOCATION: (6)..(6)
<223> OTHER INFORMATION: X stands for Tyr/Phe.
<220> FEATURE:
<221> NAME/KEY: MISC_FEATURE
<222> LOCATION: (7)..(7)
<223> OTHER INFORMATION: X stabds for Gln/Lys/Glu.

<400> SEQUENCE: 1

Cys Asp Gly Xaa Xaa Xaa Xaa Cys
1               5

<210> SEQ ID NO 2
<211> LENGTH: 40
<212> TYPE: PRT
<213> ORGANISM: Pholiota terrestris Overholts
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for Tyr/Ser.
<220> FEATURE:
<221> NAME/KEY: MISC_FEATURE
<222> LOCATION: (23)..(23)
<223> OTHER INFORMATION: X stands for Phe/Tyr.
<220> FEATURE:
<221> NAME/KEY: MISC_FEATURE
<222> LOCATION: (27)..(27)
<223> OTHER INFORMATION: X stands for Arg/Lys/Asn.
<220> FEATURE:
<221> NAME/KEY: MISC_FEATURE
<222> LOCATION: (33)..(33)
<223> OTHER INFORMATION: X stands for Asp/Gly/Ser.
<220> FEATURE:
<221> NAME/KEY: MISC_FEATURE
<222> LOCATION: (35)..(35)
<223> OTHER INFORMATION: X stands for Asn/Ala.
<220> FEATURE:
<221> NAME/KEY: MISC_FEATURE
<222> LOCATION: (39)..(39)
<223> OTHER INFORMATION: X stands for Thr/Gln.

<400> SEQUENCE: 2

Ala Pro Val Pro Val Thr Lys Leu Val Xaa Asp Gly Asp Thr Tyr Lys
1               5                   10                  15

Xaa Thr Ala Xaa Leu Asp Xaa Gly Asp Gly Xaa Trp Val Ala Gln Trp
            20                  25                  30

Xaa Thr Xaa Val Phe His Xaa Gly

-continued

```
<210> SEQ ID NO 3
<211> LENGTH: 39
<212> TYPE: PRT
<213> ORGANISM: Stropharia rugosoannulata Farlow in Murr.
<220> FEATURE:
<221> NAME/KEY: MISC_FEATURE
<222> LOCATION: (4)..(4)
<223> OTHER INFORMATION: X stands for Pro/Gly.
<220> FEATURE:
<221> NAME/KEY: MISC_FEATURE
<222> LOCATION: (7)..(7)
<223> OTHER INFORMATION: X stands for Glu/Lys.
<220> FEATURE:
<221> NAME/KEY: MISC_FEATURE
<222> LOCATION: (9)..(9)
<223> OTHER INFORMATION: X stands for Val/Asp.
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asn/Asp/Glu.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for His/Ser.
<220> FEATURE:
<221> NAME/KEY: MISC_FEATURE
<222> LOCATION: (27)..(27)
<223> OTHER INFORMATION: X stands for Lys/His.
<220> FEATURE:
<221> NAME/KEY: MISC_FEATURE
<222> LOCATION: (29)..(29)
<223> OTHER INFORMATION: X stands for Val/Ile.
<220> FEATURE:
<221> NAME/KEY: MISC_FEATURE
<222> LOCATION: (33)..(33)
<223> OTHER INFORMATION: X stands for Gly/Asn/Ser.
<220> FEATURE:
<221> NAME/KEY: MISC_FEATURE
<222> LOCATION: (34)..(34)
<223> OTHER INFORMATION: X stands for Ala/Thr.
<220> FEATURE:
<221> NAME/KEY: MISC_FEATURE
<222> LOCATION: (39)..(39)
<223> OTHER INFORMATION: X stands for Arg/Thr.

<400> SEQUENCE: 3

Ala Pro Val Xaa Val Thr Xaa Leu Xaa Xaa Asp Gly Xaa Ser Tyr Lys
1               5                   10                  15

Xaa Thr Ala Xaa Leu Asp Tyr Gly Asp Gly Xaa Trp Xaa Ala Gln Trp
            20                  25                  30

Xaa Xaa Asn Val Phe His Xaa
        35

<210> SEQ ID NO 4
<211> LENGTH: 40
<212> TYPE: PRT
<213> ORGANISM: Lepista sordida (Schum. : Fr.) Sing.
<220> FEATURE:
<221> NAME/KEY: MISC_FEATURE
<222> LOCATION: (1)..(1)
<223> OTHER INFORMATION: X stands for Ala/Gln.
<220> FEATURE:
<221> NAME/KEY: MISC_FEATURE
<222> LOCATION: (4)..(4)
<223> OTHER INFORMATION: X stands for Pro/Lys.
```

```
<220> FEATURE:
<221> NAME/KEY: MISC_FEATURE
<222> LOCATION: (7)..(7)
<223> OTHER INFORMATION: X stands for Ala/Ser.
<220> FEATURE:
<221> NAME/KEY: MISC_FEATURE
<222> LOCATION: (8)..(8)
<223> OTHER INFORMATION: X stands for Met/Ile/Val.
<220> FEATURE:
<221> NAME/KEY: MISC_FEATURE
<222> LOCATION: (9)..(9)
<223> OTHER INFORMATION: X stands for Tyr/Thr.
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asp/Asn.
<220> FEATURE:
<221> NAME/KEY: MISC_FEATURE
<222> LOCATION: (16)..(16)
<223> OTHER INFORMATION: X stands for Lys/Glu.
<220> FEATURE:
<221> NAME/KEY: MISC_FEATURE
<222> LOCATION: (17)..(17)
<223> OTHER INFORMATION: X stands for any amino acid, preferably Cys.
<220> FEATURE:
<221> NAME/KEY: MISC_FEATURE
<222> LOCATION: (20)..(20)
<223> OTHER INFORMATION: X stands for Ala/Asn.
<220> FEATURE:
<221> NAME/KEY: MISC_FEATURE
<222> LOCATION: (22)..(22)
<223> OTHER INFORMATION: X stands for Val/Asp/Asn.
<220> FEATURE:
<221> NAME/KEY: MISC_FEATURE
<222> LOCATION: (25)..(25)
<223> OTHER INFORMATION: X stands for Asp/Asn.
<220> FEATURE:
<221> NAME/KEY: MISC_FEATURE
<222> LOCATION: (27)..(27)
<223> OTHER INFORMATION: X stands for Arg/His/Asn.
<220> FEATURE:
<221> NAME/KEY: MISC_FEATURE
<222> LOCATION: (31)..(31)
<223> OTHER INFORMATION: X stands for Gln/Arg.
<220> FEATURE:
<221> NAME/KEY: MISC_FEATURE
<222> LOCATION: (34)..(34)
<223> OTHER INFORMATION: X stands for Thr/Val.

<400> SEQUENCE: 4

Xaa Pro Val Xaa Val Lys Xaa Xaa Xaa Xaa Asp Gly Xaa Thr Tyr Xaa
1               5                   10                  15

Xaa Thr Ala Xaa Leu Xaa Tyr Gly Xaa Gly Xaa Trp Val Ala Xaa Trp
            20                  25                  30

Ser Xaa Ala Val Phe His Gln Ser
        35                  40

<210> SEQ ID NO 5
<211> LENGTH: 39
<212> TYPE: PRT
<213> ORGANISM: Naematoloma sublateritium (Fr.) Karst/Hypholoma
      sublateritium(Fr.)Quel
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (13)..(13)
<223> OTHER INFORMATION: X stands for Asp/Thr.
<220> FEATURE:
<221> NAME/KEY: MISC_FEATURE
```

```
<222> LOCATION: (14)..(14)
<223> OTHER INFORMATION: X stands for Ser/Ala.
<220> FEATURE:
<221> NAME/KEY: MISC_FEATURE
<222> LOCATION: (16)..(16)
<223> OTHER INFORMATION: X stands for Gln/Lys.
<220> FEATURE:
<221> NAME/KEY: MISC_FEATURE
<222> LOCATION: (17)..(17)
<223> OTHER INFORMATION: X stands for any amino acid, preferably Cys.

<400> SEQUENCE: 5

Ala Pro Val Pro Val Thr Lys Leu Val Xaa Asp Gly Xaa Xaa Phe Xaa
1               5                   10                  15

Xaa Thr Ala Asn Leu Asp Phe Gly Asp Gly Asn Trp Val Ala Gln Trp
            20                  25                  30

Ser Thr Asn Val Phe His Asn
        35

<210> SEQ ID NO 6
<211> LENGTH: 40
<212> TYPE: PRT
<213> ORGANISM: Naematoloma sublateritium (Fr.) Karst/Hypholoma
      sublateritium(Fr.)Quel
<220> FEATURE:
<221> NAME/KEY: MISC_FEATURE
<222> LOCATION: (10)..(10)
<223> OTHER INFORMATION: X stands for any amino acid, preferably Cys.
<220> FEATURE:
<221> NAME/KEY: MISC_FEATURE
<222> LOCATION: (14)..(14)
<223> OTHER INFORMATION: X stands for Asp/Thr.
<220> FEATURE:
<221> NAME/KEY: MISC_FEATURE
<222> LOCATION: (15)..(15)
<223> OTHER INFORMATION: X stands for Ser/Ala.
<220> FEATURE:
<221> NAME/KEY: MISC_FEATURE
<222> LOCATION: (17)..(17)
<223> OTHER INFORMATION: X stands for Gln/Lys.
<220> FEATURE:
<221> NAME/KEY: MISC_FEATURE
<222> LOCATION: (18)..(18)
<223> OTHER INFORMATION: X stands for any amino acid, preferably Cys.

<400> SEQUENCE: 6

Ala Pro Val Pro Val Thr Lys Leu Val Xaa Asp Asp Gly Xaa Xaa Phe
1               5                   10                  15

Xaa Xaa Thr Ala Asn Leu Asp Phe Gly Asp Gly Asn Trp Val Ala Gln
            20                  25                  30

Trp Ser Thr Asn Val Phe His Asn
        35                  40
```

L-FUCOSE α1→6 SPECIFIC LECTIN

TECHNICAL FIELD

The present invention relates to a novel L-fucose α1→6 specific lectin, the manufacture method thereof, and the application thereof. In particular, the present invention relates to a novel lectin derived from basidiomycete or ascomycete, the manufacture method thereof, and a method of detection and fractionation of a sugar chain using the lectin.

BACKGROUND ART

It has been known that the gene of an α1→6 fucosyltransferase (FUT8), which transfers an L-fucose residue to the reducing terminal N-acetylglucosamine of the N-linked glycan via an α1→6-linkage to form core fucosylation, expresses in accordance with the canceration of hepatocytes. The hepatocellular carcinoma is currently detected by lectin affinity electrophoresis using *Lens culinaris* agglutinin (LCA) having an affinity to core-fucosylated mono- and bi-antennary N-glycans.

Antibody-dependent cellular cytotoxicity (hereinafter referred to as an ADCC activity) is one of the immune functions owned by humans. The ADCC activity is an activity through which leukocytes such as natural killer cells and monocytes kill target cells such as cancer cells via antibodies. The ADCC activity has a relation with the antitumor mechanism by the antibody medical drug such as Herceptin as a humanized antibody (a therapeutic agent for metastatic breast cancer) and Rituxan as a chimeric antibody (a therapeutic agent for non-Hodgkin's lymphoma) (Non-patent Publication 1) against tumors. When these antibody medical drugs have a low ADCC activity, the need is caused to administer a high amount of the antibody medical drug, which consequently causes problems such as an increased cost and a side effect (e.g., infection due to an immune compromise).

The ADCC activity is different by a difference of 50 to 100 times between an antibody to which α1→6 L-fucose is transferred and an antibody to which α1→6 L-fucose is not transferred (Non-patent Publication 2). If an antibody to which α1→6 L-fucose is not transferred can be obtained, the antibody preparation having a high ADCC activity can be provided.

Conventionally, in addition to LCA, other core fucose-binding lectins have been known such as *Pisum sativum* agglutinin (PSA), *Aleuria aurantia* lectin (AAL), *Narcissus pseudonarcissus* agglutinin (NPA), *Vicia faba* agglutinin (VFA), and *Aspergillus oryzae* lectin (AOL) for example (Patent Publications 1 to 5).

Non-patent Publication 1: Clynes R A et al., Inhibitory Fc receptors modulate in vivo cytoxicity against tumor targets. NATURE MED 2000 APR; 6(4): 443-446

Non-patent Publication 2: Toyohide Shinkawa et al., The absence of L-fucose but not the presence of galactose or bisecting N-acetyl glucosamine of human IgG1 complex-type oligosaccharides shows the critical role of enhancing antibody-dependent cellular cytotoxicity. J Biol. Chem. 2003 Jan. 31; 278(5): 3466-73. Epub 2002 Nov. 8.

Patent Publication 1: WO2002/030954

Patent Publication 2: WO2003/084569

Patent Publication 3: Example of Japanese Unexamined Patent Application Publication No. H02-083337

Patent Publication 4: Example 5 of Japanese Unexamined Patent Application Publication No. 2002-112786

Patent Publication 5: Japanese Unexamined Patent Application Publication No. 2007-161633

DISCLOSURE OF THE INVENTION

Known lectins used for the detection of an L-fucose α1→6 sugar chain also have an affinity to not only the L-fucose α1→6 linkage sugar chain but also a glycolipid sugar chain having L-fucose other than α1→6 linkage and a high mannose sugar chain not having L-fucose. Specifically, AAL and AOL also have an affinity to α1→2 L-fucose and α1→3 L-fucose for example. Mannose-specific LCA, PSA, and VFA also have an affinity to non-fucosylated mono- and di-antennary N-glycans. Thus, it has not been able to accurate detection of an L-fucose α1→6 sugar chain and also it has not been able to isolate an L-fucose α1→6 sugar chain. No lectin has been known that can bind specifically only to an L-fucose α1→6 sugar chain.

In view of the above, it is an objective of the present invention to provide a novel lectin that can bind specifically to an L-fucose α1→6 sugar chain. This invention can provide a more accurate method for the detection of an L-fucose α1→6 sugar chain using the novel lectin than in a conventional case, and a method of the fractionation of an L-fucose α1→6 sugar chain and a non-L-fucose α1→6 sugar chain based on the detection of an L-fucose α1→6 sugar chain.

The present inventors have found a novel lectin that has a very high affinity to a sugar chain having L-fucose α1→6. The present inventors have found that the novel lectin can specifically detect an L-fucose α1→6 sugar chain and that this lectin can be used for the purification of an L-fucose α1→6 sugar chain or a non L-fucose α1→6 sugar chain (L-fucose α1→2, 1→3, 1→4 sugar chain). The term "L-fucose α1→6 sugar chain" means a structure in which L-fucose is bonded to the reducing terminal N-acetylglucosamine of an N-linked glycan by a α1→6 bond. The term "non-L-fucose α1→6 sugar chain" means a sugar chain that does not have an α1→6 bond L-fucose in molecules.

Specifically, the present invention provides an L-fucose α1→6 specific lectin that: (1) is extracted from basidiomycete or ascomycete, (2) has a molecular weight by sodium dodecyl sulfate-polyacrylamide gel electrophoresis (SDS-PAGE) of 4,000 to 40,000, and (3) has an affinity to an L-fucose α1→6 sugar chain represented by a association constant of $1.0 \times 10^4 M^{-1}$ or more (at 25 degrees C.). The association constant herein means a numeric value that is measured by frontal affinity chromatography (FAC) at an analysis temperature of 25 degrees C.

The L-fucose α1→6 sugar chain may include a sialo N-glycans.

Furthermore, the L-fucose α1→6 specific lectin (4) is preferably substantially not bound to high mannose sugar chains and/or glycolipids not including L-fucose α1→6 sugar chain.

Furthermore, the L-fucose α1→6 specific lectin preferably (5) has an affinity to α1→6 fucosylated, mono-, di-, tri-, and tetra-antennary N-glycans with the association constant of $1.0 \times 10^4 M^{-1}$ or more (at 25 degrees C.).

The basidiomycete belongs, for example, to Strophariaceae, Tricholomataceae, Amanitaceae, or Polyporaceae.

The basidiomycete is, for example, *Pholiota terrestris, Pholiota squarrosa, Pholiota adiposa, Stropharia rugosoannulata, Naematoloma sublateritium, Lepista sordid*, or *Amanita muscaria*.

In particular, the amino acid sequence of the L-fucose α1→6 specific lectin (6) is shown in the sequence number 1.

The present invention also provides the L-fucose α1→6 specific lectin that is (a) protein or peptide consisting of an amino acid sequence shown in any of sequence numbers 2 to 5 or (b) protein or peptide in which one or plurality of amino acid(s) is/are deleted, inserted, or substituted in the amino acid sequence shown in any of sequence numbers 2 to 5 and which is functionally-equivalent to protein or peptide having the amino acid sequence shown in any of sequence numbers 2 to 5. The wording "functionally-equivalent" means an affinity to an L-fucose α1→6 sugar chain represented by an association constant of $1.0×10^4 M^{-1}$ or more (at 25 degrees C.).

The protein or peptide shown in (b) has an amino acid sequence shown by a sequence number 6 for example.

The present invention also provides an L-fucose α1→6 specific lectin that is protein or peptide having at least 37% or more homology to an amino acid sequence shown in any of sequence numbers 2 to 6 and being functionally-equivalent to protein or peptide having the amino acid sequence shown in any of sequence numbers 2 to 6.

The present invention also provides a method of manufacturing an L-fucose α1→6 specific lectin by which an aqueous medium extract (water-soluble extract) of basidiomycete and/or ascomycete is applied to (i) hydrophobic chromatography and reversed-phase chromatography, (ii) affinity chromatography, or (iii) ion-exchange chromatography and gel filtration to thereby obtain a lectin that (vi) has a molecular weight by sodium dodecyl sulfate-polyacrylamide gel electrophoresis (SDS-PAGE) of 4,000 to 40,000, and that (v) has an affinity represented with an association constant to an L-fucose α1→6 sugar chain of $1.0×10^4 M^{-1}$ or more (at 25 degrees C.).

The basidiomycete is preferably selected from at least one of Strophariaceae, Tricholomataceae, Amanitaceae and Polyporaceae.

The basidiomycete is preferably at least one selected from *Pholiota terrestris, Pholiota squarrosa, Pholiota adiposa, Stropharia rugosoannulata, Naematoloma sublateritium, Lepista sordida*, and *Amanita muscaria*.

Basidiomycete and/or ascomycete used in the method of manufacturing an L-fucose α1→6 specific lectin is preferably carpophores (fruiting bodies).

The present invention also provides a method of detecting an L-fucose α1→6 sugar chain including a process of causing a sugar chain to act on the L-fucose α1→6 specific lectin.

The sugar chain is a tumor marker for example.

The present invention also provides a method of fractionating a L-fucose α1→6 sugar chain including a process of causing a sugar chain to act on the L-fucose α1→6 specific lectin. Specifically, the invention provides a method of fractionating an L-fucose α1→6 sugar chain and a non-L-fucose α1→6 sugar chain by using immobilized the L-fucose α1→6 specific lectin.

The sugar chain acting in the fractionation method is bound to an antibody for example.

The present invention also provides a diagnostic agent and a diagnostic agent kit for detecting an L-fucose α1→6 sugar chain. The diagnostic agent includes the L-fucose α1→6 specific lectin as an active ingredient.

The novel lectin of the present invention has a much higher affinity than the conventional one with an association constant of $1.0×10^4 M^{-1}$ or more to a sugar chain, glycopeptides, and glycoprotein having an L-fucose α1→6. Specifically, only a sugar chain having an L-fucose α1→6 sugar chain structure can be recognized specifically. Using this specificity, the L-fucose α1→6 specific lectin can be used in various applications as shown below.

In contrast with a conventional lectin having an affinity to an L-fucose α1→6 sugar chain, the present invention can detect an α1→6 L-fucose sugar chain in a more selective specificity.

The method of fractionating an L-fucose α1→6 sugar chain of the present invention can provide, based on an accurate identification of α1→6 L-fucose, a stricter fractionation between an L-fucose α1→6 sugar chain and a non-L-fucose α1→6 sugar chain. As a result, an L-fucose α1→6 sugar chain or a non-L-fucose α1→6 sugar chain can be purified at a high purity. In particular, by using the fractionation method of the present invention to remove an L-fucose α1→6 sugar chain from the antibody preparation consisting of a mixture of an L-fucose α1→6 sugar chain and a non-L-fucose α1→6 sugar chain, the antibody medical drug can have an increased ADCC activity. As a result, the antibody preparation can be formulated in a reduced dosage, thus advantageously realizing a reduced cost and reduced side effects for example. Furthermore, the antibody preparation also can be prescribed in accordance with a symptom or a side effect.

BRIEF DESCRIPTION OF THE DRAWINGS

FIG. 3 illustrates the purification process of PTL in Example 1.

FIG. 7 illustrates the purification process of SRL of Example 2.

FIG. 29 illustrates the purification process of NSL of Example 3.

FIG. 33 illustrates the purification process of LSL of Example 4.

BEST MODE FOR CARRYING OUT THE INVENTION

Figure 1:
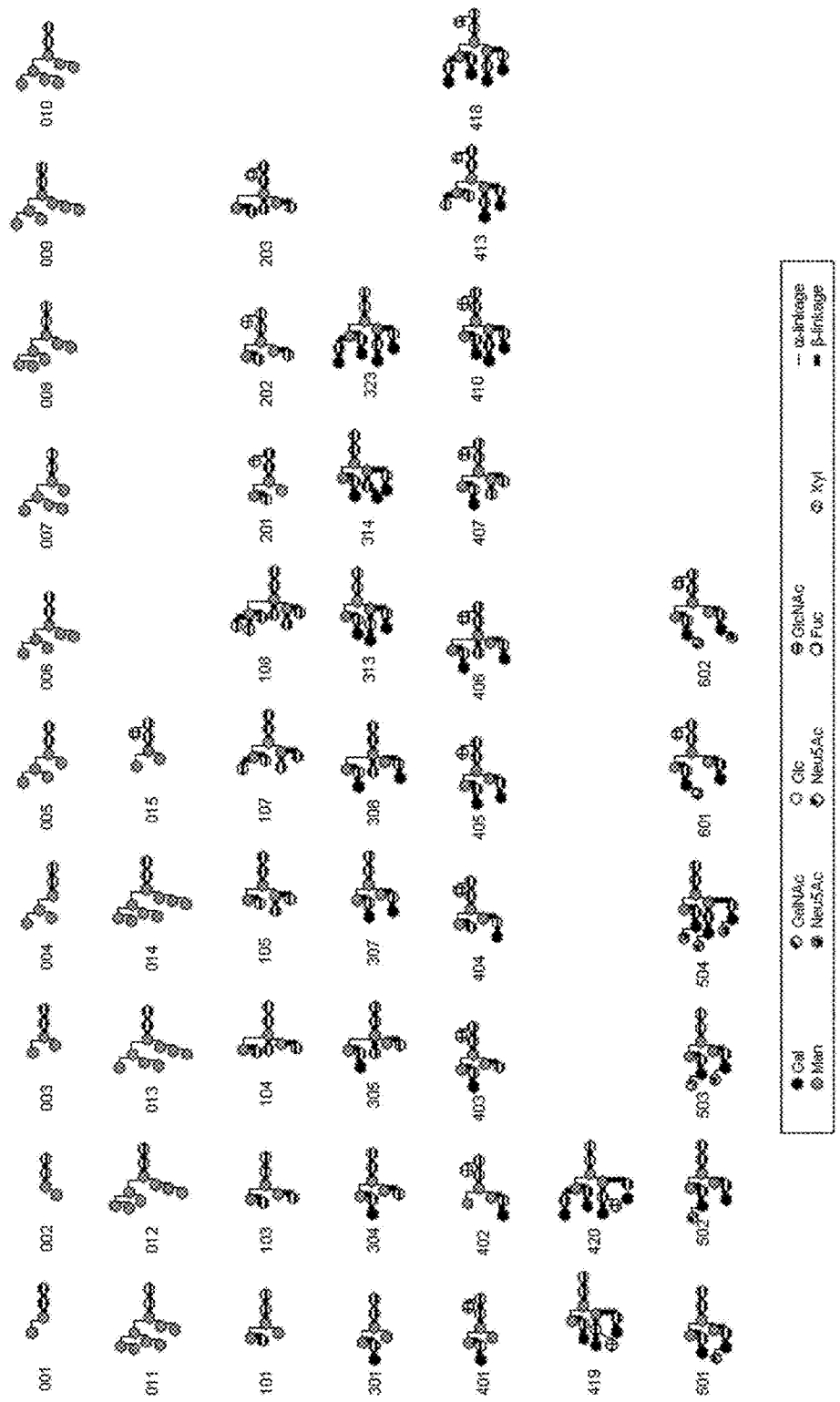
FIG. 1 is a structural diagram of an α1→6 L-fucose oligosaccharide and a non-α1→6 L-fucose oligosaccharide used in a working example and a comparison example of the present invention.

The following section will show an example of an L-fucose α1→6 sugar chain to which the L-fucose α1→6 specific lectin is bound.

[Chemical formula 1]

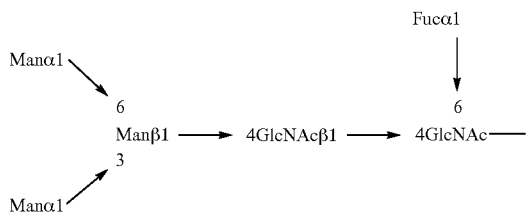

[In the formula, Man means mannose, GlcNAc means N-acetylglucosamine, and Fuc means L-fucose.]

In addition to the above one, L-fucose α1→6 sugar chains include free oligosaccharide, glycoamino acid, glycopeptide, glycolipid, glycoprotein, proteoglycan, and cells for example. Furthermore, L-fucose α1→6 sugar chains also may fluorescently-labeled by CyDye, 4-ethyl aminobenzoate (ABEE), and amino pyridine for example. An N-linked sugar chain includes high mannose-type one, complex-type one, and hybrid-type one for example. Furthermore, an N-linked sugar chain also may be the one obtained by partially decomposing the sugar chain chemically by acid or hydrazine for example or the one for which any enzyme of sialidase, galactosidase, N-acetylhexosaminidase, fucosidase, and mannosidase is used simultaneously or in a stepwise method to partially decompose the sugar chain. Alternatively, an N-linked sugar chain also may be the one obtained by adding sugar such as glucose or a functional group such as acetyl group, a sulfate group, or phosphate group for example to the sugar chain.

(1) Basidiomycete or ascomycete from which the L-fucose α1→6 specific lectin is derived belongs, for example, to Strophariaceae, Tricholomataceae, Polyporaceae, and Amanitaceae. Strophariaceae includes *Pholiota terrestris, Stropharia rugosoannulata, Naematoloma sublateritium, Pholiota squarrosa, Pholiota adiposa*, and *Pholiota adiposa* for example. Tricholomataceae includes *Lepista sordida* for example. Polyporaceae includes *Trichaptum elongatum* and *Microporus affinis* for example. Amanitaceae includes *Amanita muscaria* for example. Among these basidiomycetes or ascomycetes, from the viewpoints of a lectin recovery efficiency and sugar-binding specificity, Strophariaceae, Tricholomataceae, or Amanitaceae is particularly preferred. Further preferred basidiomycetes or ascomycetes are *Pholiota terrestris, Pholiota squarrosa, Pholiota adiposa, Stropharia rugosoannulata, Naematoloma sublateritium, Lepista sordid*, or *Amanita muscaria*.

The L-fucose α1→6 specific lectin has (2) a molecular weight on SDS-PAGE of 4,000 to 40,000 and preferably of 4,000 to 20,000. The molecular weight by SDS-PAGE is measured by the Laemmi method for example (Nature, volume 227, page 680, 1976).

The L-fucose α1→6 specific lectin has (3) an association constant (Ka) to the L-fucose α1→6 sugar chain of $1.0 \times 10^4 M^{-1}$ or more, preferably $1.0 \times 10^5 M^{-1}$ or more, and more preferably $1.0 \times 10^6 M^{-1}$ or more. Specifically, when the L-fucose α1→6 specific lectin is compared with AAL, AOL, LCA, NPA, and PSA conventionally known as having an affinity to L-fucose α1→6, the L-fucose α1→6 specific lectin has a remarkably-high association constant. This means that the L-fucose α1→6 specific lectin is bound to an L-fucose α1→6 sugar chain with a much higher selectivity than in the conventional lectin.

The L-fucose α1→6 sugar chain may have a sialic acid at the nonreducing terminal thereof. A conventional core fucose specific lectin (e.g., LCA, NPA, and PSA) has a low affinity to an L-fucose α1→6 sugar chain having a sialic acid at the nonreducing terminal. On the other hand, the L-fucose α1→6 specific lectin is superior to the conventional one in having a high affinity also to the sugar chain as described above.

The following section will describe a method of calculating an association constant by frontal affinity chromatography (FAC). This method is based on the following principle. When diluent of a fixed concentration of a fluorescently-labeled sugar chain (e.g., the one shown in FIGS. 1 and 2) is caused to flow in a column in which lectin is immobilized, the sugar chain flows out of the column in a short time when the lectin and the sugar chain do not have an interaction therebetween. Then, the elution front end (front) is observed immediately. When there is an affinity with lectin, the elution of the sugar chain is delayed.

The preparation of a lectin column used in the apparatus is performed in the method as described below. 1. Purified lectin is dissolved in 0.1 to 0.2M of NaHCO$_3$ buffer solution (pH 8.3 to 8.5). 2. The lectin is immobilized, via a lectin primary amino group, a carrier such as NHS activated sepharose. 3. Then, the lectin is blocked by Tris buffer solution including primary amine or ethanolamine for example. 4. Lectin-sepharose is suspended in 10 mM Tris buffer, including 0.8% of NaCl (pH 7.4, TBS). Then, lectin immobilized resin is filled in a miniature column (φ2 mm×10 mm, 31.4 μl). 5. The miniature column in which the lectin immobilized resin is filled is protected by a holder and the lectin column is connected to an FAC automatic analysis apparatus (FAC-1, SHIMADZU CORPORATION).

To the equilibrated lectin column, pyridylaminated sugar chain (PA sugar chain) diluted by an analysis buffer solution (10 mM of Tris buffer including 0.8% of NaCl (pH 7.4, TBS)) to have a concentration (2.5 nM) sufficiently lower than the dissociation constant ($K_d$) of lectin is poured in an amount of 300 μl at a flow rate of 0.125 ml/min. Then, the elution of the PA sugar chain from the column is detected by a fluorescence detector (excitation wavelength/fluorescence wavelength: 310 nm/380 nm).

Based on the detection data, by using the elution front end ($V_o$) of the sugar chain (PA rhamnose) not interacting with lectin as a reference, the delay ($V-V_o$) of the elution front end (V) of a sugar chain interacting with lectin is calculated as an interaction strength. Then, based on the following FAC criteria expressions, the association constant ($K_a$) between the sugar chain and lectin is calculated based on $V-V_o$ and $B_t$. If the interaction strength ($V-V_o$ value) and the association constant are higher, a higher affinity is caused between lectin and an L-fucose α1→6 sugar chain.

[Formula 1]

$$K_a = \frac{[A][B]}{[AB]} = \frac{B_t}{V-V_0} - [A]_0 \quad (1)$$

$$\frac{1}{[A]_0(V-V_0)} = \frac{K_d}{B_t} \cdot \frac{1}{[A]_0} + \frac{1}{B_t} \quad (2)$$

$$K_d = \frac{[A][B]}{[AB]} = \frac{B_t}{V-V_0} \quad (3)$$

[In the formula, A means substance used for the elution, $A_o$ means the initial concentration of the substance A, B means a immobilized ligand, V means the elution volume, $V_o$ means the elution front end volume of the substance not interacting with the immobilized ligand B at all, $B_t$ means an effective ligand amount, $K_d$ means a dissociation constant (an inverse of the association constant)].

The sugar binding specificity of lectin also can be confirmed by using erythrocytes that can be specifically agglutinated by the lectin to investigate the sugar type that may inhibit the agglutination of the erythrocytes and the concentration thereof.

Furthermore, the L-fucose α1→6 specific lectin is (4) preferably substantially not bound to a high mannose sugar chain and/or glycolipid, not including an L-fucose α1→6 sugar chain. Thus, the L-fucose α1→6 specific lectin has a higher binding specificity. The wording "substantially not bound" herein means a association constant of $1.0 \times 10^3 M^{-1}$ or lower and preferably a association constant of $1.0 \times 10^2 M^{-1}$ or lower, and particularly preferably an association constant of 0.

Furthermore, the L-fucose α1→6 specific lectin (5) preferably has an affinity to α1→6 fucosylated, mono-, di-, tri-, tetra-antennary N-glycans. The affinity is represented by an association constant of $1.0 \times 10^4 M^{-1}$ or more (at 25 degrees C.) and more preferably is represented by an association constant of $1.0 \times 10^5 M^{-1}$ or more.

Examples of the structures of α1→6 fucosylated, mono-, di-, tri-, tetra-antennary N-glycans having an affinity to the lectin of the present invention are shown below.

[Chemical formula 2]

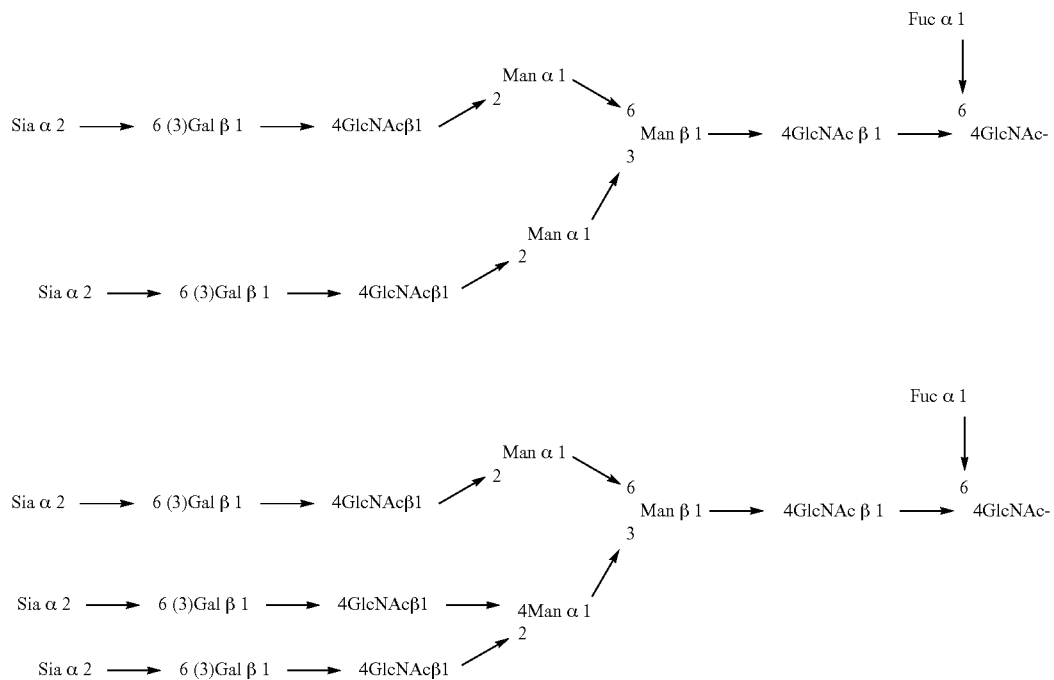

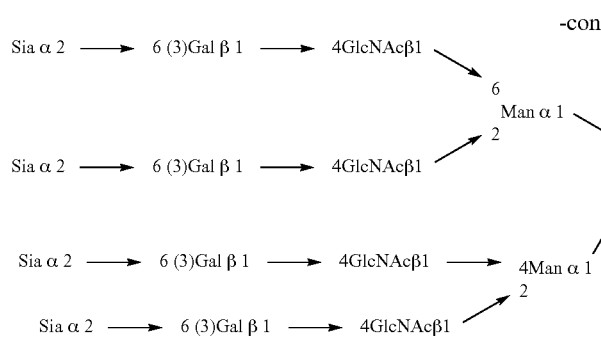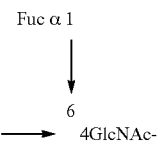

The L-fucose α1→6 specific lectin of the present invention has a common amino acid sequence in particular as shown by the sequence number 1. The 4<sup>th</sup>, 5<sup>th</sup>, 6<sup>th</sup>, and 7<sup>th</sup> Xaas in the sequence number 1 mean Asp/Asn/Glu/Thr, Thr/Ser/Ala, Tyr/Phe, and Gln/Lys/Glu, respectively among which the diagonal lines mean "or".

A specific example of the L-fucose α1→6 specific lectin of the present invention is protein or peptide shown by the sequence numbers 1 to 6.

The lectin shown by the sequence number 2 is a novel lectin that can be extracted from *Pholiota terrestris* (hereinafter referred to as PTL). The 10<sup>th</sup> and 17<sup>th</sup> Xaas of the sequence number 2 may be any amino acid residue but are preferably Cys. The 20<sup>th</sup>, 23<sup>rd</sup>, 27<sup>th</sup>, 33<sup>rd</sup>, 35<sup>th</sup>, and 39<sup>th</sup> Xaas are Tyr/Ser, Phe/Tyr, Arg/Lys/Asn, Asp/Gly/Ser, Asn/Ala, and Thr/Gln, respectively.

The lectin shown by the sequence number 3 is a novel lectin that can be extracted from *Stropharia rugosoannulata* (hereinafter referred to as SRL). The 10<sup>th</sup> and 17<sup>th</sup> Xaas of the sequence number 3 may be any amino acid residue but are preferably Cys. The 4<sup>th</sup>, 7<sup>th</sup>, 9<sup>th</sup>, 13<sup>th</sup>, 20<sup>th</sup>, 27<sup>th</sup>, 29<sup>th</sup>, 33<sup>rd</sup>, 34<sup>th</sup>, and 39<sup>th</sup> Xaas are Pro/Gly, Glu/Lys, Val/Asp, Asn/Asp/Glu, His/Ser, Lys/His, Val/Ile, Gly/Asn/Ser, Ala/Thr, and Arg/Thr, respectively.

The lectin shown by the sequence number 4 is a novel lectin that can be extracted from *Lepista sordida* (hereinafter referred to as LSL). The 10<sup>th</sup> and 17<sup>th</sup> Xaas of the sequence number 4 may be any amino acid residue but are preferably Cys. The 1<sup>st</sup>, 4<sup>th</sup>, 7<sup>th</sup>, 8<sup>th</sup>, 9<sup>th</sup>, 13<sup>th</sup>, 16<sup>th</sup>, 20<sup>th</sup>, 22<sup>nd</sup>, 25<sup>th</sup>, 27<sup>th</sup>, 31<sup>st</sup>, and 34<sup>th</sup> Xaas are Ala/Gln, Pro/Lys, Ala/Ser, Met/Ile/Val, Tyr/Thr, Asp/Asn, Lys/Glu, Ala/Asn, Val/Asp/Asn, Asp/Asn, Arg/His/Asn, Gln/Arg, and Thr/Val, respectively.

The lectin shown by the sequence number 5 is a novel lectin that can be extracted from *Naematoloma sublateritium* (hereinafter referred to as NSL). The 10<sup>th</sup> and 17<sup>th</sup> Xaas of the sequence number 5 may be any amino acid residue but are preferably Cys. The 13<sup>th</sup>, 14<sup>th</sup>, and 16<sup>th</sup> Xaas are Asp/Thr, Ser/Ala, and Gln/Lys, respectively.

The lectin shown by the sequence number 6 is also a novel lectin that can be extracted from *Naematoloma sublateritium* (hereinafter referred to as NSL). The sequence number 6 shows a variant in which one Asn is inserted to the peptide of the sequence number 5. Thus, the 10<sup>th</sup> and 18<sup>th</sup> Xaas of the sequence number 6 may be any amino acid residue but are preferably Cys. The 14<sup>th</sup>, 15<sup>th</sup>, and 17<sup>th</sup> Xaas are Asp/Thr, Ser/Ala, and, Gln/Lys, respectively.

Since the proteins or peptides shown by the sequence numbers 2 to 6 are novel, the present invention provides a L-fucose α1→6 specific lectin that is (a) protein or peptide consisting of an amino acid sequence shown in any of sequence numbers 2 to 5 or (b) protein or peptide in which one or plurality of amino acid(s) is/are deleted, inserted, or substituted in the amino acid sequence shown in any of sequence numbers 2 to 5 and which is functionally-equivalent to protein or peptide having an amino acid sequence shown in any of the sequence numbers 2 to 5. The term "functionally-equivalent" herein means an affinity having a association constant of $1.0 \times 10^4 M^{-1}$ or more to a L-fucose α1→6 sugar chain, preferably $1.0 \times 10^5 M^{-1}$ or more, and more preferably $1.0 \times 10^6 M^{-1}$ or more. An example of the variant shown in (b) is the protein or peptide shown by the sequence number 6.

The present invention also provides a gene that codes (a) protein or peptide consisting of an amino acid sequence shown in any of sequence numbers 2 to 5 or (b) protein or peptide in which one or plurality of amino acid(s) is/are deleted, inserted, or substituted in an amino acid sequence shown in any of sequence numbers 2 to 5 and which is functionally-equivalent to protein or peptide having an amino acid sequence shown in any of sequence numbers 2 to 5. The wording "functionally-equivalent" has the same meaning as the above one.

The homology between the proteins or peptides shown by the sequence numbers 2 to 6 is at least 37% (see Table 14). Thus, the present invention also provides a L-fucose α1→6 specific lectin that is protein or peptide that has at least 37% or more homology to an amino acid sequence shown in any of sequence numbers 2 to 6 and that is functionally-equivalent to protein or peptide having an amino acid sequence shown in any of sequence numbers 2 to 5. The wording "functionally-equivalent" has the same meaning as the above one.

The L-fucose α1→6 specific lectin can be isolated from basidiomycete and/or ascomycete by an appropriate combination of known extraction method, separation method, and purification method for example. For example, a process may be used an aqueous solvent to obtain a water-soluble extract of basidiomycete and/or ascomycete. From this extract, lectin is obtained for which (vi) a molecular weight by SDS-PAGE is 4,000 to 40,000 and preferably 4,000 to 20,000 and (v) an affinity shown by a association constant to an L-fucose α1→6 sugar chain is $1.0 \times 10^4 M^{-1}$ or more, preferably $1.0 \times 10^5 M^{-1}$ or more, and more preferably $1.0 \times 10^6 M^{-1}$ or more (at 25 degrees C.).

The basidiomycete is preferably selected from among at least one of Strophariaceae, Tricholomataceae, Polyporaceae, and Amanitaceae. In particular, Strophariaceae such as *Pholiota terrestris* (*Pholiota terrestris* Overholts), *Pholiota squarrosa* (*Pholiota squarrosa* (Fr.) Kummer), *Pholiota adiposa* (*Pholiota adiposa* (Fr.) Kummer), *Stropharia rugosoannulata* (*Stropharia rugosoannulata* Farlow in Murr.), *Naematoloma sublateritium* (*Naematoloma sublateritium* (Fr.) Karst or *Hypholoma sublateritium* (Fr.) Quel), Tricholomataceae such as *Lepista sordida* (*Lepista sordida* (Schum.: Fr.) Sing.), Polyporaceae such as *Trichaptum elongatum* (*Trichaptum elongatum*), *Microporus affinis* (*Mi-*

*croporus vernicipes*), Amanitaceae such as *Amanita muscaria* (*Amanita muscaria*). From among these basidiomycete and/or ascomycete, a carpophore is preferably used.

A method of obtaining an extract of basidiomycete for example is not particularly limited so long as the method can cause the aqueous solvent to have a contact with the carpophore of basidiomycete for example. From the viewpoint of the extraction efficiency, such a method is preferred that a carpophore of basidiomycete for example is pulverized in aqueous medium to obtain suspension. A pulverization method may be a general pulverization method using a mixer or a homogenizer for example.

The aqueous solvent may be buffer solution or a mixture of water or buffer solution and organic solvent that may be mixed with water for example and is preferably buffer solution or a mixture of organic solvent and buffer solution.

The buffer solution is not particularly limited and may be known buffer solutions among which buffer solution having a buffering ability in the range of pH 3 to 10 is preferred and buffer solution having a buffering ability in the range of pH 6 to 8 is more preferred. Specifically, phosphate buffer, citrate buffer, acetic acid buffer, and Tris buffer for example may be used among which phosphate buffer is preferred from the viewpoint of the extraction efficiency.

The buffer solution may not have a particular limited salt concentration. The salt concentration is preferably 1 to 100 mM and more preferably 5 to 20 mM from the viewpoint of the extraction efficiency and the buffering ability.

The buffer solution can further include salt. For example, phosphoric acid buffered normal saline obtained by further adding dietary salt to phosphate buffer for example is preferred as aqueous solvent in the present invention.

The organic solvent may be any organic solvent that may be mixed with water without any limitation among which acetone, methanol, ethanol, 2-propanol, and acetonitrile are preferred. Organic solvent may be preferably mixed with water or buffer solution with a content of 10 to 40 mass %.

The extraction process preferably further includes a process of removing, from the mixture of aqueous solvent and a carpophore of basidiomycete for example, insoluble materials to the aqueous medium. The method of removing insoluble matters may be filtration or centrifugal separation for example but is preferably centrifugal separation from the viewpoint of the removal efficiency.

The extraction process is particularly preferably a process to pulverize a carpophore of basidiomycete for example in phosphate-buffered saline to remove insoluble materials by a centrifugal separation to thereby obtain an aqueous solvent extract.

The method of manufacturing an L-fucose α1→6 specific lectin can provide a further efficient purification when using any of the following purification means.

(Purification Method 1)

The water solvents extract obtained by the process is subjected to an ammonium sulfate precipitation method to thereby obtain a lectin-containing fraction. Then, the resultant lectin fraction is purified by hydrophobic chromatography and reversed-phase chromatography.

(Purification Method 2)

The water solvents extract obtained by the process is subjected to affinity chromatography using a carrier in which thyroglobulin is immobilized to agarose.

(Purification Method 3)

The water solvents extract obtained by the process is subjected to an ammonium sulfate precipitation method to thereby obtain a lectin-containing fraction and the lectin-containing fraction is dialyzed against distilled and lyophilized. Thereafter, the crude lectin fraction is dissolved in Tris buffer solution and is subsequently subjected to ion-exchange chromatography. Then, the resultant activity fraction is concentrated and is subsequently separated by gel filtration.

The manufacture method of the present invention may include a step of subjecting, to a dialysis processing, the fraction including lectin obtained through the purification, and a step of subjecting, to a lyophilizing, lectin solution obtained through the dialysis processing. As a result, lectin can be isolated easily. The dialysis processing step and the lyophilizing step may be performed by known methods that are generally used.

An L-fucose α1→6 specific lectin that is (a) protein or peptide consisting of an amino acid sequence shown in any of sequence numbers 2 to 5 or (b) protein or peptide in which one or plurality of amino acid(s) is/are deleted, inserted, or substituted in the amino acid sequence shown in any of sequence numbers 2 to 5 and which is functionally-equivalent to protein or peptide having the amino acid sequence shown in any of sequence numbers 2 to 5 may be obtained not only by the extraction from natural plants but also by an artificial expression in a host different from the naturally-derived one or a chemical synthesis. The substance as described above is also within the technical scope of the present invention. The expression in the host and the chemical synthesis can be carried out by known methods that are generally used.

The present invention also provides a method of detecting an L-fucose α1→6 sugar chain using the L-fucose α1→6 specific lectin. The L-fucose α1→6 specific lectin can recognize an L-fucose α1→6 sugar chain more specifically than in a conventional case and can be bound thereto. Thus, the L-fucose α1→6 specific lectin is preferably used to specifically detect a sugar chain compound including an L-fucose α1→6 sugar chain such as polysaccharide, glycolipid, or glycoprotein for example.

The L-fucose α1→6 specific lectin used in the detection method preferably uses a labeled lectin. The label lectin of the present invention at least includes an L-fucose α1→6 specific lectin and a label means and is labeled so that the label lectin can be detected.

The label means is not particularly limited and may be a known labeling method, including, for example, a radioisotope labeling or the bonding of a label compound for example.

The label compound is not particularly limited and may be the one that is generally used for this application including, for example, a direct or indirect label compound, enzyme, or a fluorescent compound for example. Specific examples of the label compound include biotin, digoxigenin, horseradish peroxidase, fluorescein isothiocyanate, or CyDye for example. These label compounds can be bound to lectin by a conventional method.

The L-fucose α1→6 specific lectin is preferably basidiomycete-derived lectin, particularly preferably PTL, SRL, NSL, LSL, and AML, and more preferably PTL and SRL. As shown in the example, PTL and SRL are different from the conventional L-fucose specific lectins in that PTL and SRL are not bound to L-fucose other than L-fucose α1→6 and a high mannose sugar chain not having L-fucose. Thus, PTL and SRL are optimal as an L-fucose α1→6 specific lectin used in the detection method of the present invention.

The detection of an L-fucose α1→6 sugar chain can be performed, for example, by lectin chromatography using the immobilized L-fucose α1→6 specific lectin. The lectin chromatography is affinity chromatography using the property of lectin binding specifically to a sugar chain. When the lectin chromatography is combined with HPLC (HPLAC), a high throughput analysis can be expected.

A carrier to which an L-fucose α1→6 specific lectin is immobilized generally includes gel material such as agarose, dextran, cellulose, starch, or polyacrylamide for example. These gel materials may be the commercially-available ones without a particular limitation, including, for example, sepharose 4B and sepharose 6B (GE Healthcare Bioscience).

The column used in the lectin chromatography includes the one in which lectin is immobilized to a microplate or a nanowell.

The immobilized L-fucose α1→6 specific lectin has a concentration generally in the range from 0.001 to 100 mg/ml and preferably 0.01 to 20 mg/ml. When a carrier is agarose gel, the carrier is activated by CNBr for example and is subsequently coupled with lectin. Lectin also may be immobilized to gel using an activated spacer. Alternatively, lectin also may be immobilized to gel using a formyl group to be subsequently reduced by NaCNBH$_3$. Alternatively, commercially-available activated gel such as NHS-sepharose (GE Healthcare Bioscience) also may be used.

An L-fucose α1→6 sugar chain sample is applied to a column and then buffer solution is caused to flow therein for the purpose of cleaning and equilibration. One example of buffer solution has a mol concentration of 5 to 500 mM and preferably of 10 to 500 mM, has a pH of 4.0 to 10.0 and preferably 6.0 to 9.0, has a NaCl content of 0 to 0.5M and preferably 0.1 to 0.2 M, and has a CaCl$_2$, MgCl$_2$, or, MnCl$_2$ content of 0 to 10 mM and preferably 0 to 5 mM.

After unbound materials were washed with the buffer, L-fucose α1→6 sugar chain is eluted with neutral nondenaturing buffer solution that can cause the sugar chain to be effectively eluted therein by a desorption agent such as sodium chloride or hapten sugar for example. This buffer solution also may be the same one as the above buffer solution. The desorption agent has a concentration of preferably 1 to 500 mM and particularly preferably 10 to 200 mM.

In addition to the above method, the sugar chain also can be detected by chromatography, lectin chip, enzyme-linked immunosorbent assay (ELISA), aggregation, surface plasmon resonance method such as the Biacore® system, or electrophoresis for example by method well-known to those skilled in the art.

A specimen including the sugar chain is not particularly limited. A specimen including the sugar chain may include, for example, blood, blood plasma, blood serum, eyewater, saliva, body fluid, breast fluid, urine, cell culture supernatant, and secretion from a transgenic animal.

A specific example of an L-fucose α1→6 sugar chain as the subject of the detection method is a sugar chain synthesized by an α1→6 fucosyltransferease (FUT8). The L-fucose α1→6 sugar chain may be in α-fetoprotein, α5β1-integrin, TGFβ receptor, or EGF receptor for example. The sugar chain acting on the detection method is preferably a tumor marker.

An accurate detection of α1→6 fucosylated α-fetoprotein is useful for an early diagnosis of hepatocyte cancer that clinically complicates cirrhosis, a minute follow-up of hepatocyte cancer, an accurate determination of a therapeutic effect, an early detection of embryonal tumor, and an index of liver regeneration in fulminant hepatitis for example. The α5β1-integrin to which L-fucose α1→6 is transferred is also expected as an index for the diagnosis of liver cancer.

The subject of the detection method of the present invention includes, in addition to hepatocyte cancer, the diagnosis of tumors (e.g., prostate cancer, breast cancer, stomach cancer, small intestinal cancer, large intestine cancer, colorectal cancer, renal cell cancer, pancreatic cancer, small cell lung cancer, non-small cell cancer, uterus cancer, ovary cancer, thyroid cancer, soft tissue sarcoma, bone cancer, melanoma, glioblastomas, astrocytoma, medulloblastoma, acute lymphoma, malignant lymphoma, Hodgkin's disease, non-Hodgkin's disease, acute myeloid leukemia, chronic lymphatic leukemia), allergy disease, autoimmune disorder, and cardiovascular disease such as emphysema.

The L-fucose α1→6 specific lectin is a novel lectin that is different from a conventionally known lectin in the physicochemical property and the biochemical property such as bond specificity to a sugar chain for example. In particular, since the L-fucose α1→6 specific lectin specifically recognizes an L-fucose α1→6 bond, the L-fucose α1→6 specific lectin can be used as a diagnostic agent, a test reagent, a specific adsorption agent for carbohydrate separation analysis, and an immune-regulating drug for example. Thus, the present invention provides a diagnostic agent that includes the L-fucose α1→6 specific lectin as an active ingredient and that is used to detect an L-fucose α1→6 sugar chain synthesized by a L-fucose α1→6 transferase, and a diagnostic agent kit including the diagnostic agent. The diagnostic agent or diagnostic agent kit is used to diagnose the hepatocyte cancer for example.

The present invention also provides a method of fractionating an L-fucose α1→6 sugar chain including a step of using the L-fucose α1→6 specific lectin as a bonding medium for a L-fucose α1→6 sugar chain to fractionate an L-fucose α1→6 sugar chain and non-L-fucose α1→6 sugar chain.

The L-fucose α1→6 specific lectin used in the method of fractionating an L-fucose α1→6 sugar chain is preferably basidiomycete lectin, particularly preferably PTL, SRL, NSL, LSL, and AML, and further preferably PTL and SRL.

The fractionation method of the present invention is, for example, lectin chromatography using the immobilized L-fucose α1→6 specific lectin. The details thereof are the same as those described with regard to the detection method. When the L-fucose α1→6 sugar chain is purified, an L-fucose α1→6 specific lectin is bonded to a column carrier consisting of agarose or cellulose via a functional group to thereby, then sugar chain sample is applied. After the sample is through the column, an adsorbed L-fucose α1→6 sugar chain is collected. When a non-L-fucose α1→6 sugar chain is purified, such a sugar chain sample is collected that is not adsorbed while the sugar chain sample is being sent through the column.

The subject purified by the fractionation of the present invention may be the two types of an L-fucose α1→6 sugar chain and a non-L-fucose α1→6 sugar chain. Specific example thereof is a sugar chain bonded of antibody, and is preferably a sugar chain of human IgG.

The purity of the sugar chain fractionated by the fractionation method (i.e., a ratio of, in the case of an L-fucose α1→6 sugar chain, an L-fucose α1→6 sugar chain to the total amount of an L-fucose α1→6 sugar chain and a non-L-fucose α1→6 sugar chain and a ratio of, in the case of a non-L-fucose α1→6 sugar chain, a non-L-fucose α1→6 sugar chain to the total amount of a L-fucose α1→6 sugar chain and a non-L-fucose α1→6 sugar chain) is generally 90 to 100%, preferably 95 to 100%, and particularly preferably 99 to 100%.

The present invention also provides a antibody preparation including, as an active ingredient, an L-fucose α1→6 sugar chain or a non-L-fucose α1→6 sugar chain having the purity of generally 90 to 100%, preferably 95 to 100%, and particularly preferably 99 to 100%. In particular, the antibody preparation consisting of an antibody from which antibody to which α1→6 L-fucose is transferred is removed is expected to provide an improved ADCC activity. Candidates thereof include: Rituxan (chimeric antibody, NH lymphoma), Herceptin (humanized antibody, breast cancer), Erbitux (chimeric antibody, large intestine cancer, head and neck cancer), Zevalin (mouse antibody, NH lymphoma), Campath (humanized antibody, B cell chronic lymphatic leukemia), Bexxar (mouse antibody, NH lymphoma), and Avastin (humanized antibody, metastatic large intestine cancer) for example.

The antibody medical drug obtained by the fractionation method of the present invention may be used in the same method as the conventional method (with regard to a pharmacologically approved carrier, auxiliary agent or additive agent, an administration route, or an administration form for example) except for that the antibody medical drug obtained by the fractionation method of the present invention may be used with a low dose regimen and a low dosage because this drug has a higher specific activity than that of the conventional one.

The present invention also provides an L-fucose α1→6 sugar chain or a non-L-fucose α1→6 sugar chain having a purity of 90 to 100% fractionated by the fractionation method as well as a medical drug including as an active ingredient the L-fucose α1→6 sugar chain or non-L-fucose α1→6 sugar chain having a purity of 90 to 100%. The purity means, in the case of an L-fucose α1→6 sugar chain, the ratio of an L-fucose α1→6 sugar chain to the total amount of an L-fucose α1→6 sugar chain and a non-L-fucose α1→6 sugar chain and, in the case of a non-L-fucose α1→6 sugar chain, a ratio of a non-L-fucose α1→6 sugar chain to the total amount of an L-fucose α1→6 sugar chain and a non-L-fucose α1→6 sugar chain. The medical drug is preferably the antibody preparation.

The present invention also provides a screening method of an L-fucose α1→6 sugar chain. This method includes a step of causing fluid including a sugar chain to act on the L-fucose α1→6 specific lectin and collecting an L-fucose α1→6 sugar chain adsorbed by the L-fucose α1→6 specific lectin. This screening method is useful to search a novel tumor marker having an L-fucose α1→6 sugar chain. It is also possible to use an L-fucose α1→6 specific lectin that can be used for the detection method of the present invention to easily screen a disease marker including an L-fucose α1→6 sugar chain.

The L-fucose α1→6 specific lectin used in the screening method is preferably basidiomycete-derived lectin, is particularly preferably selected from at least one of Strophariaceae, Tricholomataceae, Polyporaceae, and Amanitaceae and is more preferably PTL, SRL, NSL, LSL, and/or AML among which PTL and SRL are most preferred.

The present invention also provides a method of screening of an L-fucose α1→6 sugar chain specific lectin. This method uses, for example, the immobilized L-fucose α1→6 specific lectin. Fluid including a plurality of sugar chains is allowed to act on an immobilized lectin. Then, the test profile of a sugar chain adsorbed to the immobilized lectin (e.g., gel electrophoresis) is compared with the control profile of the sugar chain adsorbed by the lectin when the fluid acts on an immobilized PTL or SRL. Thus, such an L-fucose α1→6 specific lectin is extracted that has the same profile as that of the control. Since it is not required to identify a sugar chain adsorbed to each specimen lectin, a target lectin can be screened by a very simple operation. The L-fucose α1→6 specific lectin thus extracted may be used as a control for the next screening method. Another method is also possible to use cDNA partially or entirely coding the amino acid sequence shown by sequence number 1 as a primer to pick up the cDNA of an L-fucose α1→6 specific lectin from the specimen lectin.

Figure 2:
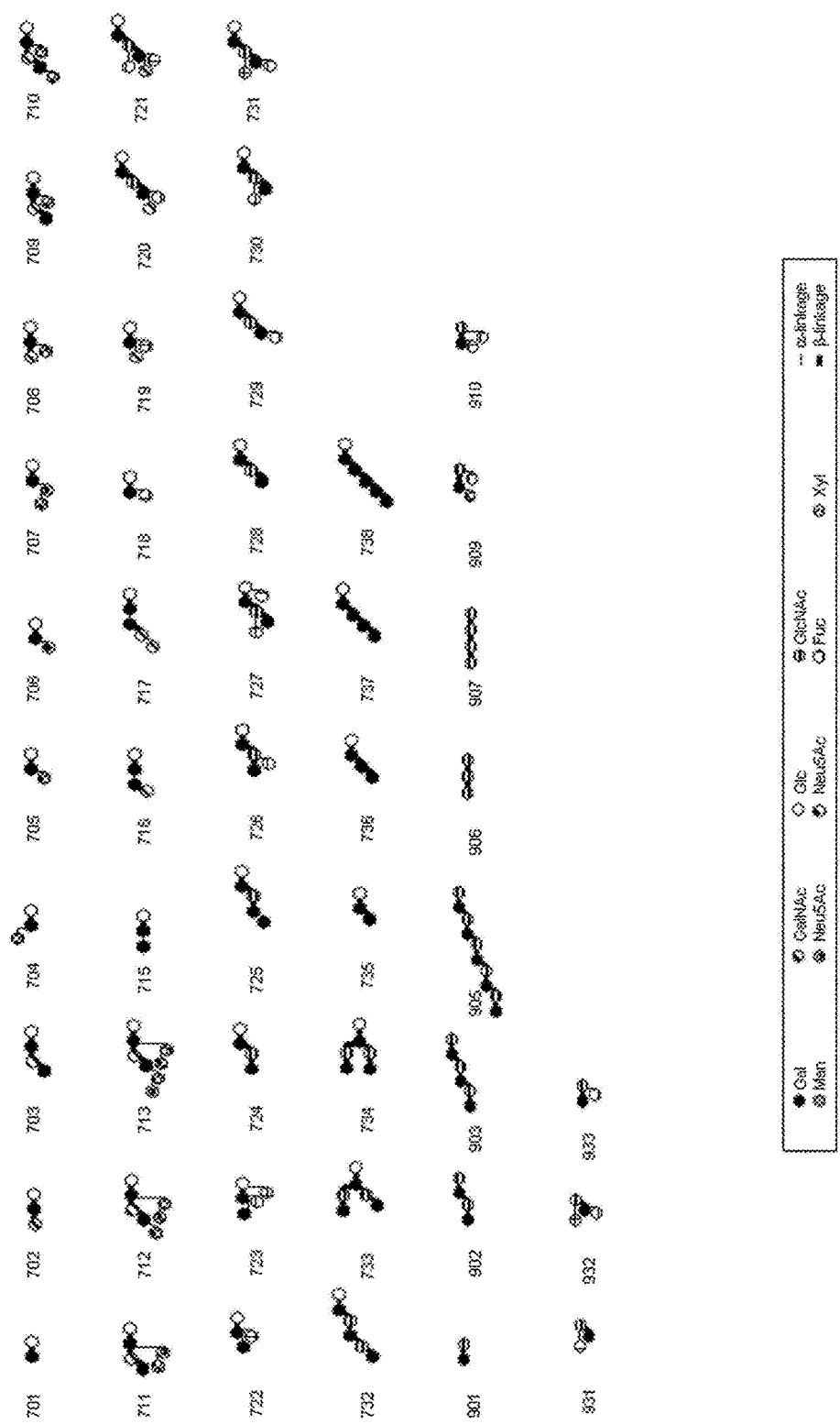
FIG. 2 is a structural diagram of an L-fucose α1→6 oligosaccharide and a non-L-fucose α1→6 oligosaccharide used in a working example and a comparison example of the present invention.

The sugar chain includes at least one of the L-fucose α1→6 sugar chains as shown in FIG. 1 and FIG. 2 and preferably includes at least one of non-L-fucose α1→6 sugar chains to which an L-fucose other than an α1→6 bond is transferred and at least one sugar chain not having L-fucose (e.g., high mannose sugar chain). By the addition thereof, it can be confirmed that no affinity is found with a sugar chain other than an L-fucose α1→6 sugar chain.

The profile of the adsorbed sugar chain can be measured by a method well-known to those skilled in the art such as various chromatographys, mass analysis, gel electrophoresis, lectin chip, enzyme-linked immunosorbent assay (ELISA), surface plasmon resonance such as Biacore® system for example, or electrophoresis for example.

EXAMPLE

The following section will describe in more details the present invention by way of examples and comparison examples. However, the present invention is not limited to the following examples.

Examples 1 and 2

Manufacture, Property Measurement, and Characterization of PTL and SRL)

(1) Manufacture of PTL

Example 1

Based on the purification process shown in FIG. 3, *Pholiota terrestris* lectin (PTL) was purified from the mushroom *Pholiota terrestris*.
(Extraction)

All procedures were carried out at 4° C. *Pholiota terrestris* freeze-dried powders were extracted with 50 ml of 10 mM Tris buffer (pH 7.2) at 4 degrees C. for 2 hours. The resultant liquid was centrifuged (15,000 rpm, 20 min, 4 degrees C.). Then, the supernatant was subjected to gauze filtration to thereby obtain the first extract. This extraction residue was re-extracted with 50 ml of 10 mM Tris buffer (pH 7.2) at 4 degrees C. overnight. After this liquid was centrifuged (15,000 rpm, 20 min, 4 degrees C.), the supernatant was subjected to a gauze filtration to thereby obtain the second extract. Then, these extracts were collectively filtered by a filter paper to thereby obtain *Pholiota terrestris* extract.
(Ion-Exchange Chromatography)

Figure 4:
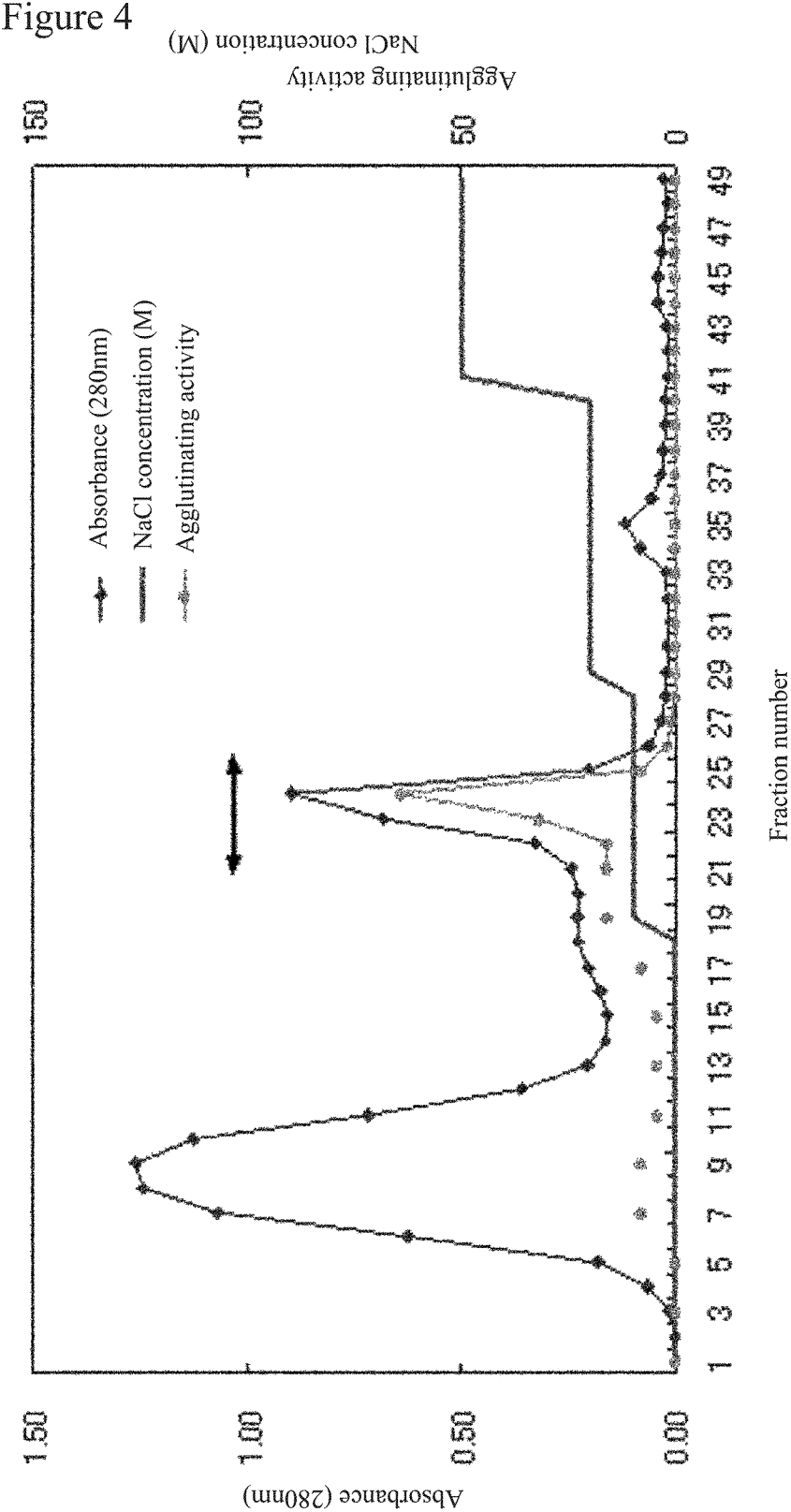
FIG. 4 is an elution diagram of ion-exchange chromatography of PTL of Example 1.

The extract (87 ml) was applied to a column of DEAE-sepharose (GE Healthcare Bioscience) equilibrated with 10 mM Tris buffer (pH 7.2). After the column was washed with the buffer, the bound fraction was desorbed with 0.1 M NaCl in the buffer. Then, the fractions showing hemagglutination activity (shown by ←→ of FIG. 4) were dialyzed extensively against distilled water and lyophilized.
(Affinity Chromatography)

Figure 5:
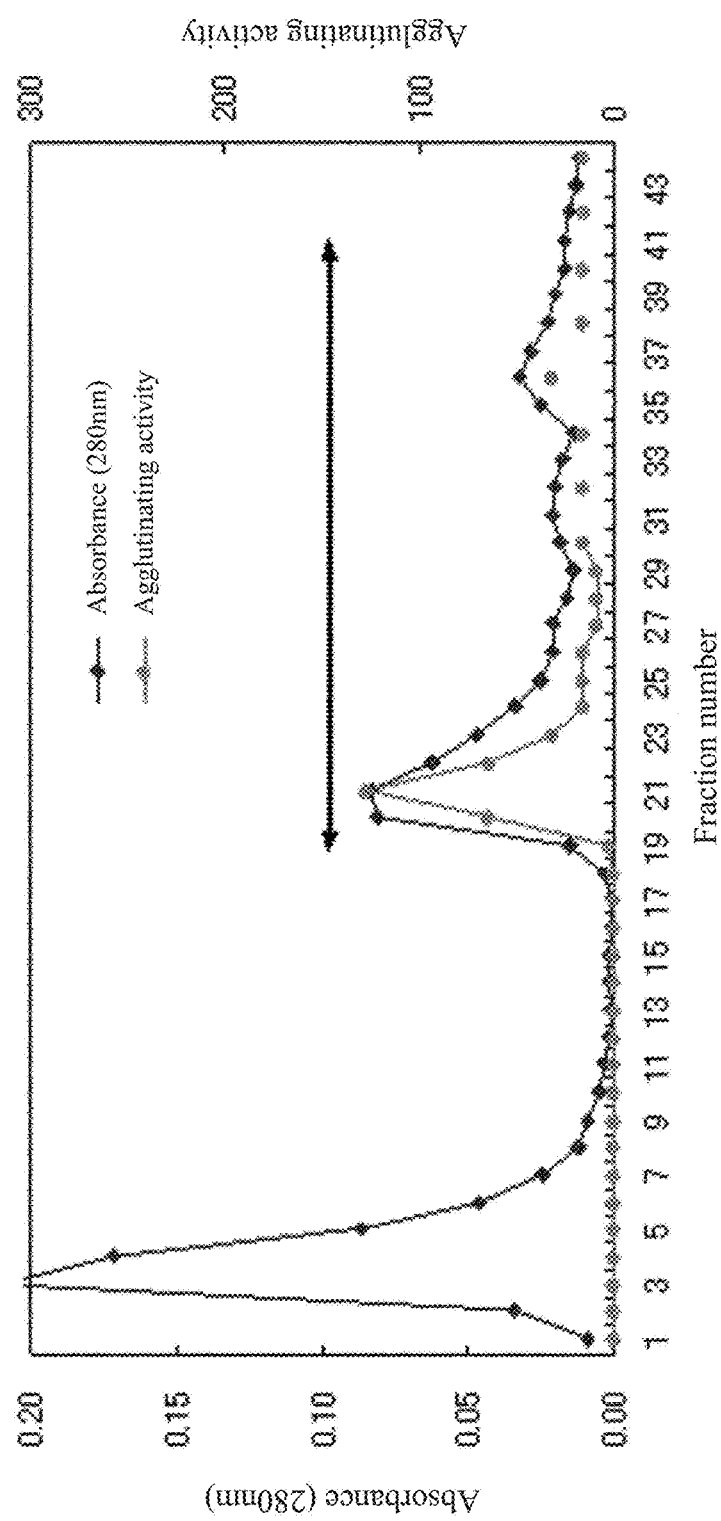
FIG. 5 is an elution diagram of affinity chromatography of PTL of Example 1.

The lyophilized dialyzate was redissolved 10 mM phosphate buffered saline (pH 7.4, hereinafter simply referred to as PBS). Then, the extract solution was applied to a column of thyroglobulin immobilized-agarose equilibrated with the same buffer. After the column was washed with PBS, the bound fraction was desorbed with 0.2 M ammonia. Then, the fractions showing hemagglutination activity (shown by ←→ of FIG. 5) were collected, ultrafiltered, and lyophilized, thereby obtaining 1.07 mg of PTL.

(SDS-PAGE)

Figure 6:
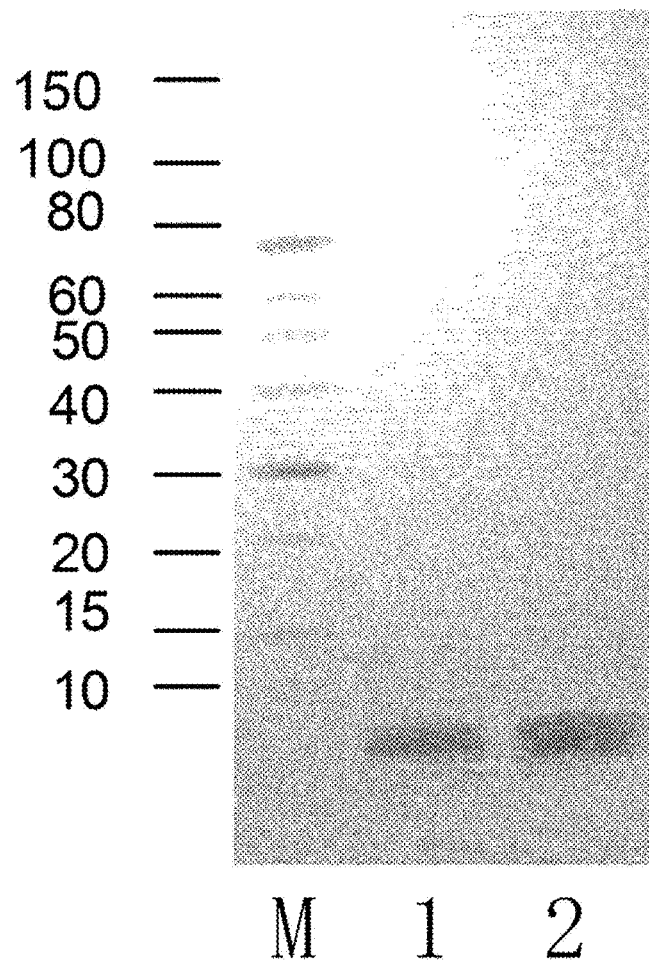
FIG. 6 illustrates the result of SDS-PAGE of PTL of Example 1 (a photograph as a substitute of a drawing).

SDS-PAGE was performed by an electrophoresis apparatus of Phastsystem (GE Healthcare Bioscience) and a gel of Gradient8-25 (GE Healthcare Bioscience). The sample solution and the molecular weight marker were used both in an amount of 1 μl. The electrophoresis was performed based on the product protocol and a conventional method. FIG. 6 shows the result of SDS-PAGE of PTL. In FIG. 6, the lane M, lanes 1 and 2 correspond to the followings. Lane M: molecular weight marker (APRO), lane 1: PTL, 2-mercaptoethanol (−), lane 2: PTL, 2-mercaptoethanol(+), Gel: Gradient8-25, Sample: 1 μl/lane, Stain: Coomassie Brilliant Blue (CBB)

On SDS-PAGE with 8-25% gel, the major component was confirmed to be PTL.

(2) Manufacture of SRL

Example 2

Based on the purification process shown in FIG. 7, *Stropharia rugosoannulata* lectin (SRL) was purified from the mushroom *Stropharia rugosoannulata*.

(Extraction)

All procedures were carried out at 4° C. *Stropharia rugosoannulata* freeze-dried powders (400 g) were extracted with 1.6 L of PBS at 4 degrees C. for 2 hours. The resultant liquid was centrifuged (15,000 rpm, 20 min, 4 degrees C.). Then, the supernatant was subjected to a gauze filtration to thereby obtain the first extract. This extraction residue was re-extracted with 0.8 L of PBS at 4 degrees C. overnight. This liquid was centrifuged (10,000 rpm, 20 min, 4 degrees C.). Then, the supernatant was subjected to a gauze filtration to thereby obtain the second extract. These extracts were mixed to thereby obtain *Stropharia rugosoannulata* extraction liquid.

(Ammonium Sulfate Precipitation)

Solid $(NH_4)_2SO_4$ (1.3 kg) was added to the resulting supernatant (2.4 L) to obtain 80% saturation. After standing at 4 degrees C. overnight, the precipitates were collected by centrifugation (10,000 rpm, 20 min, 4 degrees C.) and dialyzed extensively against distilled water and lyophilized, thereby collecting *Stropharia rugosoannulata*-80% ammonium sulfate precipitation fraction.

(Hydrophobic Chromatography)

Figure 8:
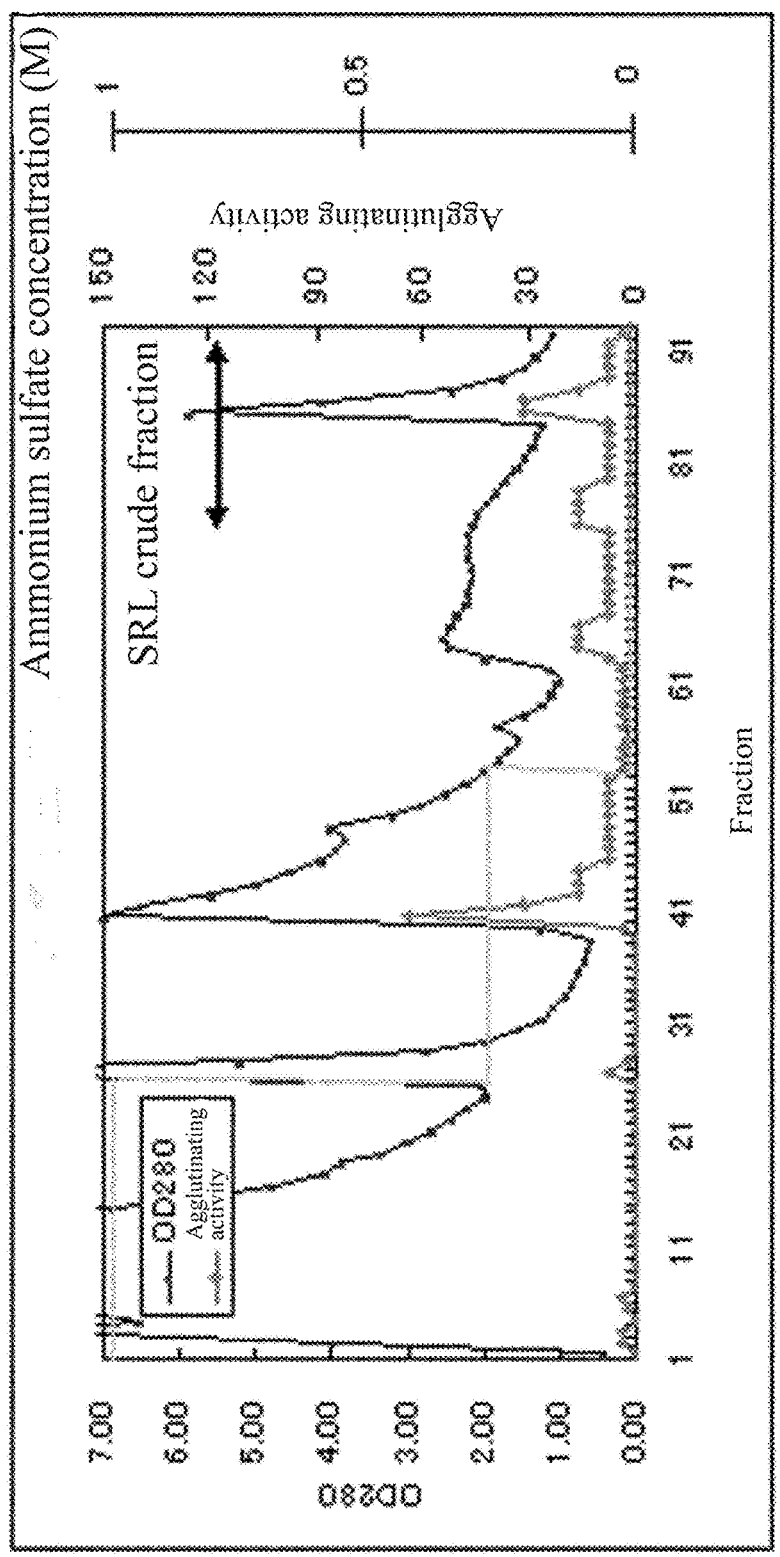
FIG. 8 is an elution diagram of hydrophobic chromatography of SRL of Example 2.

The *Stropharia rugosoannulata*-80% ammonium sulfate precipitation fraction was applied to Butyl-TOYOPEARL 650M (TOSOH CORPORATION) equilibrated with 2 M of ammonium sulfate-PBS to perform hydrophobic chromatography purification. In this chromatography, distilled water elution fractions were collected, ultrafiltered, and lyophilized, thereby obtaining the *Stropharia rugosoannulata* lectin crude fraction (shown by ←—→ of FIG. 8).

(Reversed-Phase Chromatography)

Figure 9:
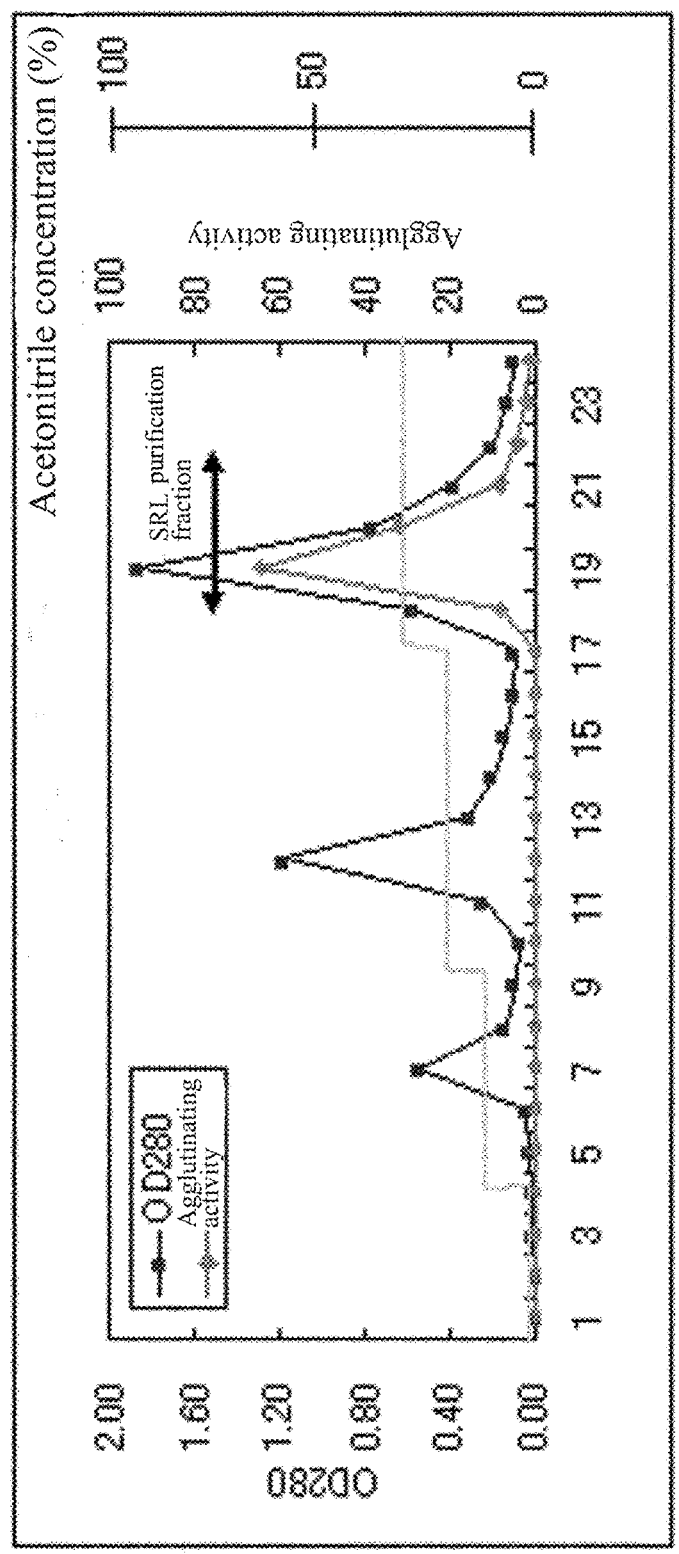
FIG. 9 is an elution diagram of reversed-phase chromatography of SRL of Example 2.

The *Stropharia rugosoannulata* lectin crude fraction was applied to the C8 column (Wako Pure Chemical Industries, Ltd.) equilibrated with 0.05% trifluoroacetic acid (TFA)/acetonitrile (100/0). In this chromatography, 0.05% TFA/acetonitrile (70/30) elution fraction (shown by ←—→ of FIG. 9) was collected. Then, solvent was removed by evaporation at a room-temperature and the resultant dry powders were collected, thereby obtaining 7.5 mg of SRL.

Figure 10:
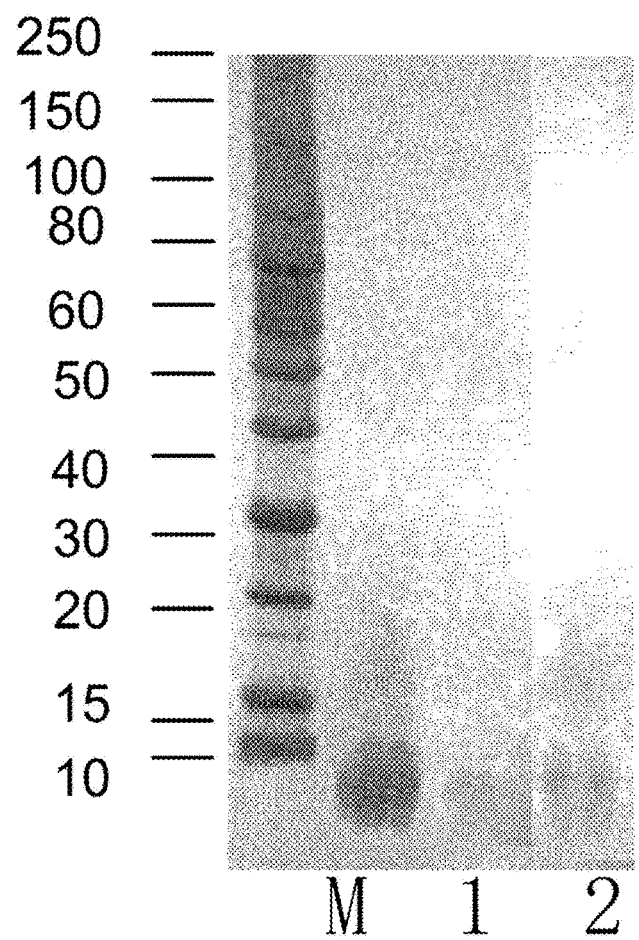
FIG. 10 illustrates the result of SDS-PAGE of SRL of Example 2 (a photograph as a substitute of a drawing).

SDS-PAGE (PhastGel, Gradient8-25) was done in a Phastsystem (GE Healthcare Bio-Sciences). A sample solution and a molecular weight marker were both used in an amount of 1 μl. Then, electrophoresis was carried out based on a product protocol and a conventional method. FIG. 10 shows the result of SDS-PAGE of SRL. In FIG. 10, the lane M, lane 1, and lane 2 correspond to the followings. Lane M: molecular weight marker (APRO), lane 1: SRL, 2-mercaptoethanol(+), lane 2: SRL, 2-mercaptoethanol(−), Gel: Gradient8-25, Sample: 1 μl/Lane, Stain: silver On SDS-PAGE using 8 to 25% gel, it was confirmed that the major component was SRL.

(3) Properties of PTL and SRL

MALDI-TOF Mass Spectrometry Analysis

Figure 11:
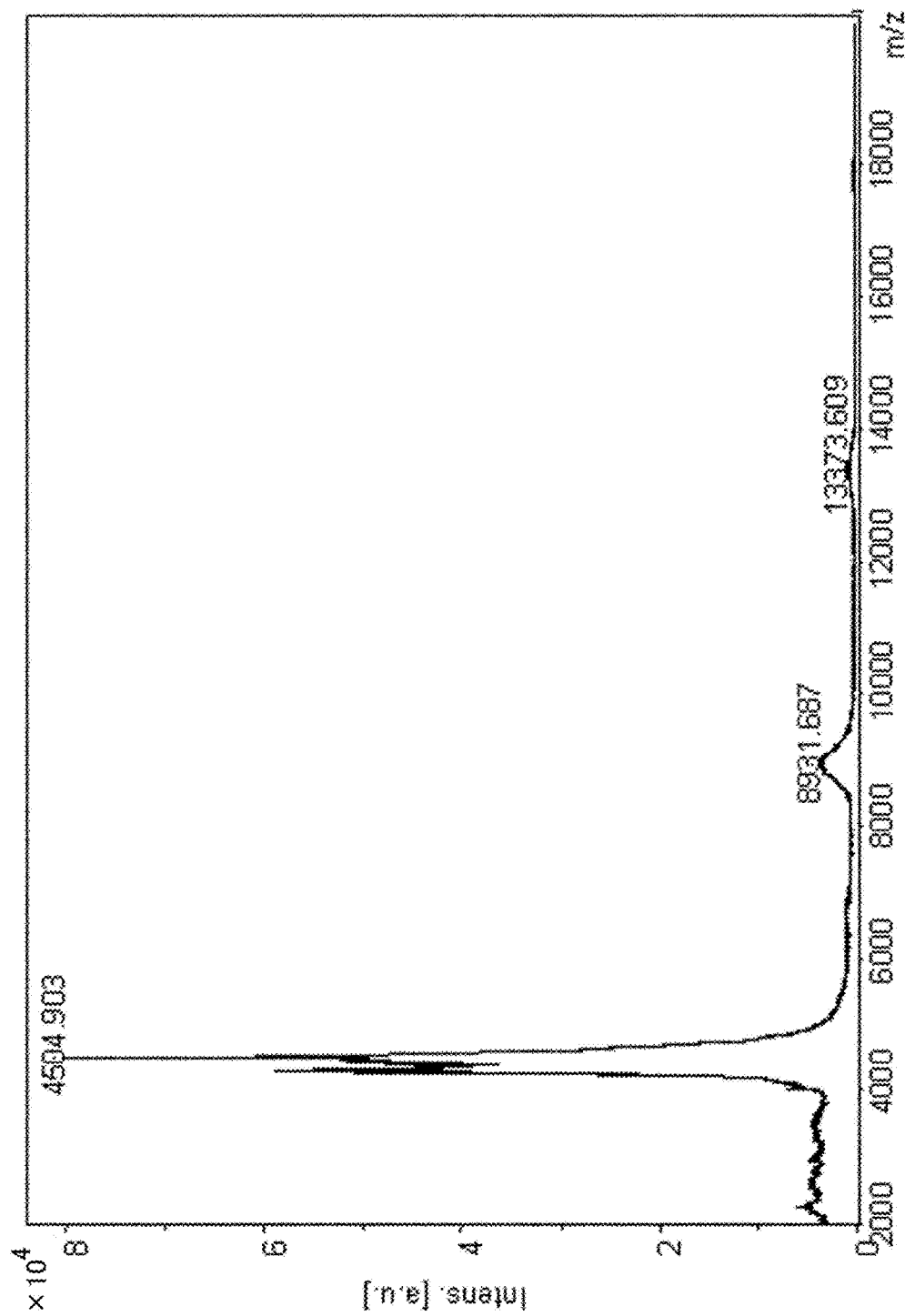
FIG. 11 illustrates the result of MS spectrum of PTL of Example 1.
Figure 12:
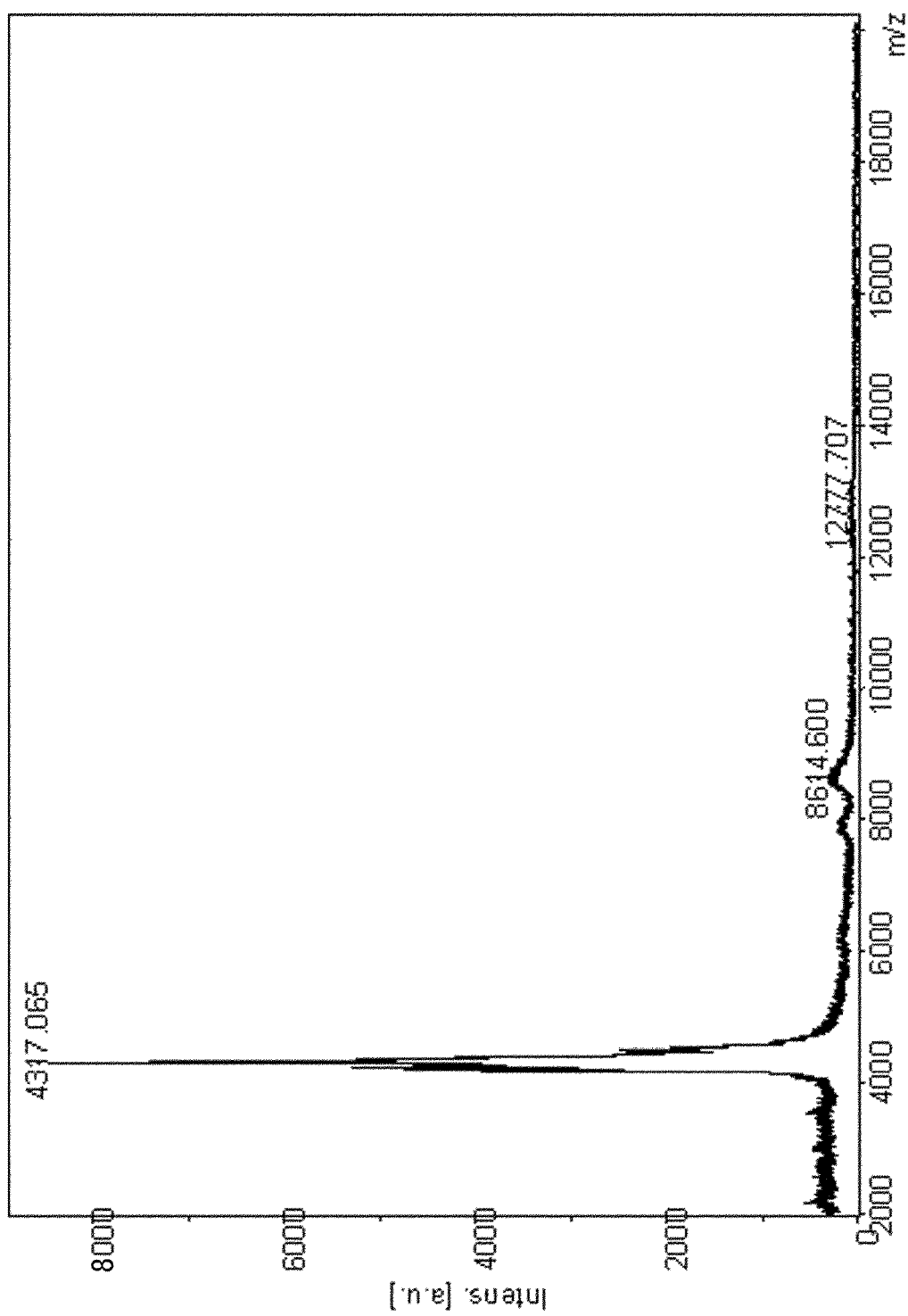
FIG. 12 illustrates the result of MS spectrum of SRL of Example 2.
Figure 13:
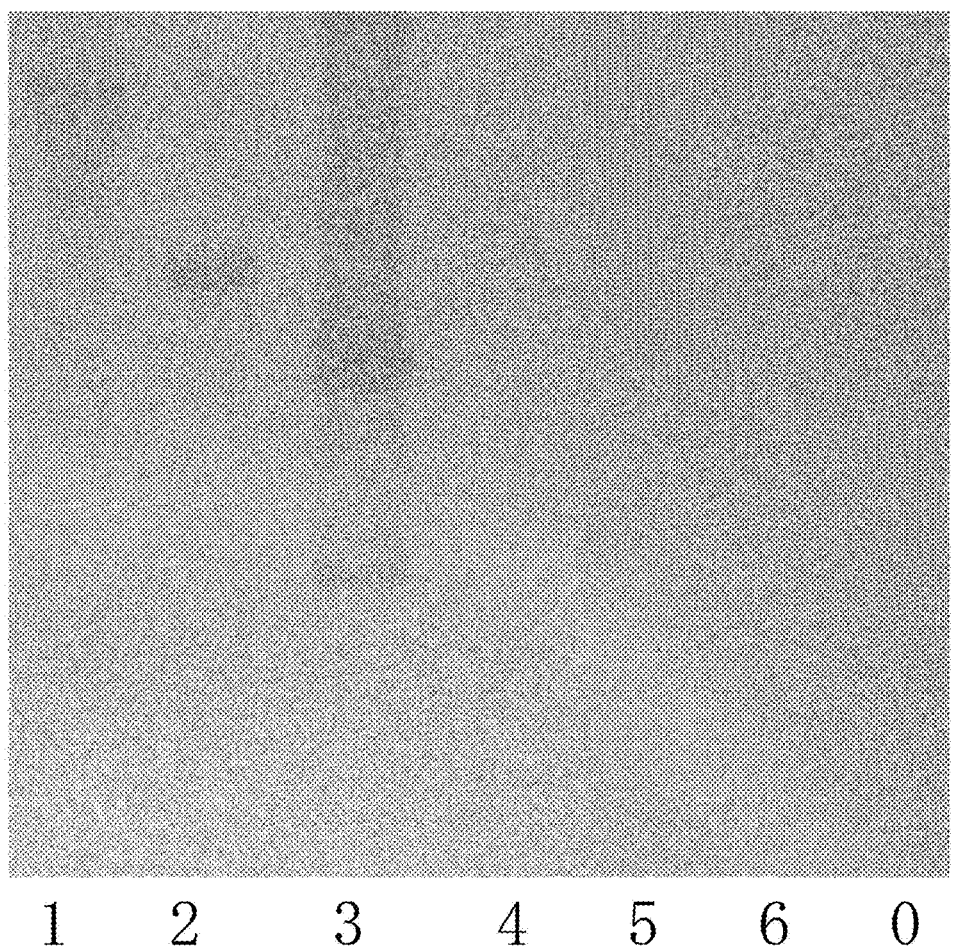
FIG. 13 illustrates the result of Western blotting using PTL of Example 1 (a photograph as a substitute of a drawing).
Figure 14:
FIG. 14 illustrates the result of Western blotting using SRL of Example 2 (a photograph as a substitute of a drawing).
Figure 15:
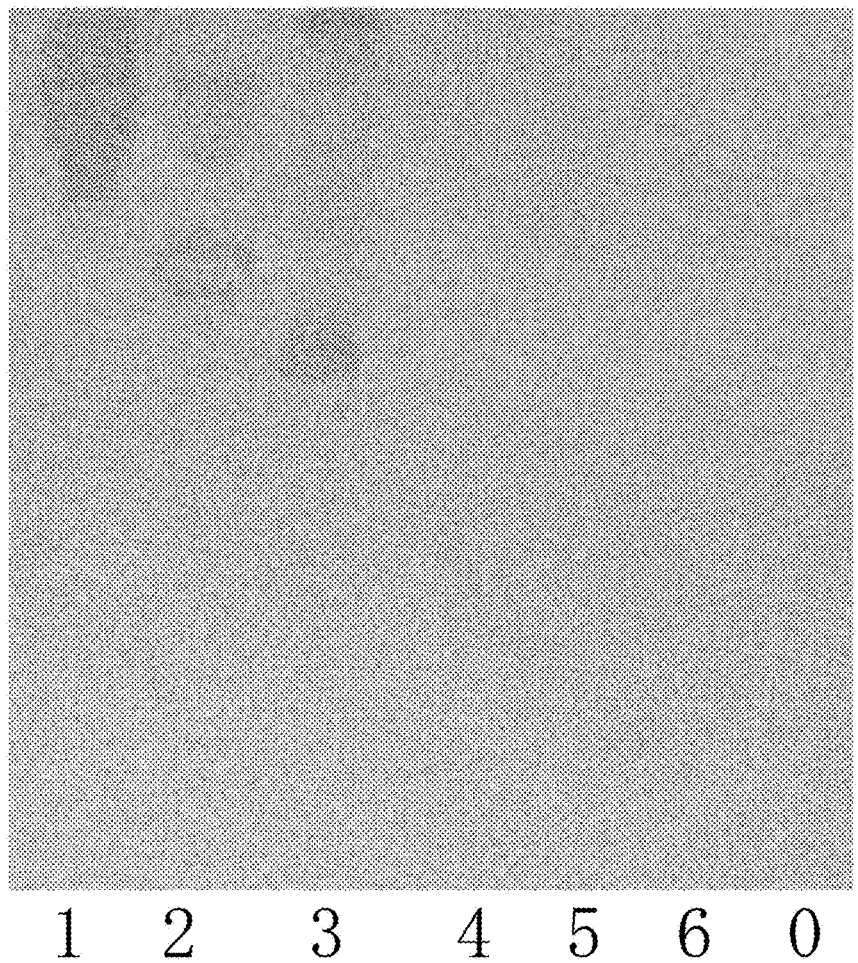
FIG. 15 illustrates the result of Western blotting using AAL of Comparison Example 1 (a photograph as a substitute of a drawing).
Figure 16:
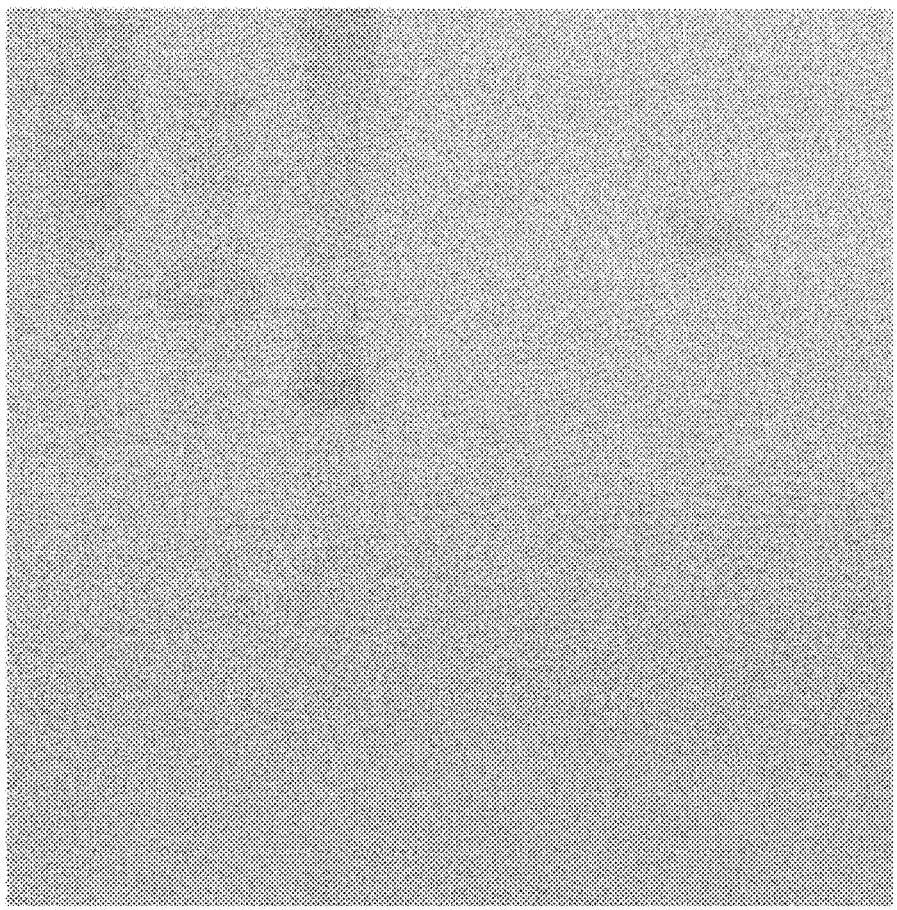
FIG. 16 illustrates the result of Western blotting using AOL of Comparison Example 2 (a photograph as a substitute of a drawing).

PTL of Example 1 and SRL of Example 2 in an amount of 10 μg, respectively, were separately dissolved in TA (a mixture for which a volume ratio between 0.1%-TFA and acetonitrile is 2:1). Then, a saturated matrix dissolved in TA and lectin TA solutions were mixed with a volume ratio of 4:1 and the resultant mixture was dripped in an amount of 1.0 μl on a target plate, thereby preparing a sample. Mass spectrometry analysis apparatus of Autoflex (Bruker Daltonics K.K.) was used to measure the molecular weights of PTL and SRL in LP mode. The result showed that the molecular weight was about 4,500 (FIG. 11 and FIG. 12).

(Amino Acid Sequence Analysis)

With regard to PTL of Example 1 and SRL, of Example 2, the amino acid sequences thereof were analyzed by Protein Peptide Sequencer PPSQ-21 System (SHIMADZU CORPORATION). The results are shown in the sequence numbers 2 and 3, respectively. Any of the sequences were novel.

PTL and SRL were subjected to hagglutinating activity test for rabbit, equine, pig, sheep, human (A, B, O), and actinase E-treated rabbit erythrocytes. The result is shown as hemagglutinating activity in Table 1.

TABLE 1

| | | PTL | | SRL | |
|---|---|---|---|---|---|
| | | Unit: titer (1.0 mg/ml) | Unit: Minimum hemagglutinating concentration (μg/ml) | Unit: titer (1.0 mg/ml) | Unit: Minimum hemagglutinating concentration (μg/ml) |
| Rabbit | | 64 | 5.21 | 64 | 5.21 |
| Equine | | NT | NT | 128 | 2.61 |
| Pig | | 16 | 20.8 | 32 | 10.4 |
| Sheep | | <1 | >333 | <1 | >333 |
| Human | A | <1 | >333 | <1 | >333 |
| | B | <1 | >333 | <1 | >333 |
| | O | <1 | >333 | <1 | >333 |
| Actinase E-treated rabbit | | 2560 | 0.13 | 512 | 0.651 |

NT: Not tested

As can be seen from the above result of the amino acid structure analysis and hemagglutinating activity test, the PTL of Example 1 and the SRL of Example 2 were a novel lectin.

(4) Evaluation of Sugar Binding Specificity of PTL and SRL

Various monosaccharides, oligosaccharides, and polysaccharides shown in Table 2 and glycoproteins shown in Table 3 were subjected to hemagglutinating inhibition test to evaluate PTL of Example 1 and the SRL of Example 2 with regard to the sugar binding specificity.

On a 96 well U-bottom microtiter plate, double dilution series of 10 μl of monosaccharide, oligosaccharide, polysaccharide, and glycoprotein solutions were prepared. Then, lectin solution adjusted in advance to have titer 4 was added in an amount of 10 μl to the respective wells. Then, the plate was subjected to a still-standing at a room temperature for one hour for sensitization. Then, 10 μl of 4%-red blood cell suspension was added to the respective wells and the plate was further subjected to a still-standing at a room temperature for one hour. Thereafter, the dilution factor of the sample solution at which the hemagglutination was completely inhibited was visually judged. The lowest concentration showing the inhibition was assumed as the minimum inhibition concentration. The lower the minimum inhibition concentration is, the higher the specificity to lectin is. The result is shown in Table 2 and Table 3.

For comparison, the sugar binding specificity was evaluated using the following commercially-available lectins: Comparison Example 1: AAL (SEIKAGAKU BIOBUSINESS CORPORATION—J-OIL MILLS, Inc.), Comparison Example 2: AOL (TOKYO CHEMICAL INDUSTRY CO., LTD.—Gekkeikan Sake Company, Ltd.), Comparison Example 3: LCA (SEIKAGAKU BIOBUSINESS CORPORATION—J-OIL MILLS, Inc.), and Comparison Example 4: PSA (SEIKAGAKU BIOBUSINESS CORPORATION—J-OIL MILLS, Inc.). The result is shown in Table 2 and Table 3.

TABLE 2

|  | Example 1 PTL (mM) | Example 2 SRL (mM) | Comparison Example 1 AAL (mM) | Comparison Example 2 AOL (mM) | Comparison Example 3 LCA (mM) | Comparison Example 4 PSA (mM) |
| --- | --- | --- | --- | --- | --- | --- |
| Glucose | >100 | >100 | >100 | >100 | >100 | >100 |
| Galactose | >100 | >100 | >100 | >100 | >100 | >100 |
| Mannose | >100 | >100 | 50 | 100 | 50 | 50 |
| L-fucose | >100 | >100 | 0.391 | 0.391 | >100 | >100 |
| Xylose | >100 | >100 | >100 | >100 | >100 | >100 |
| Rhamnose | >100 | >100 | >100 | 100 | >100 | >100 |
| N-acetylglucosamine | >100 | >100 | >100 | >100 | >100 | >100 |
| N-acetylgalactosamine | >100 | >100 | >100 | >100 | >100 | >100 |
| Metyl α-mannoside | >100 | >100 | >100 | >100 | 50 | 50 |
| Maltose | >100 | >100 | >100 | >100 | 100 | >100 |
| Fructose | >100 | >100 | 25 | 25 | >100 | >100 |
| Sucrose | >100 | >100 | >100 | >100 | >100 | >100 |
| Melibiose | >100 | >100 | >100 | >100 | >100 | >100 |
| Raffinose | >100 | >100 | >100 | >100 | >100 | >100 |
| N-Acetylneuraminic acid | >100 | >100 | >100 | >100 | >100 | >100 |
| N-glycolylneuraminic acid | >100 | >100 | >100 | >100 | >100 | >100 |
| Lactose | >6 | >6 | >6 | >6 | >6 | >6 |
| Serial lactose | >6 | >6 | >6 | >6 | >6 | >6 |

TABLE 3

|  | Example 1 PTL (μl/ml) | Example 2 SRL (μl/ml) | Comparison Example 1 AAL (μl/ml) | Comparison Example 2 AOL (μl/ml) | Comparison Example 3 LCA (μl/ml) | Comparison Example 4 PSA (μl/ml) |
| --- | --- | --- | --- | --- | --- | --- |
| Bovine blood serum albumin | >250 | >250 | >250 | >250 | >250 | >250 |
| Mucin (pig) | >250 | >250 | 15.6 | 62.5 | >250 | >250 |
| Asialomucin (pig) | >250 | >250 | 31.3 | 62.5 | >250 | >250 |
| Fetuin | >250 | >250 | >250 | >250 | >250 | >250 |
| Asialofetuin | >250 | >250 | >250 | >250 | 250 | >250 |
| α1-acidic glycoprotein | >250 | >250 | >250 | >250 | >250 | >250 |
| Transferrin | >250 | >250 | >250 | >250 | >250 | >250 |
| Thyroglobulin | 250 | 250 | 125 | >250 | 62.5 | 62.5 |
| Mucin (bovine) | >250 | >250 | >250 | >250 | >250 | >250 |
| Casein | >250 | >250 | >250 | >250 | >250 | >250 |
| Lactoferrin | >250 | >250 | >250 | >250 | >250 | >250 |
| Ribonuclease | >250 | >250 | >250 | >250 | >250 | >250 |
| Human immune globulin G | >250 | >250 | >250 | >250 | >250 | >250 |
| Human immune globulin A | >250 | >250 | >250 | >250 | >250 | >250 |

As can be seen from Table 2 and Table 3, PTL of Example 1 and the SRL of Example 2 were bound only to thyroglobulin having L-fucose α1→6. On the other hand, AAL of Comparison Example 1 was bound not only to thyroglobulin but also to sugars such as L-fucose, and fructose as well as glycoprotein such as mucin having L-fucose in an O-linked sugar chain. AOL of Comparison Example 2 was bound to sugars such as L-fucose, and fructose and was bound to glycoprotein such as mucin having L-fucose in an O-linked sugar chain. LCA of Comparison Example 3 and PSA of Comparison Example 4 were bound not only to thyroglobulin but also to sugars such as mannose and methyl α-mannosido. It can be said that the PTL of Example 1 and the SRL of Example 2 are an L-fucose α1→6 specific lectin that is not bound to L-fucose and mannose and that is bound only to an L-fucose α1→6 linkaged.

(5) Measurement of Association Constants of PTL and SRL to L-Fucose α1→6 Sugar Chain The association constants of the PTL of Example 1 and the SRL of Example 2 to an L-fucose α1→6 sugar chain were measured by the following procedure.
(Preparation of Oligosaccharide)
Pyridylaminated (PA) sugar chains shown in FIG. 1 and FIG. 2 were used to frontal affinity chromatography (FAC) analysis. PA sugars were purchased from TAKARA BIO INC., SEIKAGAKU BIOBUSINESS CORPORATION, and Masuda Chemical Industries co., LTD. PA sugar were also obtained by pyridylaminating, by GlycoTAG®(TAKARA BIO INC.), an unlabeled sugar chain or a sugar chain obtained by subjecting a sugar chain to enzyme digestion for example.
(Preparation of Lectin Column)

Lectin was dissolved in 0.2 M $NaHCO_3$ buffer solution (pH 8.3) including 0.5 M NaCl and coupled to the NHS-activated sepharose (GE Healthcare Bioscience) by following the manufacturer's instructions. Then, lectin immobilized sepharose was suspended in 10 mM Tris buffer (pH 7.4, TBS) including 08%-NaCl and the resultant matter was filled in a miniature column (φ2 mm×10 mm, 31.4 μl).
(Frontal Affinity Chromatography)
Frontal affinity chromatography was performed using FAC automatic analysis apparatus (FAC-1, SHIMADZU CORPORATION). In particular, the above-prepared lectin column was inserted to a stainless steel holder and the holder was connected to FAC-1 apparatus. The flow rate and the column temperature were maintained at 0.125 ml/min and 25 degrees C., respectively. After the miniature column was equilibrated by the TBS, an excessive volume (0.5 ml to 4 ml) of a PA sugar chain (3.75 nM or 7.5 nM) was continuously inputted to the column using an automatic sampling apparatus.
The fluorescent strength of the eluate of the PA sugar (excitation wavelength of 310 nm and fluorescence wavelength of 380 nm) was monitored to measure the interaction strength [a difference of the front end eluate to the standard oligosaccharide (PA rhamnose): $V-V_0$]. Based on the interaction strength and the effective ligand amount, the association constant Ka was calculated. The result is shown in Tables 4 to 9.

For comparison, association constants were also calculated based on the same procedure as the above one with regard to AAL (Comparison Example 1), AOL (Comparison Example 2), LCA (Comparison Example 3), and PSA (Comparison Example 4) that are said to be core-fucose specific lectins. The result is shown in Tables 4 to 7.

TABLE 4

| | Sugar chain No. | Example 1 PTL ($M^{-1}$) | Example 2 SRL ($M^{-1}$) | Comparison Example 1 AAL ($M^{-1}$) | Comparison Example 2 AOL ($M^{-1}$) | Comparison Example 3 LCA ($M^{-1}$) | Comparison Example 4 PSA ($M^{-1}$) |
|---|---|---|---|---|---|---|---|
| Sugar chain having α1→6 L-fucose | 015 | $5.0 \times 10^5$ | $4.9 \times 10^4$ | $9.1 \times 10^4$ | $1.3 \times 10^5$ | $5.6 \times 10^4$ | $1.2 \times 10^5$ |
| | 201 | $4.6 \times 10^5$ | $6.4 \times 10^4$ | $5.1 \times 10^4$ | $1.2 \times 10^5$ | $5.0 \times 10^5$ | $1.0 \times 10^5$ |
| | 202 | $4.0 \times 10^5$ | $6.1 \times 10^4$ | $5.4 \times 10^4$ | $1.2 \times 10^5$ | $1.1 \times 10^5$ | $4.4 \times 10^4$ |
| | 203 | $3.3 \times 10^5$ | $5.2 \times 10^4$ | $6.6 \times 10^4$ | $1.3 \times 10^5$ | $7.3 \times 10^4$ | $2.5 \times 10^4$ |
| | 401 | $3.5 \times 10^5$ | $5.7 \times 10^4$ | $5.5 \times 10^4$ | $1.4 \times 10^5$ | $4.2 \times 10^4$ | $9.2 \times 10^4$ |
| | 402 | $2.0 \times 10^5$ | $4.4 \times 10^4$ | $1.1 \times 10^4$ | $1.6 \times 10^5$ | $5.9 \times 10^4$ | $4.8 \times 10^4$ |
| | 403 | $3.4 \times 10^5$ | $5.6 \times 10^4$ | $5.2 \times 10^4$ | $1.3 \times 10^5$ | $9.9 \times 10^4$ | $3.8 \times 10^4$ |
| | 404 | $3.9 \times 10^5$ | $5.8 \times 10^4$ | $6.5 \times 10^4$ | $1.5 \times 10^5$ | $5.8 \times 10^4$ | $4.5 \times 10^4$ |
| | 405 | $3.2 \times 10^5$ | $5.4 \times 10^4$ | $5.6 \times 10^4$ | $1.3 \times 10^5$ | $4.7 \times 10^4$ | $3.6 \times 10^4$ |
| | 406 | $2.2 \times 10^5$ | $3.8 \times 10^4$ | $4.7 \times 10^4$ | $1.1 \times 10^5$ | $1.8 \times 10^4$ | $1.3 \times 10^4$ |
| | 407 | $2.8 \times 10^5$ | $1.0 \times 10^4$ | $4.5 \times 10^4$ | $1.1 \times 10^5$ | $1.0 \times 10^3$ | $<1.0 \times 10^3$ |
| | 410 | $2.2 \times 10^5$ | $3.9 \times 10^4$ | $3.8 \times 10^4$ | $1.0 \times 10^5$ | $<1.0 \times 10^3$ | $<1.0 \times 10^3$ |
| | 413 | $2.8 \times 10^5$ | $1.0 \times 10^4$ | $3.2 \times 10^4$ | $7.9 \times 10^4$ | $<1.0 \times 10^3$ | $<1.0 \times 10^3$ |
| | 418 | $2.2 \times 10^5$ | $4.3 \times 10^3$ | $<1.0 \times 10^3$ | $6.3 \times 10^4$ | $<1.0 \times 10^3$ | $<1.0 \times 10^3$ |
| | 601 | $2.4 \times 10^5$ | $1.0 \times 10^4$ | $6.1 \times 10^4$ | $1.4 \times 10^5$ | $3.0 \times 10^4$ | $3.1 \times 10^4$ |
| | 602 | $1.2 \times 10^5$ | $3.2 \times 10^4$ | $5.2 \times 10^4$ | $1.4 \times 10^5$ | $2.4 \times 10^4$ | $2.9 \times 10^4$ |

TABLE 5

| | Sugar chain No. | Example 1 PTL ($M^{-1}$) | Example 2 SRL ($M^{-1}$) | Comparison Example 1 AAL ($M^{-1}$) | Comparison Example 2 AOL ($M^{-1}$) | Comparison Example 3 LCA ($M^{-1}$) | Comparison Example 4 PSA ($M^{-1}$) |
|---|---|---|---|---|---|---|---|
| Sugar chain having L-fucose other than α1→6 L-fucose | 419 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 420 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 718 | $<1.0 \times 10^3$ | $<1.0 \times 10^3$ | $6.5 \times 10^4$ | $1.7 \times 10^5$ | $<1.0 \times 10^3$ | $<1.0 \times 10^3$ |
| | 719 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 720 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 721 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 722 | $<1.0 \times 10^3$ | $<1.0 \times 10^3$ | $<1.0 \times 10^3$ | $5.6 \times 10^4$ | $<1.0 \times 10^3$ | $<1.0 \times 10^3$ |

TABLE 5-continued

| Sugar chain No. | Example 1 PTL ($M^{-1}$) | Example 2 SRL ($M^{-1}$) | Comparison Example 1 AAL ($M^{-1}$) | Comparison Example 2 AOL ($M^{-1}$) | Comparison Example 3 LCA ($M^{-1}$) | Comparison Example 4 PSA ($M^{-1}$) |
|---|---|---|---|---|---|---|
| 723 | $<1.0 \times 10^3$ | $<1.0 \times 10^3$ | $3.5 \times 10^4$ | $<1.0 \times 10^3$ | $<1.0 \times 10^3$ | $<1.0 \times 10^3$ |
| 726 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 727 | $<1.0 \times 10^3$ | $<1.0 \times 10^3$ | $1.3 \times 10^5$ | $7.6 \times 10^4$ | $<1.0 \times 10^3$ | $<1.0 \times 10^3$ |
| 728 | $<1.0 \times 10^3$ | $<1.0 \times 10^3$ | $<1.0 \times 10^3$ | $1.2 \times 10^4$ | $<1.0 \times 10^3$ | $<1.0 \times 10^3$ |
| 729 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 730 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 731 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 739 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 909 | $<1.0 \times 10^3$ | $<1.0 \times 10^3$ | $3.1 \times 10^5$ | $4.4 \times 10^4$ | $<1.0 \times 10^3$ | $<1.0 \times 10^3$ |
| 910 | $<1.0 \times 10^3$ | $<1.0 \times 10^3$ | $9.0 \times 10^4$ | $5.6 \times 10^4$ | $<1.0 \times 10^3$ | $<1.0 \times 10^3$ |
| 931 | $<1.0 \times 10^3$ | $<1.0 \times 10^3$ | $<1.0 \times 10^3$ | $9.9 \times 10^4$ | $<1.0 \times 10^3$ | $<1.0 \times 10^3$ |
| 932 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| 933 | $<1.0 \times 10^3$ | $<1.0 \times 10^3$ | $2.1 \times 10^5$ | $3.1 \times 10^4$ | $<1.0 \times 10^3$ | $<1.0 \times 10^3$ |

TABLE 6

| | Sugar chain No. | Example 1 PTL ($M^{-1}$) | Example 2 SRL ($M^{-1}$) | Comparison Example 1 AAL ($M^{-1}$) | Comparison Example 2 AOL ($M^{-1}$) | Comparison Example 3 LCA ($M^{-1}$) | Comparison Example 4 PSA ($M^{-1}$) |
|---|---|---|---|---|---|---|---|
| Sugar chain not having L-fucose | 001 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 002 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 003 | $<1.0 \times 10^3$ | $<1.0 \times 10^3$ | $<1.0 \times 10^3$ | $<1.0 \times 10^3$ | $7.2 \times 10^3$ | $7.8 \times 10^3$ |
| | 004 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 005 | $<1.0 \times 10^3$ | $<1.0 \times 10^3$ | $<1.0 \times 10^3$ | $<1.0 \times 10^3$ | $7.3 \times 10^3$ | $7.4 \times 10^3$ |
| | 006 | $<1.0 \times 10^3$ | $<1.0 \times 10^3$ | $<1.0 \times 10^3$ | $<1.0 \times 10^3$ | $1.4 \times 10^4$ | $7.1 \times 10^3$ |
| | 007 | $<1.0 \times 10^3$ | $<1.0 \times 10^3$ | $<1.0 \times 10^3$ | $<1.0 \times 10^3$ | $<1.0 \times 10^3$ | $7.8 \times 10^3$ |
| | 008 | $<1.0 \times 10^3$ | $<1.0 \times 10^3$ | $<1.0 \times 10^3$ | $6.9 \times 10^4$ | $1.8 \times 10^4$ | $1.0 \times 10^4$ |
| | 009 | $<1.0 \times 10^3$ | $<1.0 \times 10^3$ | $<1.0 \times 10^3$ | $<1.0 \times 10^3$ | $1.8 \times 10^4$ | $7.9 \times 10^3$ |
| | 010 | $<1.0 \times 10^3$ | $<1.0 \times 10^3$ | $<1.0 \times 10^3$ | $<1.0 \times 10^3$ | $1.3 \times 10^4$ | $<1.0 \times 10^3$ |
| | 011 | $<1.0 \times 10^3$ | $<1.0 \times 10^3$ | $<1.0 \times 10^3$ | $<1.0 \times 10^3$ | $1.4 \times 10^4$ | $<1.0 \times 10^3$ |
| | 012 | $<1.0 \times 10^3$ | $<1.0 \times 10^3$ | $<1.0 \times 10^3$ | $<1.0 \times 10^3$ | $2.5 \times 10^4$ | $1.7 \times 10^4$ |
| | 013 | $<1.0 \times 10^3$ | $<1.0 \times 10^3$ | $<1.0 \times 10^3$ | $<1.0 \times 10^3$ | $1.7 \times 10^4$ | $<1.0 \times 10^3$ |
| | 014 | $<1.0 \times 10^3$ | $<1.0 \times 10^3$ | $<1.0 \times 10^3$ | $<1.0 \times 10^3$ | $1.7 \times 10^4$ | $8.6 \times 10^3$ |
| | 101 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 103 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 104 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 105 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 107 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 108 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 301 | $<1.0 \times 10^3$ | $<1.0 \times 10^3$ | $<1.0 \times 10^3$ | $1.8 \times 10^4$ | $<1.0 \times 10^3$ | $<1.0 \times 10^3$ |
| | 304 | $<1.0 \times 10^3$ | $<1.0 \times 10^3$ | $<1.0 \times 10^3$ | $2.0 \times 10^4$ | $<1.0 \times 10^3$ | $<1.0 \times 10^3$ |
| | 305 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 307 | $<1.0 \times 10^3$ | $<1.0 \times 10^3$ | $<1.0 \times 10^3$ | $<1.0 \times 10^3$ | $<1.0 \times 10^3$ | $2.4 \times 10^3$ |
| | 308 | $<1.0 \times 10^3$ | $<1.0 \times 10^3$ | $<1.0 \times 10^3$ | $2.0 \times 10^4$ | $<1.0 \times 10^3$ | $<1.0 \times 10^3$ |
| | 313 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 314 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 323 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 501 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 502 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 503 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 504 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |

TABLE 7

| | Sugar chain No. | Example 1 PTL ($M^{-1}$) | Example 2 SRL ($M^{-1}$) | Comparison Example 1 AAL ($M^{-1}$) | Comparison Example 2 AOL ($M^{-1}$) | Comparison Example 3 LCA ($M^{-1}$) | Comparison Example 4 PSA ($M^{-1}$) |
|---|---|---|---|---|---|---|---|
| Sugar chain not having L-fucose | 701 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 702 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 703 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 704 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 705 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 706 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 707 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 708 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |
| | 709 | $<1.0 \times 10^3$ | $<1.0 \times 10^3$ | $<1.0 \times 10^3$ | $<1.0 \times 10^3$ | $<1.0 \times 10^3$ | $<1.0 \times 10^3$ |

TABLE 7-continued

| Sugar chain No. | Example 1 PTL ($M^{-1}$) | Example 2 SRL ($M^{-1}$) | Comparison Example 1 AAL ($M^{-1}$) | Comparison Example 2 AOL ($M^{-1}$) | Comparison Example 3 LCA ($M^{-1}$) | Comparison Example 4 PSA ($M^{-1}$) |
|---|---|---|---|---|---|---|
| 710 | <1.0 × 10³ | <1.0 × 10³ | <1.0 × 10³ | <1.0 × 10³ | <1.0 × 10³ | <1.0 × 10³ |
| 711 | <1.0 × 10³ | <1.0 × 10³ | <1.0 × 10³ | <1.0 × 10³ | <1.0 × 10³ | <1.0 × 10³ |
| 712 | <1.0 × 10³ | <1.0 × 10³ | <1.0 × 10³ | <1.0 × 10³ | <1.0 × 10³ | <1.0 × 10³ |
| 713 | <1.0 × 10³ | <1.0 × 10³ | <1.0 × 10³ | <1.0 × 10³ | <1.0 × 10³ | <1.0 × 10³ |
| 715 | <1.0 × 10³ | <1.0 × 10³ | <1.0 × 10³ | <1.0 × 10³ | <1.0 × 10³ | <1.0 × 10³ |
| 716 | <1.0 × 10³ | <1.0 × 10³ | <1.0 × 10³ | <1.0 × 10³ | <1.0 × 10³ | <1.0 × 10³ |
| 717 | <1.0 × 10³ | <1.0 × 10³ | <1.0 × 10³ | <1.0 × 10³ | <1.0 × 10³ | <1.0 × 10³ |
| 724 | <1.0 × 10³ | <1.0 × 10³ | <1.0 × 10³ | <1.0 × 10³ | <1.0 × 10³ | <1.0 × 10³ |
| 725 | <1.0 × 10³ | <1.0 × 10³ | <1.0 × 10³ | <1.0 × 10³ | <1.0 × 10³ | <1.0 × 10³ |
| 728 | <1.0 × 10³ | <1.0 × 10³ | <1.0 × 10³ | <1.0 × 10³ | <1.0 × 10³ | <1.0 × 10³ |
| 732 | <1.0 × 10³ | <1.0 × 10³ | <1.0 × 10³ | <1.0 × 10³ | <1.0 × 10³ | <1.0 × 10³ |
| 733 | <1.0 × 10³ | <1.0 × 10³ | <1.0 × 10³ | <1.0 × 10³ | <1.0 × 10³ | <1.0 × 10³ |
| 734 | <1.0 × 10³ | <1.0 × 10³ | <1.0 × 10³ | <1.0 × 10³ | <1.0 × 10³ | <1.0 × 10³ |
| 735 | <1.0 × 10³ | <1.0 × 10³ | <1.0 × 10³ | <1.0 × 10³ | <1.0 × 10³ | <1.0 × 10³ |
| 736 | <1.0 × 10³ | <1.0 × 10³ | <1.0 × 10³ | <1.0 × 10³ | <1.0 × 10³ | <1.0 × 10³ |
| 737 | <1.0 × 10³ | <1.0 × 10³ | <1.0 × 10³ | <1.0 × 10³ | <1.0 × 10³ | <1.0 × 10³ |
| 738 | <1.0 × 10³ | <1.0 × 10³ | <1.0 × 10³ | <1.0 × 10³ | <1.0 × 10³ | <1.0 × 10³ |
| 901 | <1.0 × 10³ | <1.0 × 10³ | <1.0 × 10³ | <1.0 × 10³ | <1.0 × 10³ | <1.0 × 10³ |
| 902 | <1.0 × 10³ | <1.0 × 10³ | <1.0 × 10³ | <1.0 × 10³ | <1.0 × 10³ | <1.0 × 10³ |
| 903 | <1.0 × 10³ | <1.0 × 10³ | <1.0 × 10³ | <1.0 × 10³ | <1.0 × 10³ | <1.0 × 10³ |
| 905 | <1.0 × 10³ | <1.0 × 10³ | <1.0 × 10³ | <1.0 × 10³ | <1.0 × 10³ | <1.0 × 10³ |
| 906 | <1.0 × 10³ | <1.0 × 10³ | <1.0 × 10³ | <1.0 × 10³ | <1.0 × 10³ | <1.0 × 10³ |
| 907 | <1.0 × 10³ | <1.0 × 10³ | <1.0 × 10³ | <1.0 × 10³ | <1.0 × 10³ | <1.0 × 10³ |

As can be seen from Tables 4 to 7, AAL of Comparison Example 1 and AOL of Comparison Example 2 are bound to non-α1→6 glycolipid-base L-fucose sugar chains (sugar chain Nos. 718, 722, 723, 727, 909, 910, and 933) as well as L-fucose α1→6 sugar chains (sugar chain Nos. 15, 201-203, and 401-418). LCA of Comparison Example 3 and PSA of Comparison Example 4 are bound to a lot of sugar chains not having L-fucose α1→6 sugar chains (sugar chains Nos. 003, 005-014). On the other hand, PTL of Example 1 and SRL of Example 2 are securely bound to an L-fucose α1→6 sugar chain and are not bound to a non-L-fucose α1→6 sugar chain and a sugar chain not having L-fucose at all. Furthermore, PTL of Example 1 has a higher association constant than that of a conventional lectin (association constant of Ka=1.0× $10^5 M^{-1}$ or more). Furthermore, PTL of Example 1 and SRL of Example 2 are also strongly bound to the core-fucosylated triantennary N-glycans (sugar chain Nos. 407-413) and tetraantennary N-glycan (sugar chain No. 418). Even those added with sialic acid (sugar chains No. 601 and 602), it can be seen that association constant of the L-fucose α1→6 sugar chain is not lowered.

(6) Detection of Glycoprotein Using PTL and SRL (i) Preparation of Glycoprotein

Glycoproteins (1) to (9) having the following main sugar chain structures and (10) bovine serum albumin having no sugar were prepared.

(1) As glycoprotein having L-fucose α1→6 N-linked glycans, thyroglobulin (pig) having the following formula:

[Chemical formula 3]

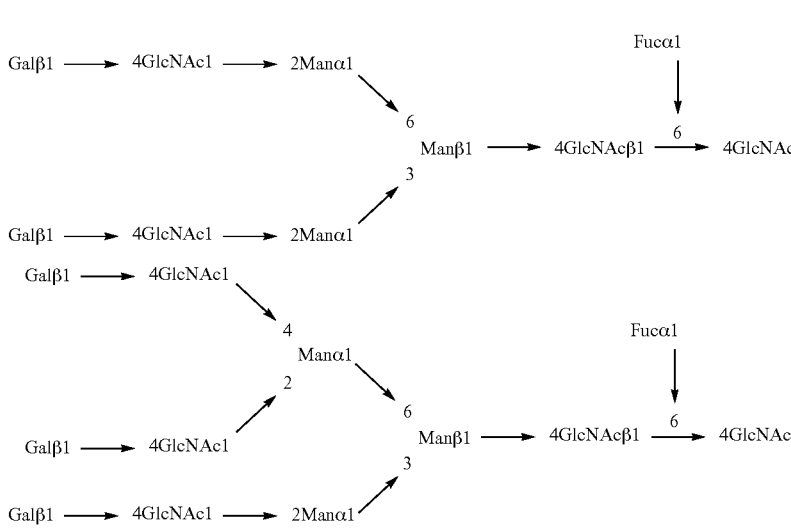

(2) As glycoprotein having L-fucose α1→6 N-linked glycans, lactoferrin (bovine) having the following formula:

[Chemical formula 4]

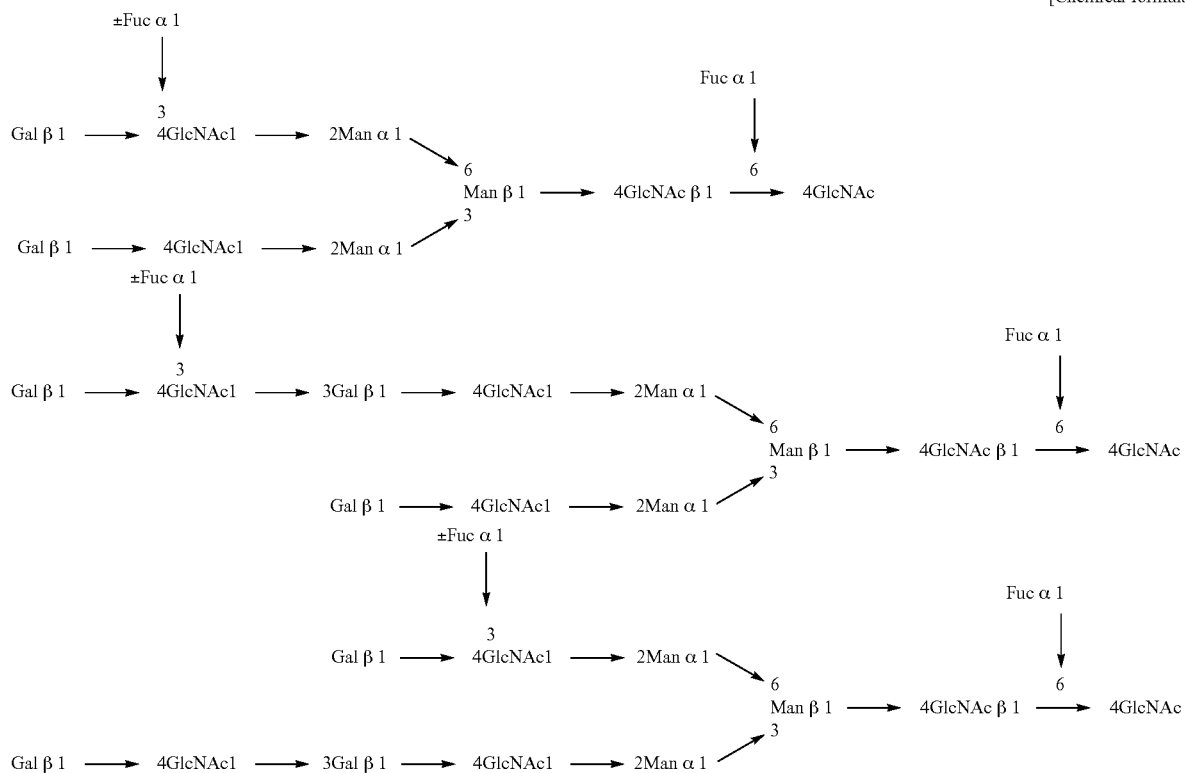

(3) As glycoprotein having L-fucose α1→6 N-linked glycans, immune globulin G (human) having the following formula:

[Chemical formula 5]

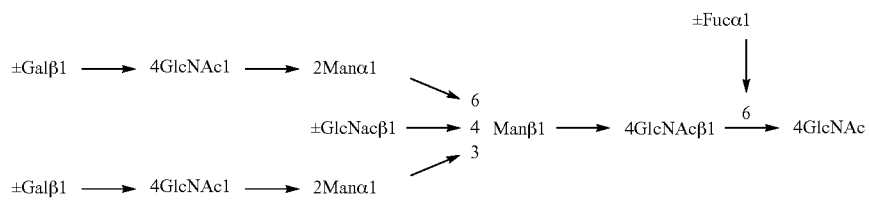

(4) As glycoprotein not having L-fucose α1→6 N-linked glycans, transferrin (human) having the following formula:

[Chemical formula 6]

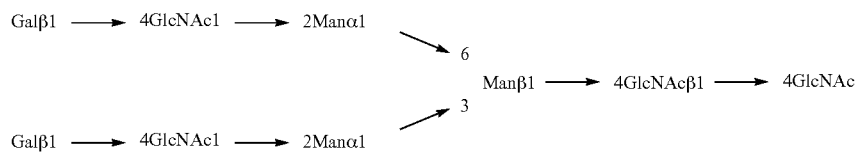

(5) As glycoprotein not having L-fucose α1→6 N-linked glycans, α1-acidic glycoprotein (human) having the following formula:

[Chemical formula 7]
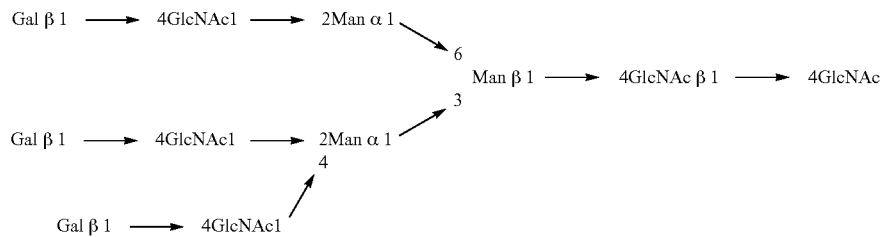
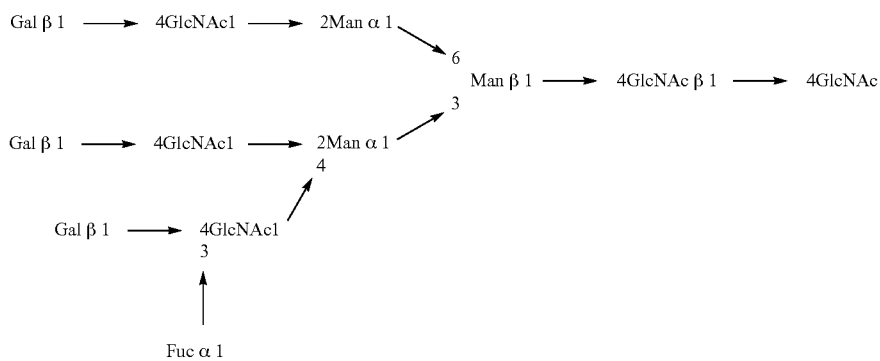
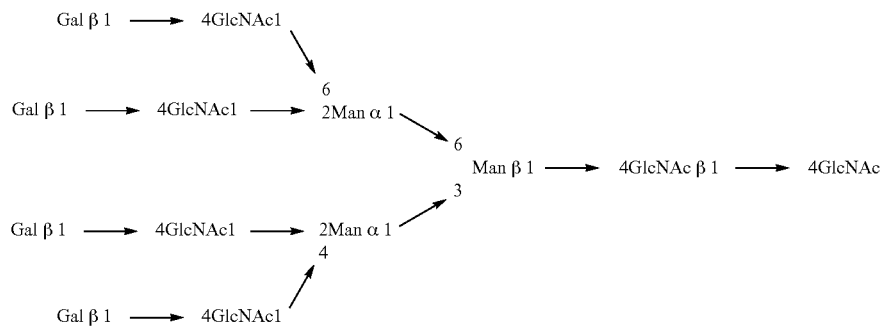
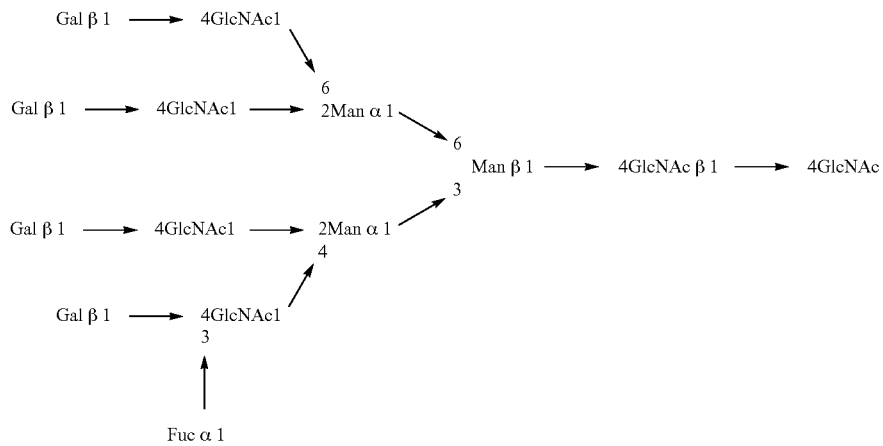

(6) As glycoprotein having high mannose-type sugar chains, invertase (yeast) having the following formula:

[Chemical formula 8]

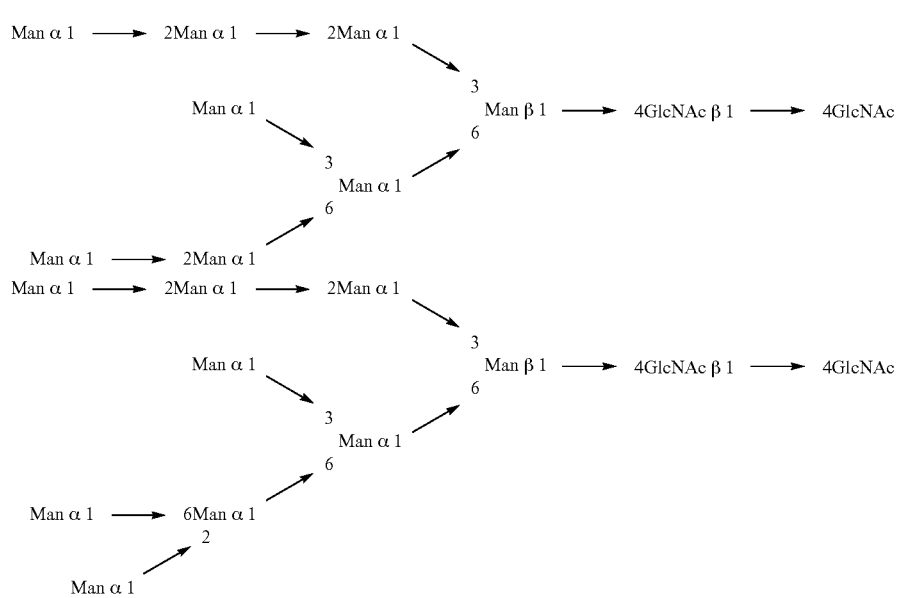

(7) As glycoprotein having L-fucose O-linked sugar chains, mucin (pig) having the following formula:

[Chemical formula 9]

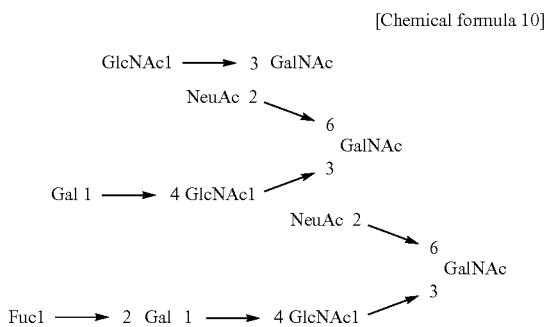

(8) As glycoprotein having L-fucose O-linked sugar chains, mucin (bovine) having the following formula:

[Chemical formula 10]

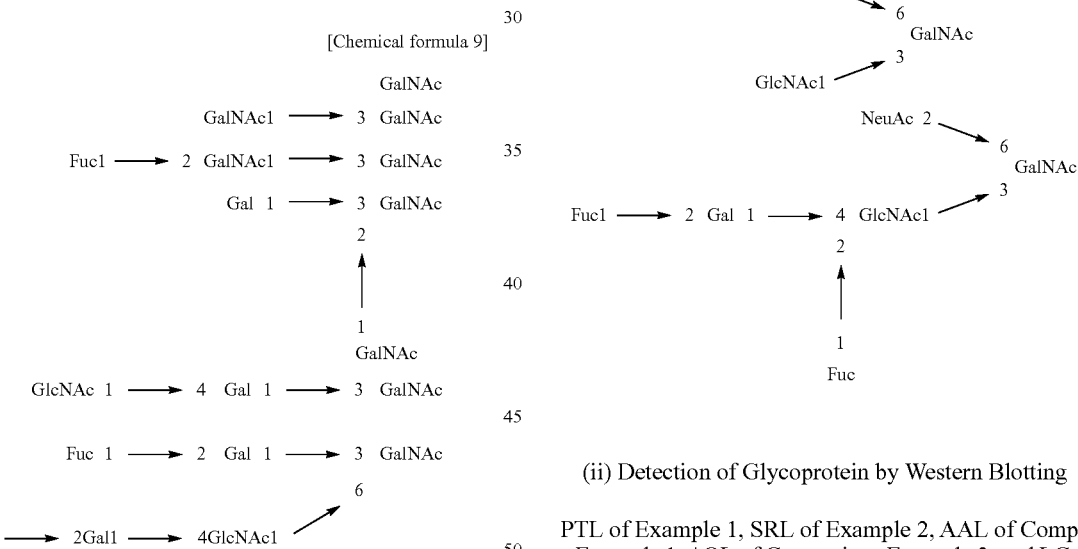

(ii) Detection of Glycoprotein by Western Blotting

PTL of Example 1, SRL of Example 2, AAL of Comparison Example 1, AOL of Comparison Example 2, and LCA of Comparison Example 3 all subjected to biotin-labeling.

(Biotinylation of Lectin)

Lectin was measured and was dissolved in 0.1 M sodium hydrogen carbonate solution (5 mg/ml). Then, a biotinylation reagent was dissolved in dimethyl sulfoxide and the resultant solution was added to lectin solution to cause reaction therebetween. Then, the reactant was distilled and lyophilized, thereby obtain biotin-labeled lectin.

(SDS-Page and Blotting of Glycoprotein)

The solution obtained by dissolving the glycoprotein sample in 10 mM phosphate buffered saline (pH 7.4, PBS) at 2 mg/ml was dispensed to a microtube by a unit of 18 μl. 6 μl of SDS process liquid (Sample Buffer Solution (2ME−); Wako Pure Chemical Industries, Ltd.) and 1.25 μl of 2-mercaptoethanol (Bio-Rad Laboratories, Inc.) was added to each dispensed fluid and the resultant mixture was boiled for 5 minutes. These were demonstrated by polyacrylamide gel and transferred to PVDF membranes (Immobilon IPVH 304 F0, Millipore K.K.).

(Staining by Biotin-Labeled Lectin)

Figure 17:
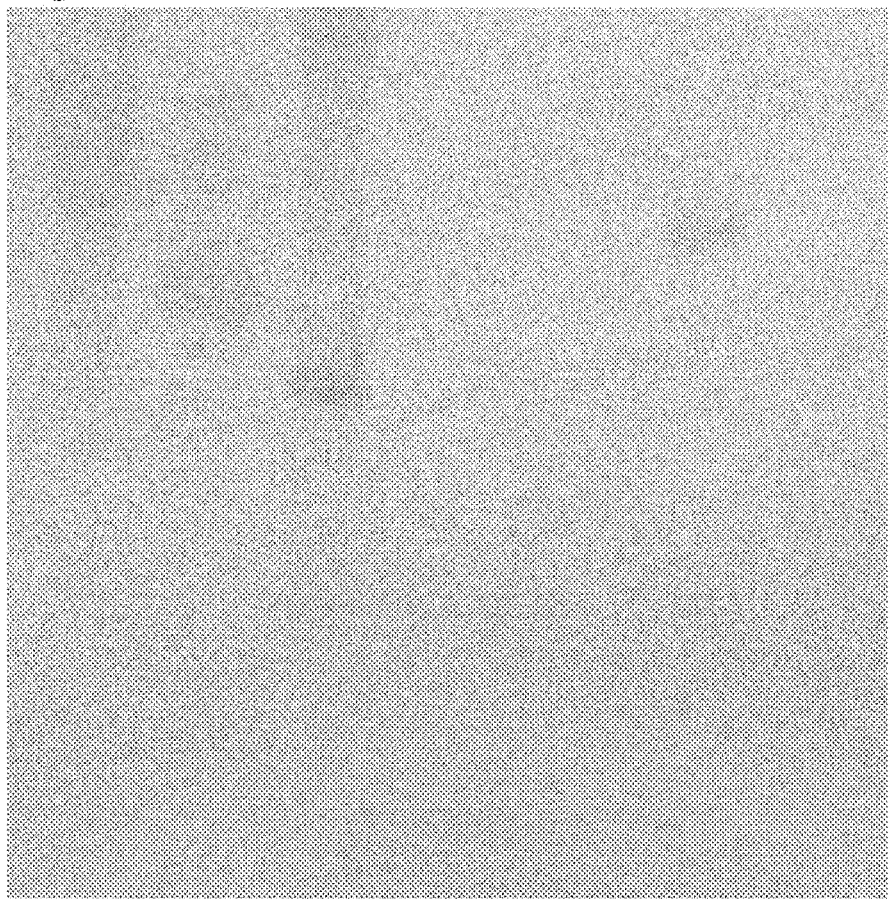
FIG. 17 illustrates the result of Western blotting using LCA of Comparison Example 3 (a photograph as a substitute of a drawing).

The film was immersed in 10 mM Tris buffer solution including 0.8% NaCl added with 1% BSA (pH 7.4, 1% BSA+TBS) and was shaken at a room temperature for one hour. Then, the film was cleaned three times by 10 mM Tris buffer solution (pH 7.4, TBS) including 0.8% NaCl. Then, the film was immersed in biotin-labeled lectin solution (2 µg/ml) and was shaken at a room temperature for one hour. Then, the film was cleaned three times by TBS. Then, the film was immersed in the HRP label streptavidin solution at 1 µg/ml (Vector Laboratories) and was shaken at a room temperature for 30 minutes. After the film was cleaned three times by TBS, a POD immunostain set (Wako Pure Chemical Industries, Ltd.) was used to perform a staining test. The staining test is to detect glycoprotein by the western blotting using biotin-labeled lectin. FIG. 13 to FIG. 17 are photographs showing the following glycoproteins stained by PTL (FIG. 13), SRL (FIG. 14), AAL (FIG. 15), AOL (FIG. 16), or LCA (FIG. 17).

In FIG. 13 to FIG. 17, the lanes 0 to 6 correspond to the followings. Lane 1: thyroglobulin, lane 2: lactoferrin, lane 3: immune immunoglobulin, lane 4: transferrin, lane 5: α1-acidic glycoprotein, lane 6: invertase, lane 0: bovine serum albumin (control)

Figure 18:
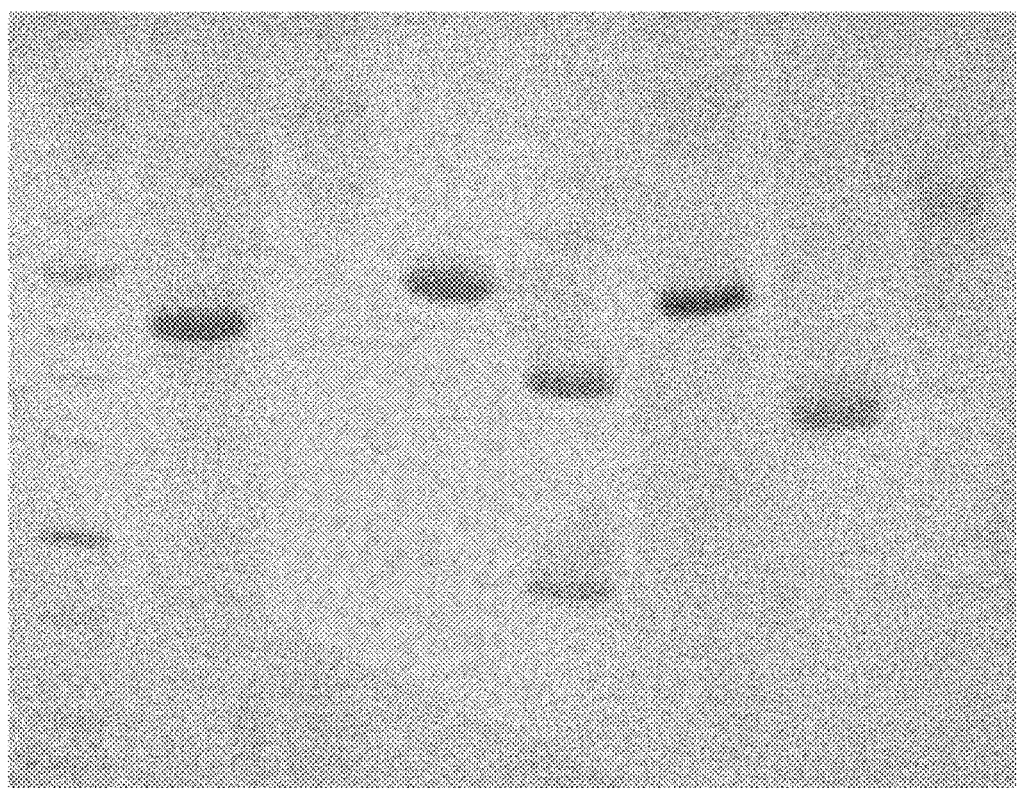
FIG. 18 illustrates the result when only proteins are stained by CBB as a control (a photograph as a substitute of a drawing).
Figure 19:
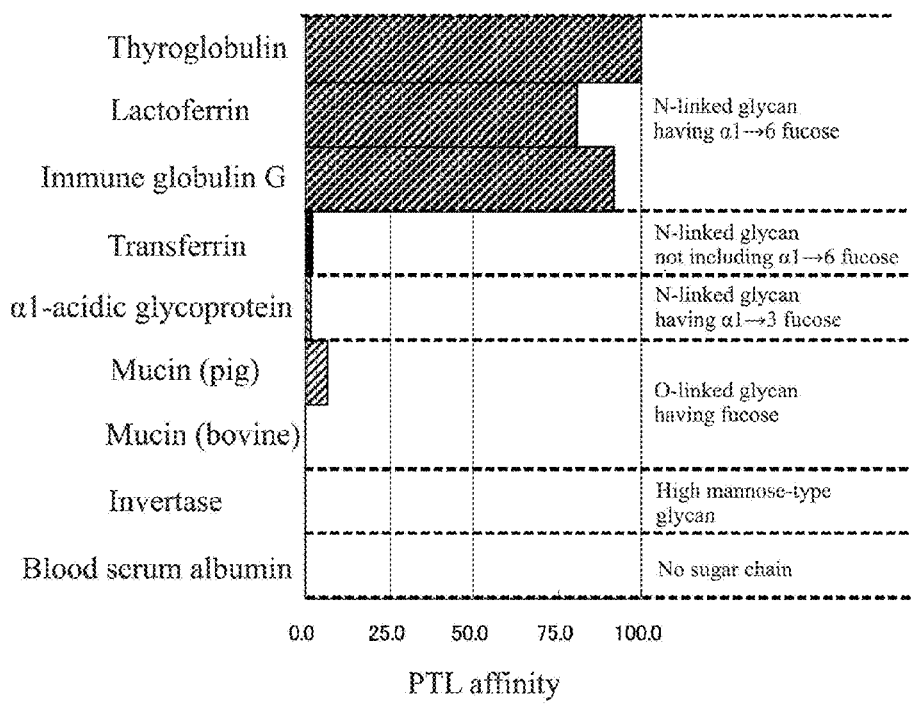
FIG. 19 illustrates the result of glycoproteins detection by ELISA using PTL of Example 1.
Figure 20:
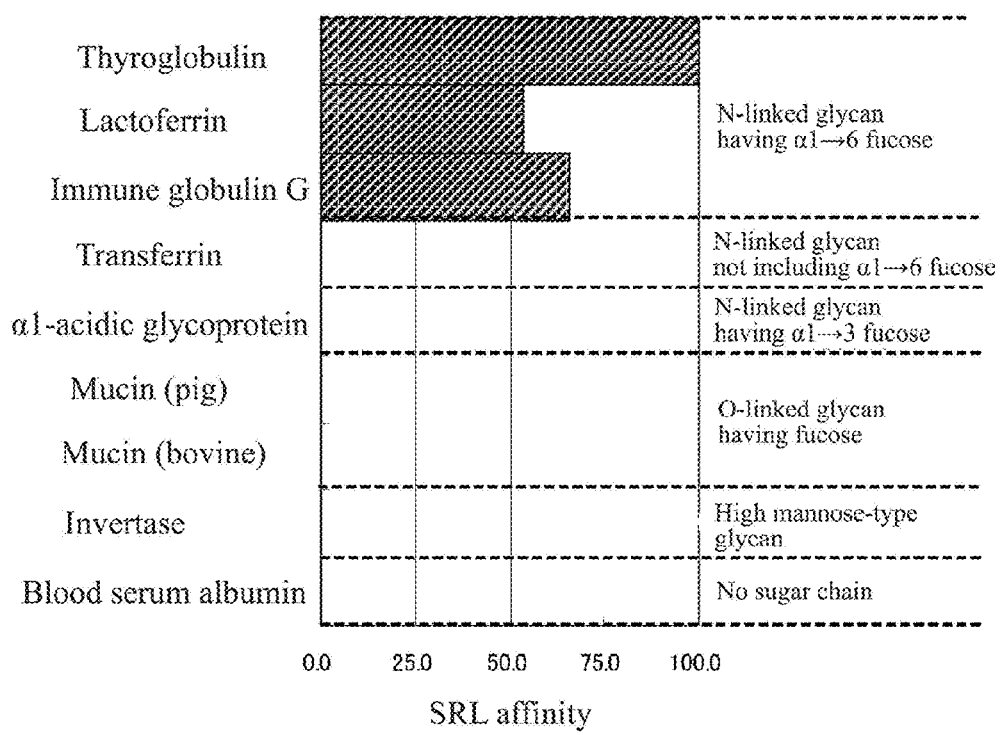
FIG. 20 illustrates the result of glycoproteins detection by ELISA using SRL of Example 2.
Figure 21:
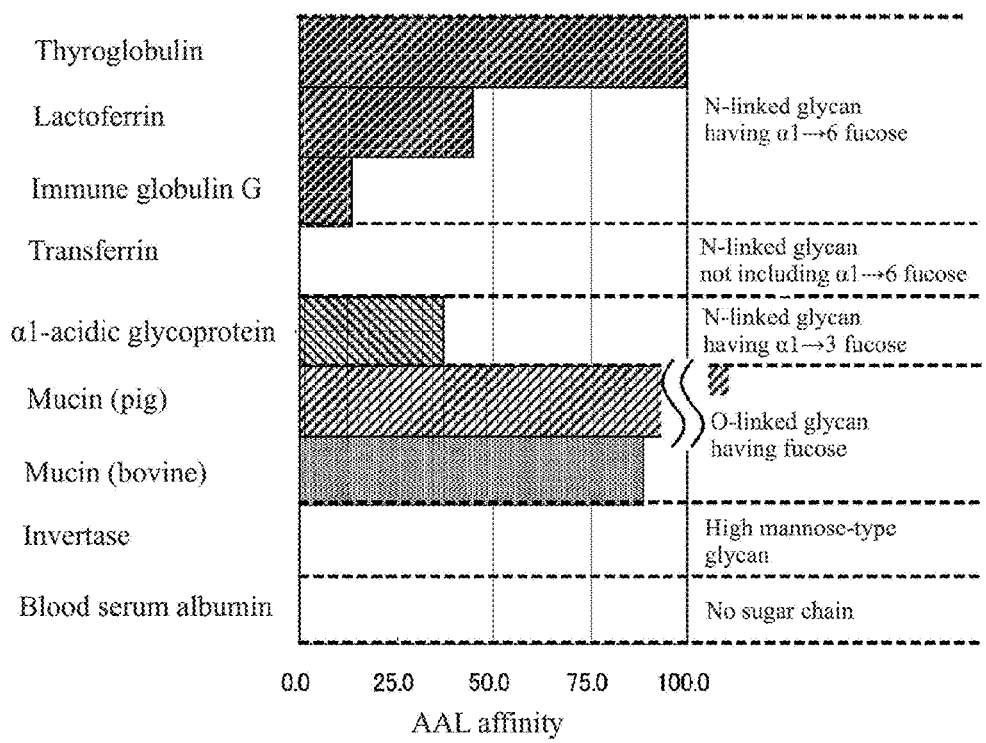
FIG. 21 illustrates the result of glycoproteins detection by ELISA using AAL of Comparison Example 1.
Figure 22:
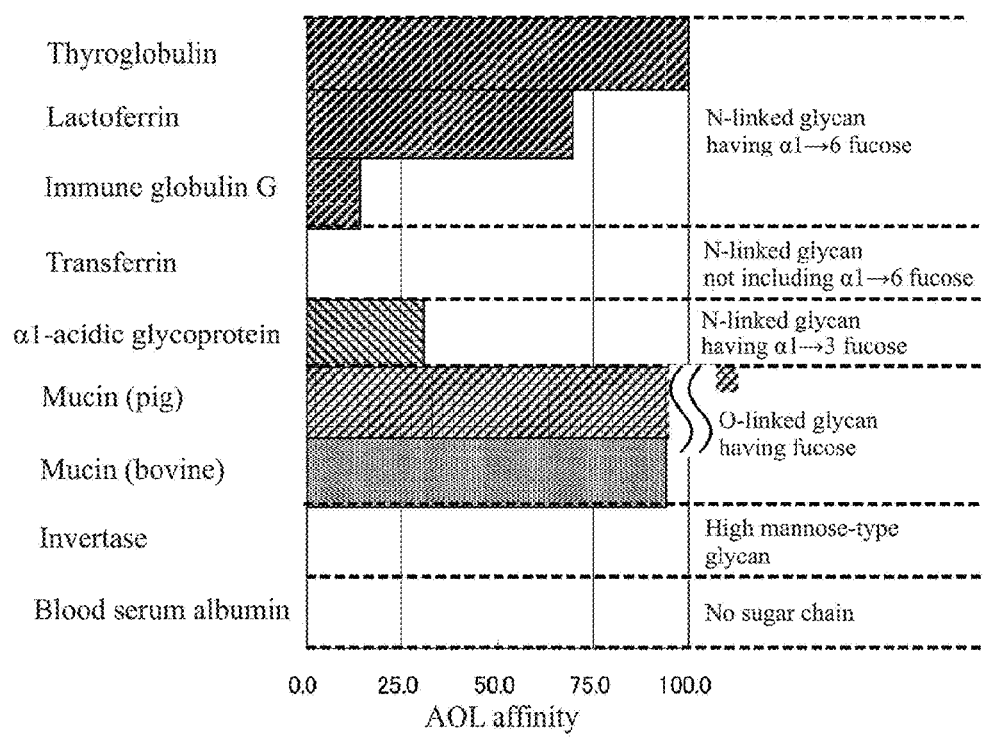
FIG. 22 illustrates the result of glycoproteins detection by ELISA using AOL of Comparison Example 2.
Figure 23:
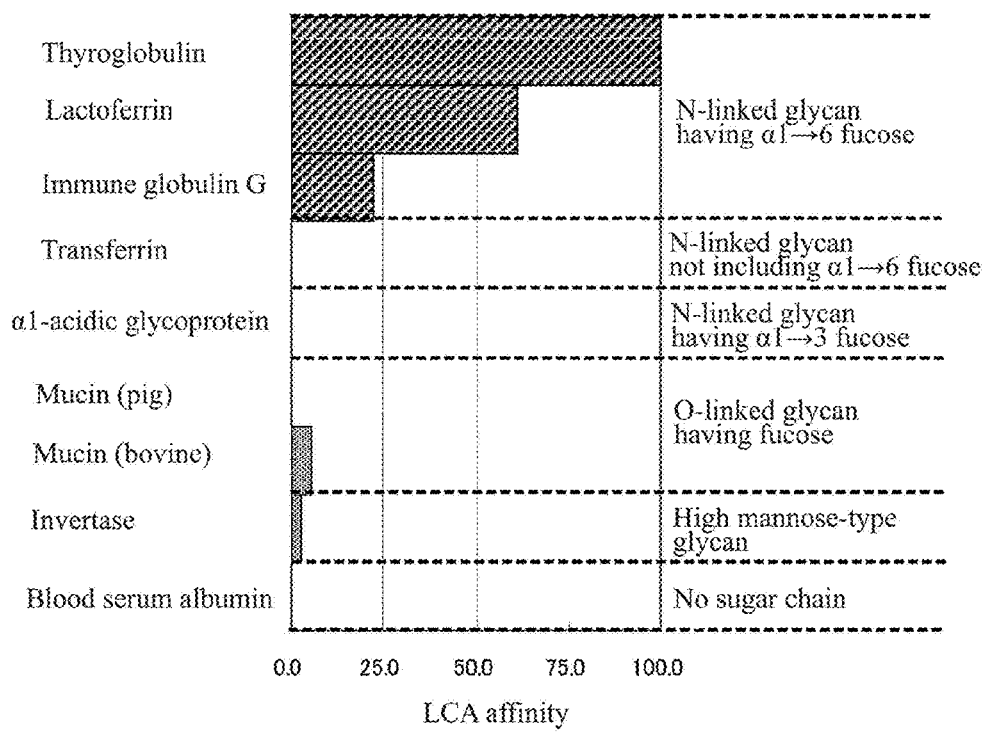
FIG. 23 illustrates the result of glycoproteins detection by ELISA using LCA of Comparison Example 3.
Figure 24:
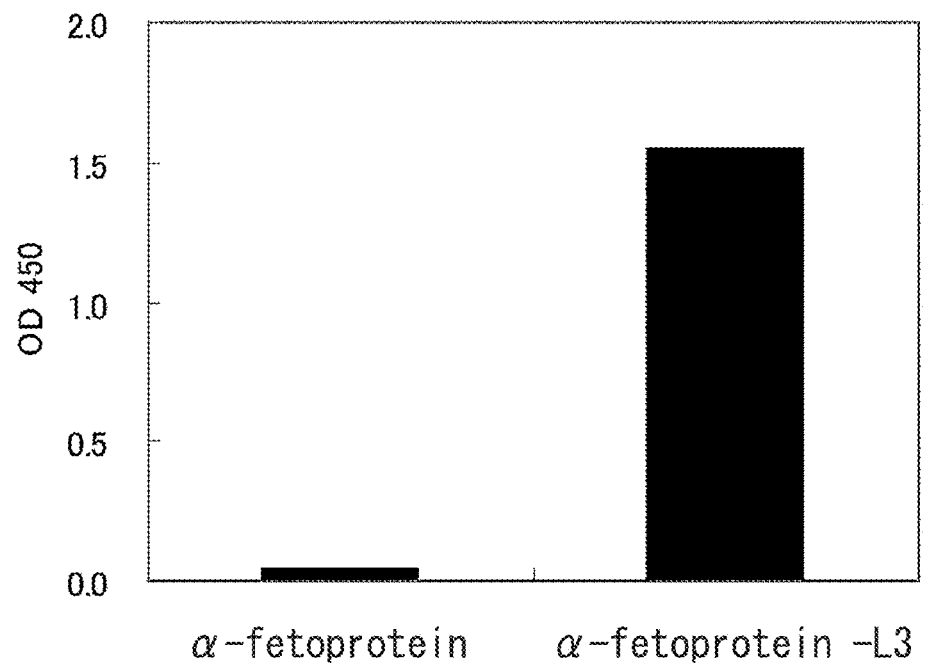
FIG. 24 illustrates the detection result of a difference in a sugar chain between α-fetoproteins L1 and L3 by ELISA using PTL of Example 1.
Figure 25:
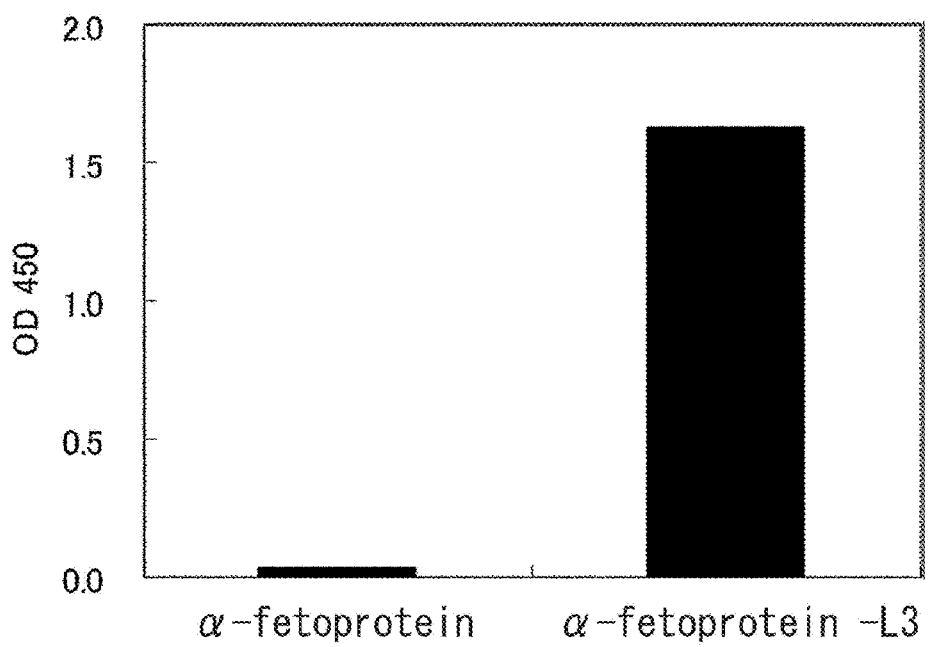
FIG. 25 illustrates the detection result of a difference in a sugar chain between α-fetoproteins L1 and L3 by ELISA using the SRL of Example 2.
Figure 26:
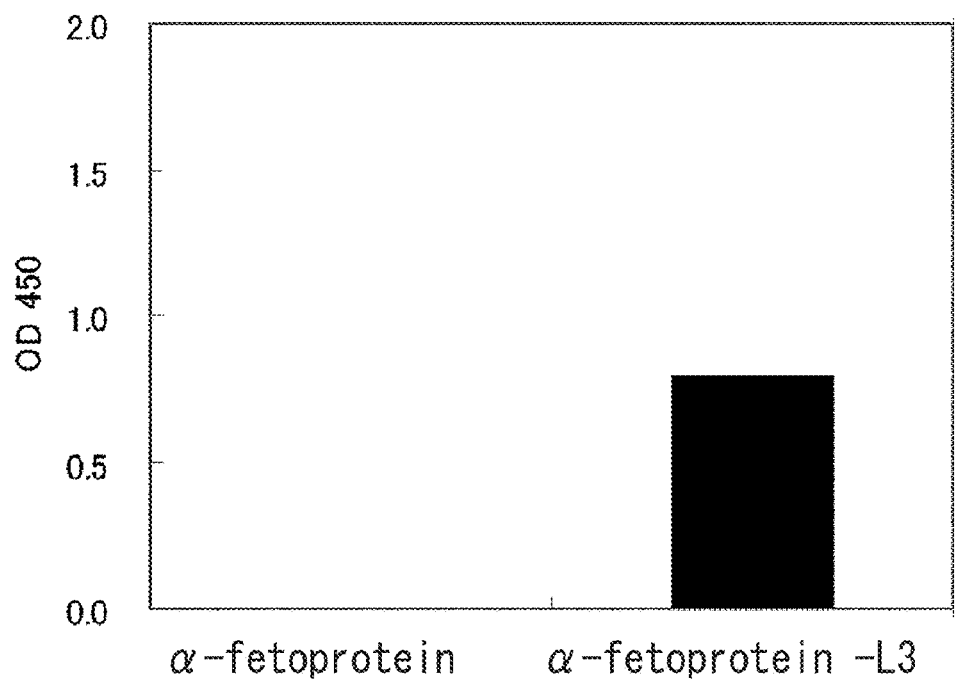
FIG. 26 illustrates the detection result of a difference in a sugar chain between α-fetoproteins L1 and L3 by ELISA using AAL of Comparison Example 1.
Figure 27:
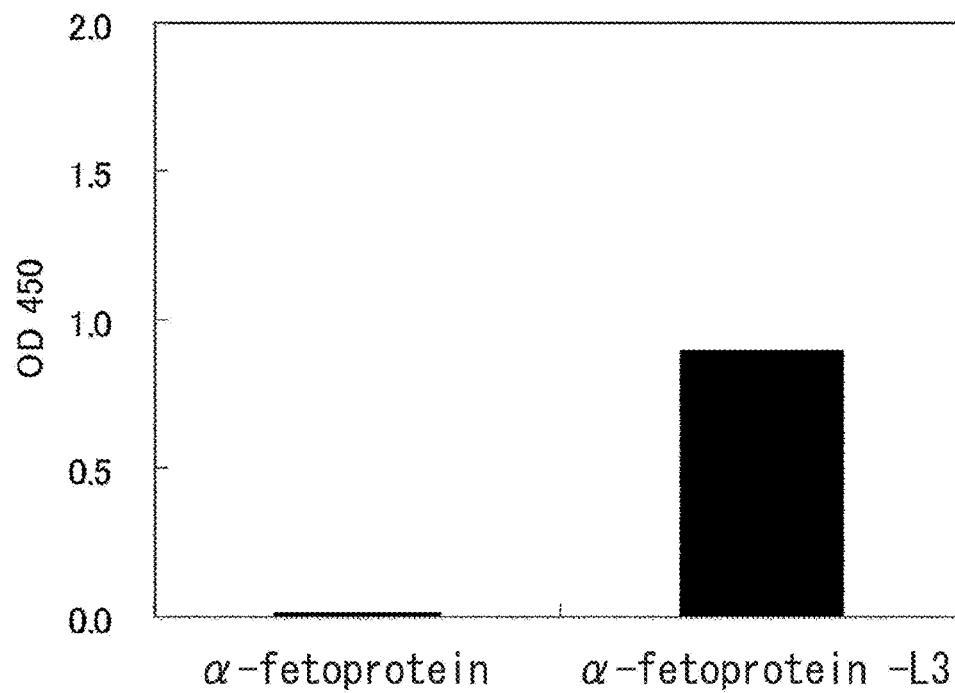
FIG. 27 illustrates the detection result of a difference in a sugar chain between α-fetoproteins L1 and L3 by ELISA using AOL of Comparison Example 2.
Figure 28:
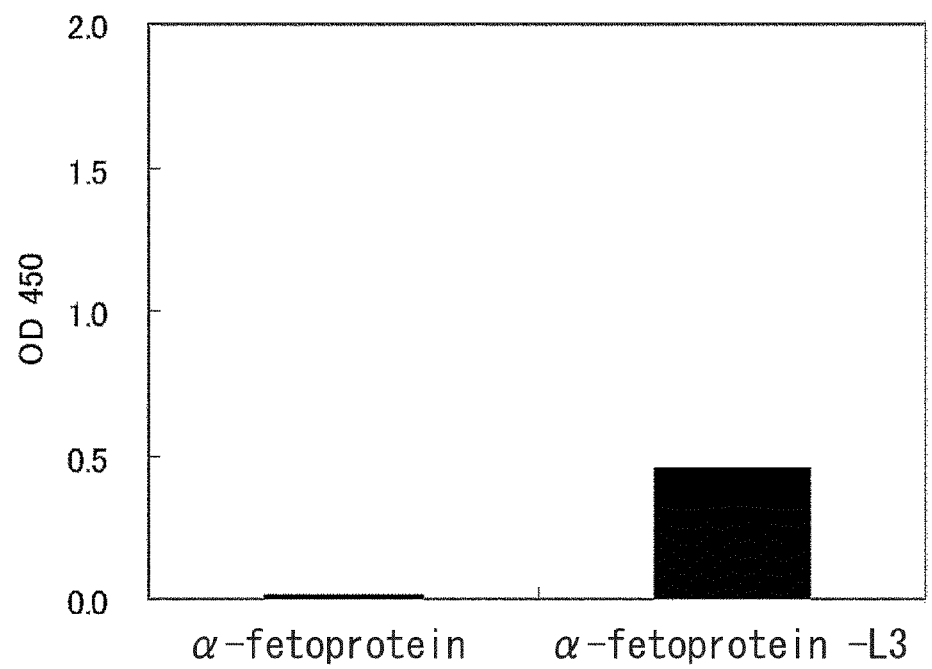
FIG. 28 illustrates the detection result of a difference in a sugar chain between α-fetoproteins L1 and L3 by ELISA using LCA of Comparison Example 3.

For a control, CBB staining was also performed in order to stain protein. The staining photograph thereof is shown in FIG. 18. In FIG. 18, the lanes M and 1 to 6 correspond to the followings. Lane M: molecular weight marker, lane 1: thyroglobulin, lane 2: lactoferrin, lane 3: immunoglobulin G, lane 4: transferrin, lane 5: α1-acidic glycoprotein, lane 6: invertase, lane 0: bovine serum albumin sugar chains and sugar chains not having L-fucose are not detected at all.

(iii) Detection of Glycoproteins by ELISA

PTL of Example 1, SRL of Example 2, AAL of Comparison Example 1, AOL of Comparison Example 2, and LCA of Comparison Example 3 that were biotin-labeled were used to the detection of glycoproteins by the enzyme-linked immunosorbent assay (ELISA).

The glycoprotein and albumin as protein not including a sugar chain as a control were dissolved in 0.1 M carbonic acid buffer solution (pH 9.5) at 1 mg/ml. Then, the resultant solution was added to a microtiter plate (Nunc 439454) and was incubated at 4 degrees C. overnight. Then, the resultant solution was cleaned by 0.05% Tween/PBS three times. Thereafter, 1% BSA/PBS was added to wells and the solution was incubated at 37 degrees C. for one hour. Then, after the solution was cleaned by 0.05% Tween/PBS three times, biotin labeled-lectin appropriately diluted by 1% BSA/0.05% Tween/PBS was added to the wells and the solution was incubated at 37 degrees C. for one hour. After the solution was cleaned by 0.05% Tween/PBS three times, HRP labeled streptavidin solution diluted by 1% BSA/0.05% Tween/PBS was added to wells and the solution was incubated at 37 degrees C. for 30 minutes. After the solution was cleaned by 0.05% Tween/PBS three times, TMB Peroxidase substrate system (KPL) was added and the resultant solution was incubated at a room temperature for 10 minutes while light was being blocked.

The reaction was stopped by 1 M phosphoric acid. Then, a microplate reader (MPR-A4i, TOSOH CORPORATION) was used to measure the absorbance at 450 nm. Based on this value, reaction value ([absorbance at 450 nm of a well for which glycoprotein was solid-phased to the plate and

TABLE 8

| Glycoprotein | Characteristics | Example 1 PTL | Example 2 SRL | Comparison Example 1 AAL | Comparison Example 2 AOL | Comparison Example 3 LCA |
|---|---|---|---|---|---|---|
| (1) Thyroglobulin (pig) | N-linked glycan having α1→6 L-fucose | ○ | ○ | ○ | ○ | ○ |
| (2) Lactoferrin (bovine) | N-linked glycan having α1→6 L-fucose | ○ | ○ | ○ | ○ | ○ |
| (3) Immune-globulin G (human) | N-linked glycan having α1→6 L-fucose | ○ | ○ | ○ | ○ | ○ |
| (4) Transferrin (human) | N-linked glycan not including α1→6 L-fucose | X | X | X | X | X |
| (5) α1-acidic glycoprotein (human) | N-linked glycan having α1→3 L-fucose | X | X | X | X | X |
| (6) Invertase (yeast) | High mannose-type sugar chain | X | X | X | X | ○ |
| (O) Blood serum albumin (bovine) | No sugar chain | X | X | X | X | X |

○ Detected

X Not detected

As can be seen from the results of Table 8 and FIG. 13 to FIG. 18, in the case of LCA of Comparison Example 3, not only glycoprotein having L-fucose α1→6 sugar chains but also glycoprotein having high mannose (invertase) are detected. In contrast with this, in the case of PTL of Example 1 and SRL of Example 2, only glycoprotein having sL-fucose α1→6 sugar chain is detected and a non-L-fucose α1→6 reacted]−[absorbance at 450 nm of a well for which glycoprotein was not solid-phased to the plate and reacted] was calculated. Next, for each lectin, the interaction strength (relative value) to each glycoprotein was calculated based on an assumption that the glycoprotein (thyroglobulin) value was 100%. The calculation result is shown in Table 9 and FIG. 19 to FIG. 23.

TABLE 9

|  | Sugar chains | Example 1 PTL | Example 2 SRL | Comparison Example 1 AAL | Comparison Example 2 AOL | Comparison Example 3 LCA |
|---|---|---|---|---|---|---|
| (1) Thyroglobulin (pig) | N-linked glycan having α1→6 L-fucose | ⊚ | ⊚ | ⊚ | ⊚ | ⊚ |
| (2) Lactoferrin (human) | N-linked glycan chain having α1→6 L-fucose | ⊚ | ○ | ○ | ○ | ○ |
| (3) Immune-globulin G (human) | N-linked glycan having α1→6 L-fucose | ⊚ | ○ | Δ | Δ | ○ |
| (4) Transferrin (human) | N-linked glycan not including α1→6 L-fucose | X | X | X | X | X |
| (5) α1-acidic glycoprotein (human) | N-linked glycan having α1→3 L-fucose | X | X | Δ | Δ | X |
| (6) Invertase (yeast) | High mannose-type glycan | X | X | X | X | X |
| (7) Mucin (pig) | O-linked glycan including L-fucose | X | X | ⊚ | ⊚ | X |
| (8) Mucin (bovine) | O-linked glycan including L-fucose | X | X | ⊚ | ⊚ | X |
| (0) Blood serum albumin (bovine) | No sugar chain | X | X | X | X | X |

⊚ Relative values of 120 to 80
○ Relative values of 80 to 50
Δ Relative values of 50 to 10
X Relative values of 10 or less As can be seen from Table 9 and FIG. 19 to FIG. 23, in the case of AAL of Comparison Example 1 and AOL of Comparison Example 2, not only glycoprotein having L-fucose α1→6 sugar chains but also an O-linked sugar chains (mucin) were undesirably detected. In contrast with this, in the case of PTL of Example 1 and SRL of Example 2, only glycoprotein having L-fucose α1→6 sugar chains is detected and none of non-L-fucose α1→6 sugar chains and a sugar chain not having L-fucose is detected. Furthermore, the lectins of Comparison Examples 1 to 3 have such an interaction strength to lactoferrin and immuneglobulin G (IgG) that is inferior to that of thyroglobulin. In contrast with this, the lectins of Examples 1 and 2 provided the same interaction strength to lactoferrin and immune globulin as that of thyroglobulin.

(iv) Detection of Tumor Marker Sugar Chain by ELISA

α-fetoprotein (hereinafter referred to as "AFP") is a glycoprotein included in a blood serum having an N-linked sugar chain. Substantially no AFP exists in the blood serum of a healthy adult. On the other hand, the blood serum of a patient having a benign liver disease has an increased α-fetoprotein L1-type sugar chain (AFP-L1). Furthermore, α-fetoprotein L3-type sugar chain (AFP-L3) is detected in a patient of a liver cancer. Conventionally, the difference in a sugar chain has been measured by LCA and the measurement result has been used for the diagnosis of a liver disease.

[Chemical formula 12]

α-fetoprotein-L1-type (AFP-L1)
Cirrhosis, chronic hepatitis
(also exists in umbilical cord blood)

NeuAc α2 ⟶ 6(3)Gal β1 ⟶ 4GlcNAc1 ⟶ 2Man α1

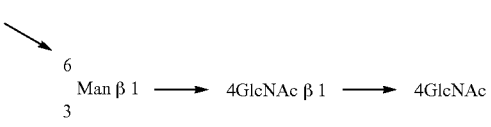

NeuAc α2 ⟶ 6(3)Gal β1 ⟶ 4GlcNAc1 ⟶ 2Man α1

α-fetoprotein-L3-type (AFP-L3)
Liver cancer

NeuAc α2 ⟶ 6(3)Gal β1 ⟶ 4GlcNAc1 ⟶ 2Man α1

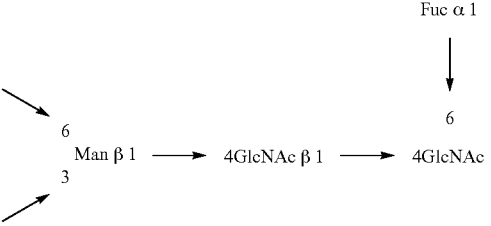

NeuAc α2 ⟶ 6(3)Gal β1 ⟶ 4GlcNAc1 ⟶ 2Man α1

PTL of Example 1, SRL of Example 2, AAL of Comparison Example 1, AOL of Comparison Example 2, and the LCA of Comparison Example 3 that were biotin-labeled were used to evaluate the binding property of α-fetoprotein by ELISA.

0.1 M carbonic acid buffer solution (pH 9.5) was used to dilute α-fetoprotein (derived from human umbilical cord blood serum, mainly L1-type sugar chain) and α-fetoprotein-L3 (prepared from the culture supernatant of human liver cancer cells) so as to achieve 0.01 μg/ml. Then, the resultant solution was added to a microtiter plate (Nunc) and was incubated at 4 degrees C. one night. After the solution was cleaned by 0.05% Tween/PBS three times, 1% BSA/PBS was added to wells and the solution was incubated at 37 degrees C. for one hour. After the solution was washed by 0.05% Tween/PBS three times, the wells were added with the biotin-labeled lectin solution appropriately diluted by 1% BSA/0.05% Tween/PBS and the solution was incubated at 37 degrees C. for one hour. After the solution was cleaned by 0.05% Tween/PBS three times, HRP labeled streptavidin solution diluted by 1% BSA/0.05% Tween/PBS was added and the solution was incubated at 37 degrees C. for 30 minutes. After the solution was cleaned by 0.05% Tween/PBS three times, TMB Peroxidase substrate system (KPL) was added and the resultant solution was incubated at a room temperature for 10 minutes while light was being blocked. The reaction was stopped by 1 M phosphoric acid. Then, a microplate reader (MPR-A4i, TOSOH CORPORATION) was used to measure the absorbance at 450 nm.

The absorbance at 450 nm of the plate on which α-fetoprotein and α-fetoprotein-L3 were caused to react with lectin was measured. Based on this value, the reaction value ([absorbance at 450 nm of a well for which glycoprotein was solid-phased to the plate and reacted]−[absorbance at 450 nm of a well for which glycoprotein was not solid-phased to the plate and reacted]) was calculated. Next, for each lectin, the interaction was calculated. Next, the calculation result of the reaction values is shown in Table 10 and FIG. 24 to FIG. 28.

TABLE 10

|  | Example 1 PTL | Example 2 SRL | Comparison Example 1 AAL | Comparison Example 2 AOL | Comparison Example 3 LCA |
| --- | --- | --- | --- | --- | --- |
| α-fetoprotein | 0.039 | 0.031 | −0.049 | 0.011 | 0.010 |
| α-fetoprotein-L3 | 1.548 | 1.625 | 0.795 | 0.898 | 0.455 |

As can be seen from Table 10, PTL of Example 1 and SRL of Example 2 can detect a change of the sugar chain of the tumor marker (α-fetoprotein-L1-type sugar chain and L3-type sugar chain) at a level equal to or higher than the detection by LCA of Comparison Example 3. Thus, PTL of Example 1 and SRL of Example 2 can be used for a diagnostic agent or a diagnostic agent kit by detecting changes of the sugar chain of the tumor marker. Furthermore, the lectin of the present invention has a high specificity possibility where a target L-fucose α1→6 sugar chain compound can be detected from among a sugar chain compound group including therein sugar chains other than an L-fucose α1→6 sugar chain in a more accurate method than other lectins.

Examples 3 and 4

Manufacture and Property Measurement of NSL and LSL (1) Manufacture of NSL

Example 3

Based on the purification process shown in FIG. 29, *Naematoloma sublateritium* lectin (NSL) was purified from *Naematoloma sublateritium*.

(Extraction)

Freeze-dried *Naematoloma sublateritium* powders (40 g) were extracted with 0.8 L of PBS at 4 degrees C. for 2 hours. This liquid was centrifuged (10,000 rpm, 20 min, 4 degrees C.). Then, the supernatant was subjected to a gauze filtration to thereby obtain the first extraction liquid. This extraction residue was re-extracted with 0.4 L of PBS at 4 degrees C. one night. After the centrifugal operation (10,000 rpm, 20 min, 4 degrees C.), the supernatant was subjected to a gauze filtration to thereby obtain the second extraction liquid. These extracts were combined to obtain *Naematoloma sublateritium* extracts.

(Ammonium Sulfate Precipitation)

Solid $(NH_4)_2SO_4$ (0.8 kg) was added to the resulting supernatant (1.5 L) to obtain 80% saturation. After standing at 4 degrees C. overnight, the precipitates were collected by centrifugation (10,000 rpm, 20 min, 4 degrees C.) and dialyzed extensively against distilled water and lyophilized, thereby collecting *Naematoloma sublateritium*-80% ammonium sulfate precipitation fraction.

(Hydrophobic Chromatography)

Figure 30:
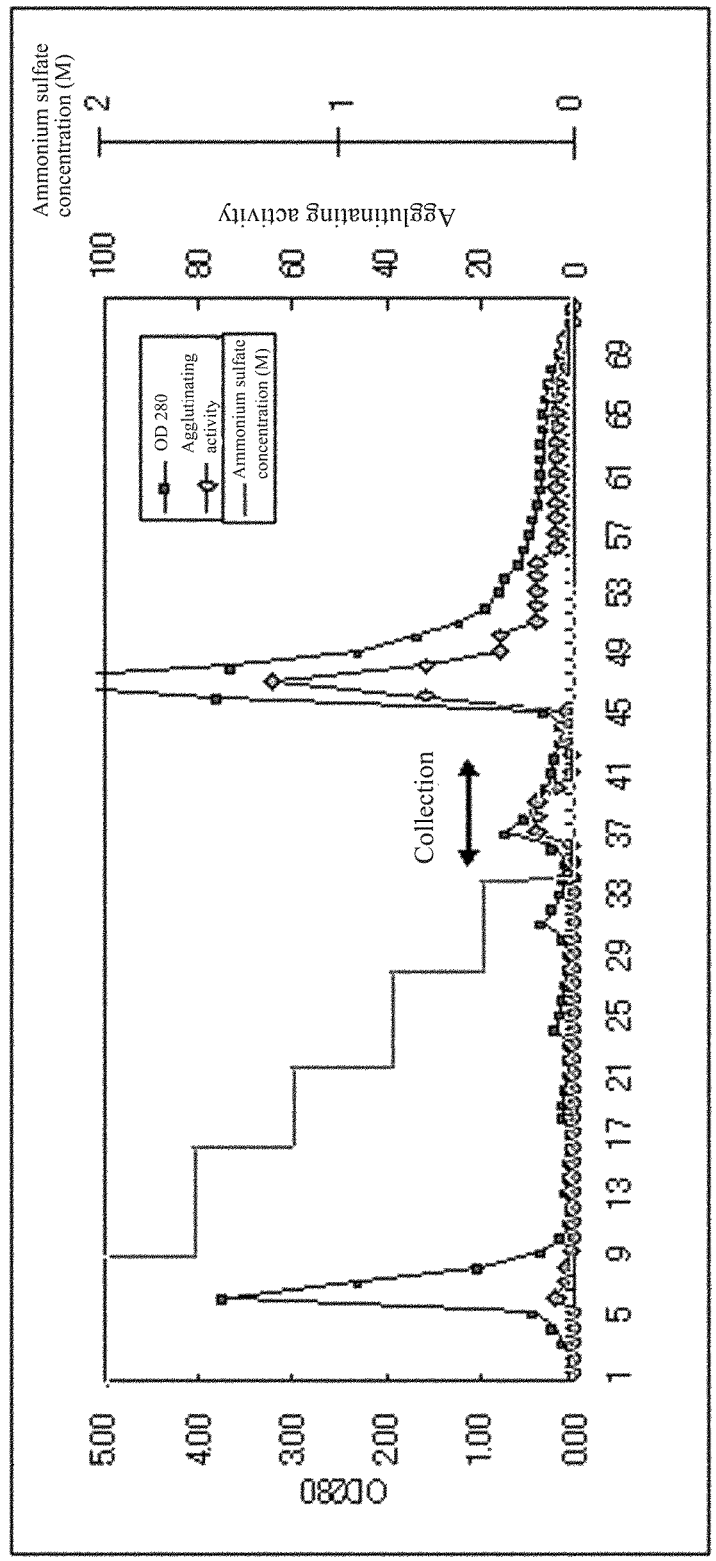
FIG. 30 is an elution diagram of hydrophobic chromatography of NSL of Example 3.

The *Naematoloma sublateritium*-80% ammonium sulfate precipitation fraction was applied to Butyl-TOYOPEARL 650M (TOSOH CORPORATION) equilibrated with 2 M of ammonium sulfate-PBS to perform hydrophobic chromatography purification. In this chromatography, distilled water elution fractions were collected, ultrafiltered, and lyophilized, thereby obtaining the *Naematoloma sublateritium* lectin crude fraction (shown by ←→ of FIG. 30).

(Reversed-Phase Chromatography)

Figure 31:
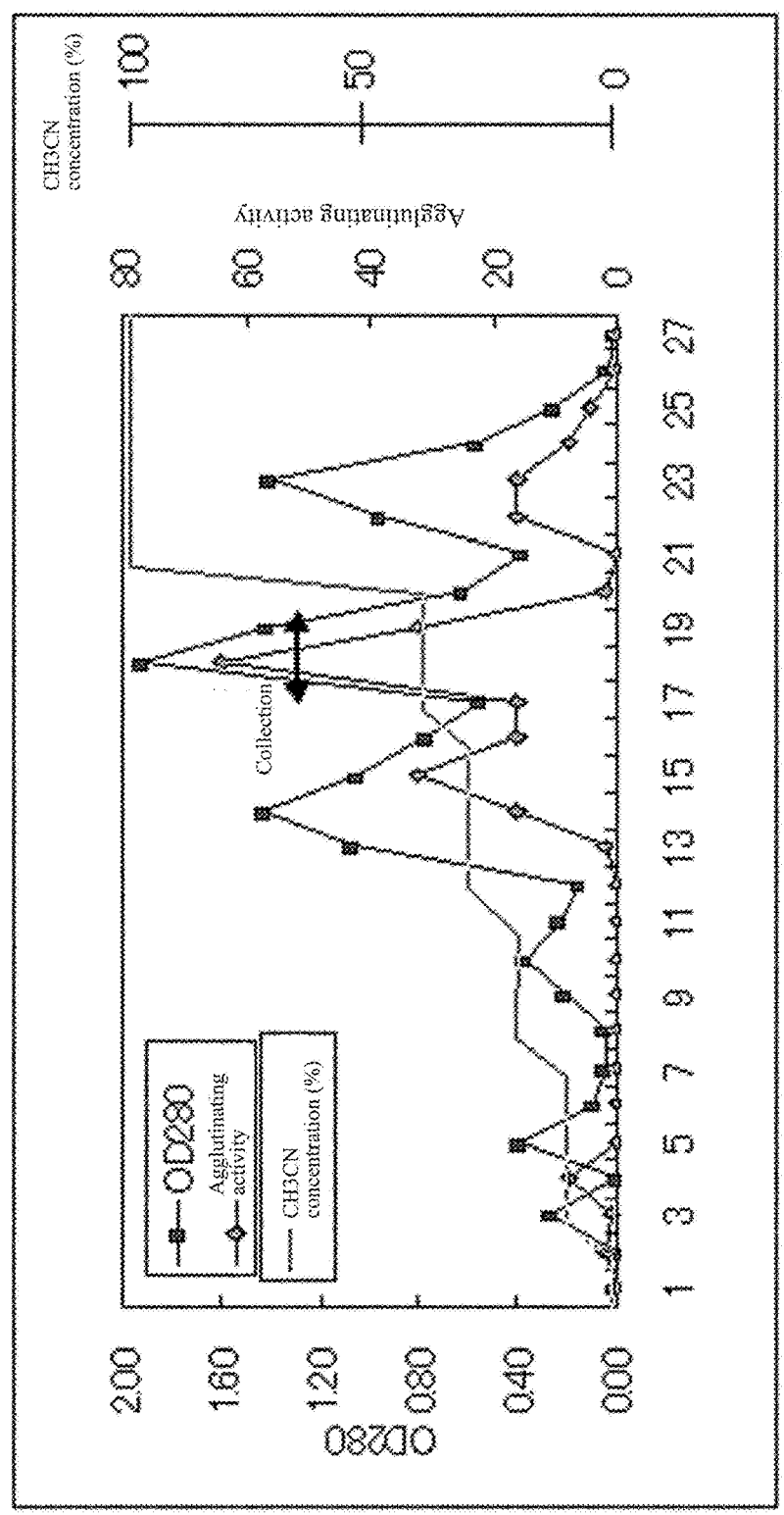
FIG. 31 is an elution diagram of reversed-phase chromatography of NSL of Example 3.

The *Naematoloma sublateritium* lectin crude fraction obtained through the above process was applied to the C8 column (Wako Pure Chemical Industries, Ltd.) equilibrated with 0.05% trifluoroacetic acid (TFA)/acetonitrile (100/0). In this chromatography, 0.05% TFA/acetonitrile (70/30) elution fraction (shown by ←→ of FIG. 31) was collected. Then, the solvent was removed by a room-temperature evaporation to thereby provide dry powders. Then, the dry powders were collected, thereby provide NSL.

Figure 32:
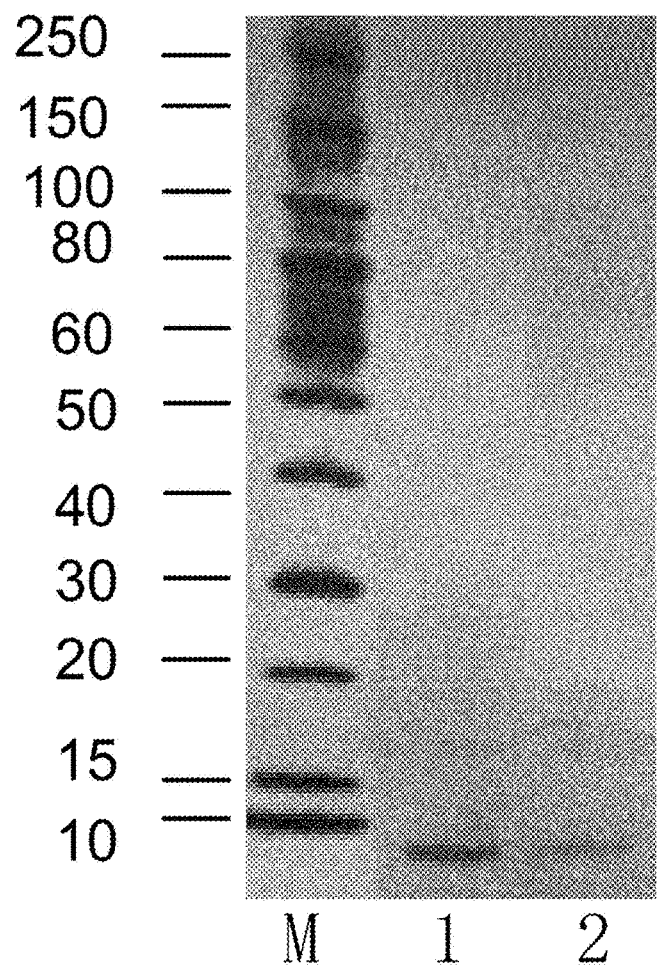
FIG. 32 illustrates the result of SDS-PAGE of NSL of Example 3 (a photograph as a substitute of a drawing).

SDS-PAGE (PhastGel, Gradient10-15) was done in a Phastsystem (GE Healthcare Bio-Sciences). The sample solution and the molecular weight marker were both used in an amount of 1 μl. The electrophoresis was performed based on the product protocol and a conventional method. FIG. 32 shows the result of SDS-PAGE of the NSL in which the lane 1 and lane 2 correspond to the followings. Lane M: molecular weight marker, lane 1: NSL, 2-mercaptoethanol(+), lane 2: NSL, 2-mercaptoethanol(−), Gel: Gradient10-15 (GE Healthcare Bioscience), and sample: 1 μl/lane, stain: silver.

On SDS-PAGE using 10-15% gel, the major component was confirmed to be NSL.

(2) Manufacture of LSL

Example 4

Based on the purification process shown in FIG. 33, *Lepista sordida* lectin (LSL) was purified from the mushroom *Lepista sordid*.
(Extraction)
Freeze-dried *Lepista sordida* powders (40 g) obtained by freeze-drying about 400 g of *Lepista sordida* were added with 0.8 L of PBS and the extraction was carried out at 4 degrees C. for 2 hours. After this liquid was centrifuged (10,000 rpm, 20 min, 4 degrees C.), the supernatant was subjected to a gauze filtration to thereby obtain the first extraction liquid. This extraction residue was re-extracted with 0.4 L of PBS at 4 degrees C. overnight. After this liquid was centrifuged (10,000 rpm, 20 min, 4 degrees C.), the supernatant was subjected to a gauze filtration to thereby obtain the second extraction liquid. These extracts were combined to thereby provide *Lepista sordida* extract.
(Ammonium Sulfate Precipitation)
Solid $(NH_4)_2SO_4$ (0.8 kg) was added to the resulting supernatant (0.5 L) to obtain 80% saturation. After standing at 4 degrees C. overnight, the precipitates were collected by centrifugation (10,000 rpm, 20 min, 4 degrees C.) and dialyzed extensively against distilled water and lyophilized, thereby collecting *Lepista sordid*-80% ammonium sulfate precipitation fraction.

Figure 34:
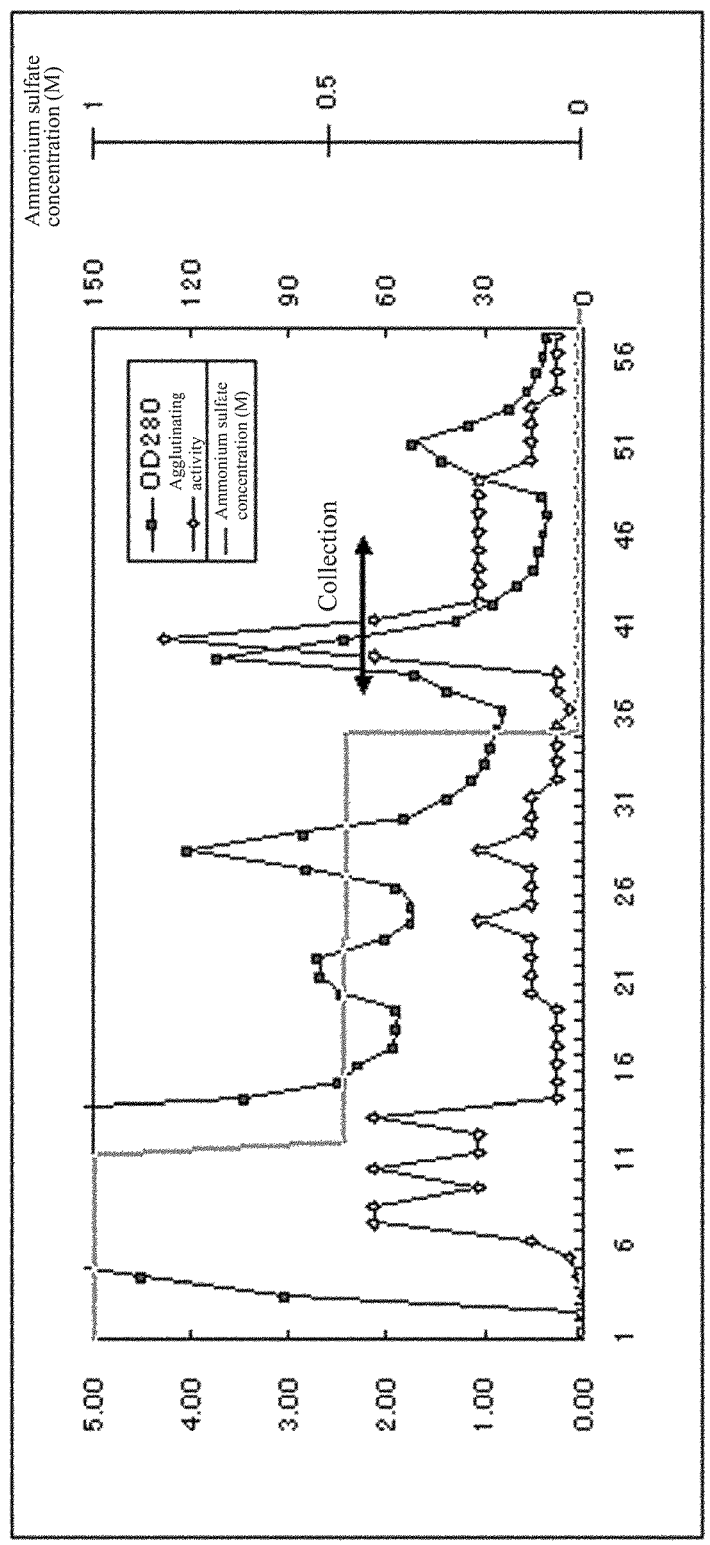
FIG. 34 is an elution diagram of hydrophobic chromatography of LSL of Example 4.
Figure 35:
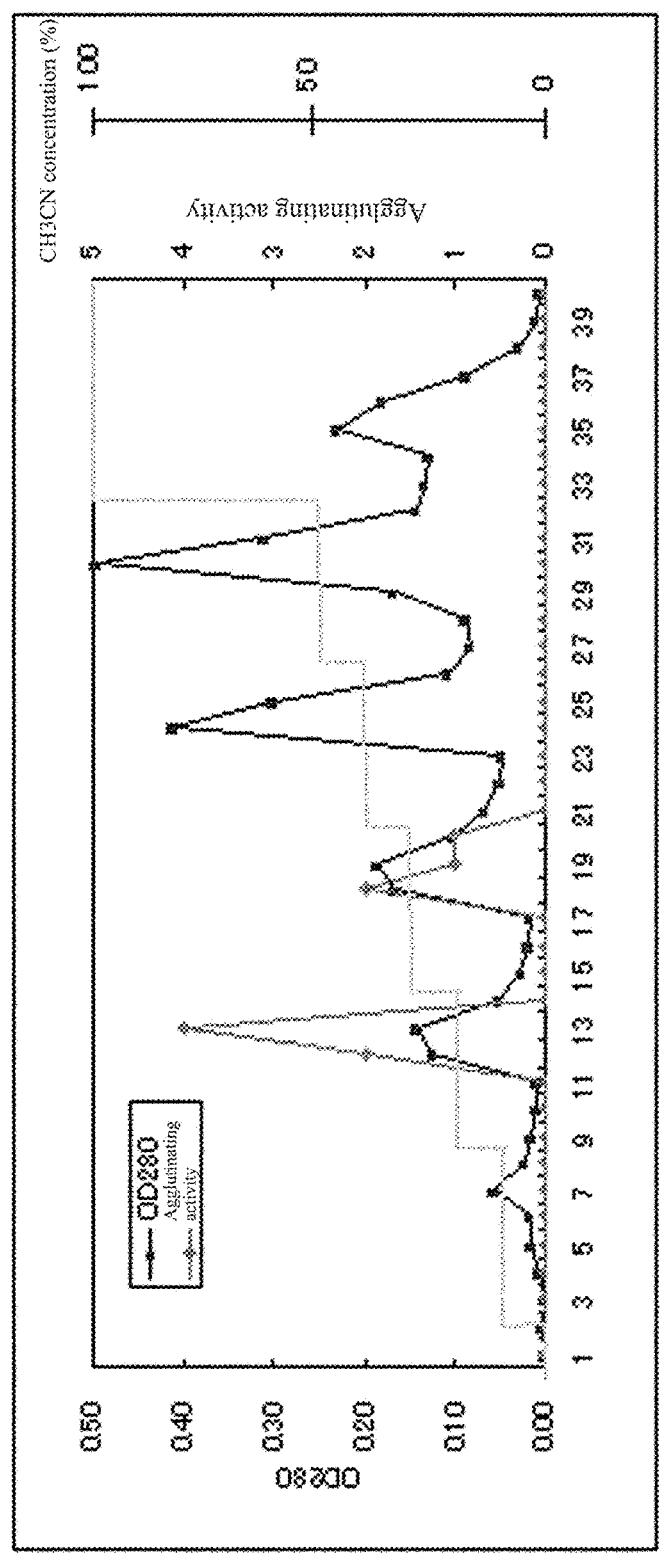
FIG. 35 is an elution diagram of reversed-phase chromatography of LSL of Example 4.

0.5 L of the extraction liquid was added with about 0.8 kg of ammonium sulfate so as to achieve an 80%-saturated ammonium sulfate concentration and the resultant liquid was agitated. Then, the complete dissolution thereof was confirmed. Then, the liquid was subjected to still-standing at 7 degrees C. one night. Then, this solution was centrifuged (10,000 rpm, 20 min, 4 degrees C.) and the precipitation was added with a small amount of distilled water. Then, the resultant solution was suspended to thereby collect a *Lepista sordid*-80% ammonium sulfate precipitation fraction. The collected *Lepista sordid*-80% ammonium sulfate precipitation fraction was subjected to a dialysis with pure water by a dialysis film (fraction of 6,000 to 8,000).
(Hydrophobic Chromatography)
The *Lepista sordid*-80% ammonium sulfate precipitation fraction was applied to Butyl-TOYOPEARL 650M (TOSOH CORPORATION) equilibrated with 2 M of ammonium sulfate-PBS to perform hydrophobic chromatography purification. In this chromatography, the PBS elution fractions were collected, ultrafiltered, and lyophilized, thereby obtaining the *Lepista sordida* lectin crude fraction (shown by ←⊖ of FIG. 34).
(Reversed-Phase Chromatography)
The *Lepista sordida* lectin crude fraction was applied to the C8 column (Wako Pure Chemical Industries, Ltd.) equilibrated with 0.05% trifluoroacetic acid (TFA)/acetonitrile (100/0). In this chromatography, 0.05% TFA/acetonitrile (70/30) elution fraction (shown by ←—→ of FIG. 35) was collected. Then, the solvent was removed by a room-temperature evaporation to provide dry powders. Then, the dry powders collected, thereby obtaining LSL.

Figure 36:
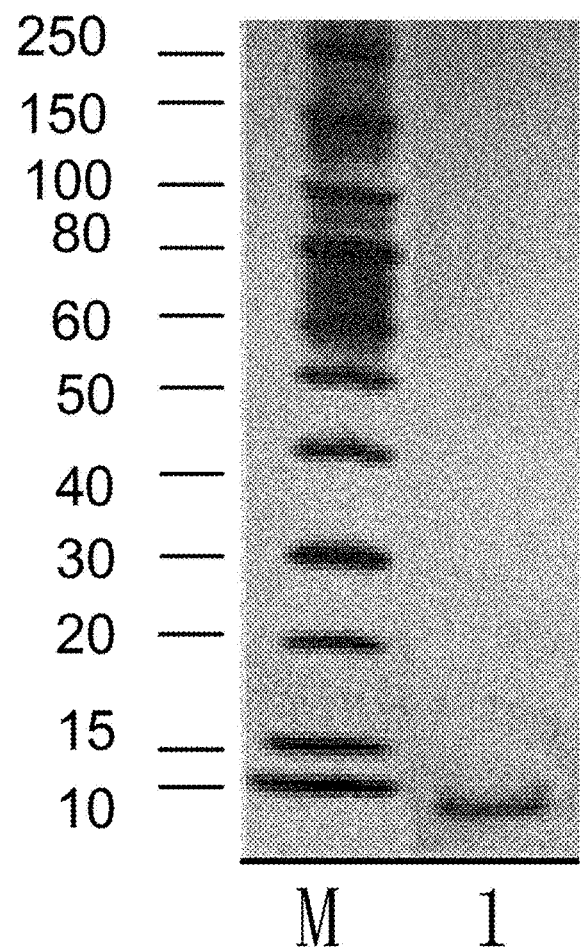
FIG. 36 illustrates the result of SDS-PAGE of LSL of Example 4 (a photograph as a substitute of a drawing).

SDS-PAGE (PhastGel, Gradient10-15) was done in a Phastsystem (GE Healthcare Bio-Sciences). The sample solution and the molecular weight marker were both used in an amount of 1 μl. The electrophoresis was performed based on the product protocol and a conventional method. FIG. 36 shows the result of SDS-PAGE of LSL in which the lane M and lane 1 correspond to the followings. Lane M: molecular weight marker, lane 1: LSL (hydrophobic chromatography, reversed phase): 2-mercaptoethanol(+), Gel: Gradient10-15 (GE Healthcare Bioscience), and sample: 1 μl/lane, stain: silver.

On SDS-PAGE using 10-15% gel, the major component was confirmed to be LSL.

(3) Properties of NSL and LSL

MALDI-TOF Mass Spectrometry Analysis

Figure 37:
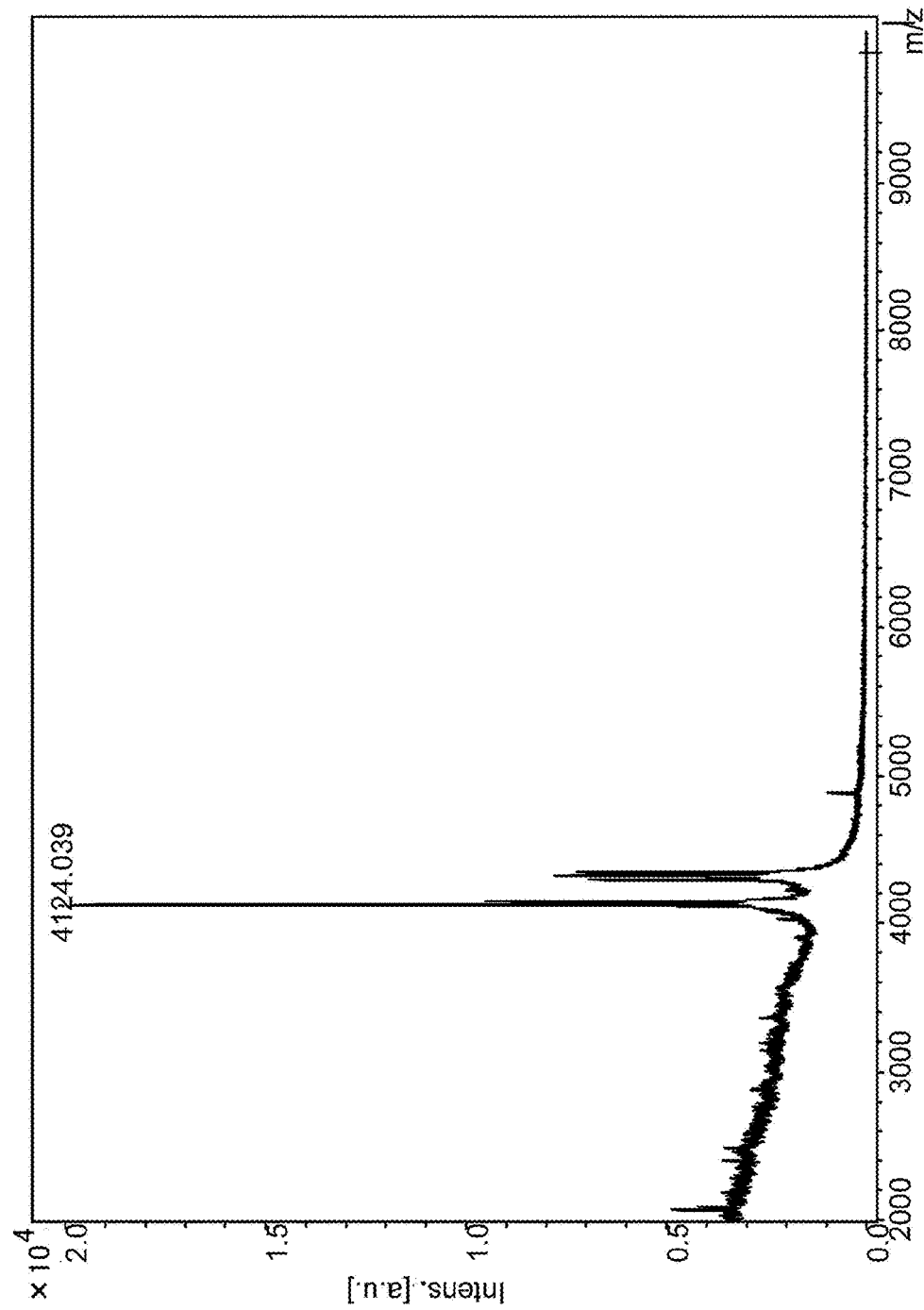
FIG. 37 illustrates the result of MS spectrum of NSL of Example 3.
Figure 38:
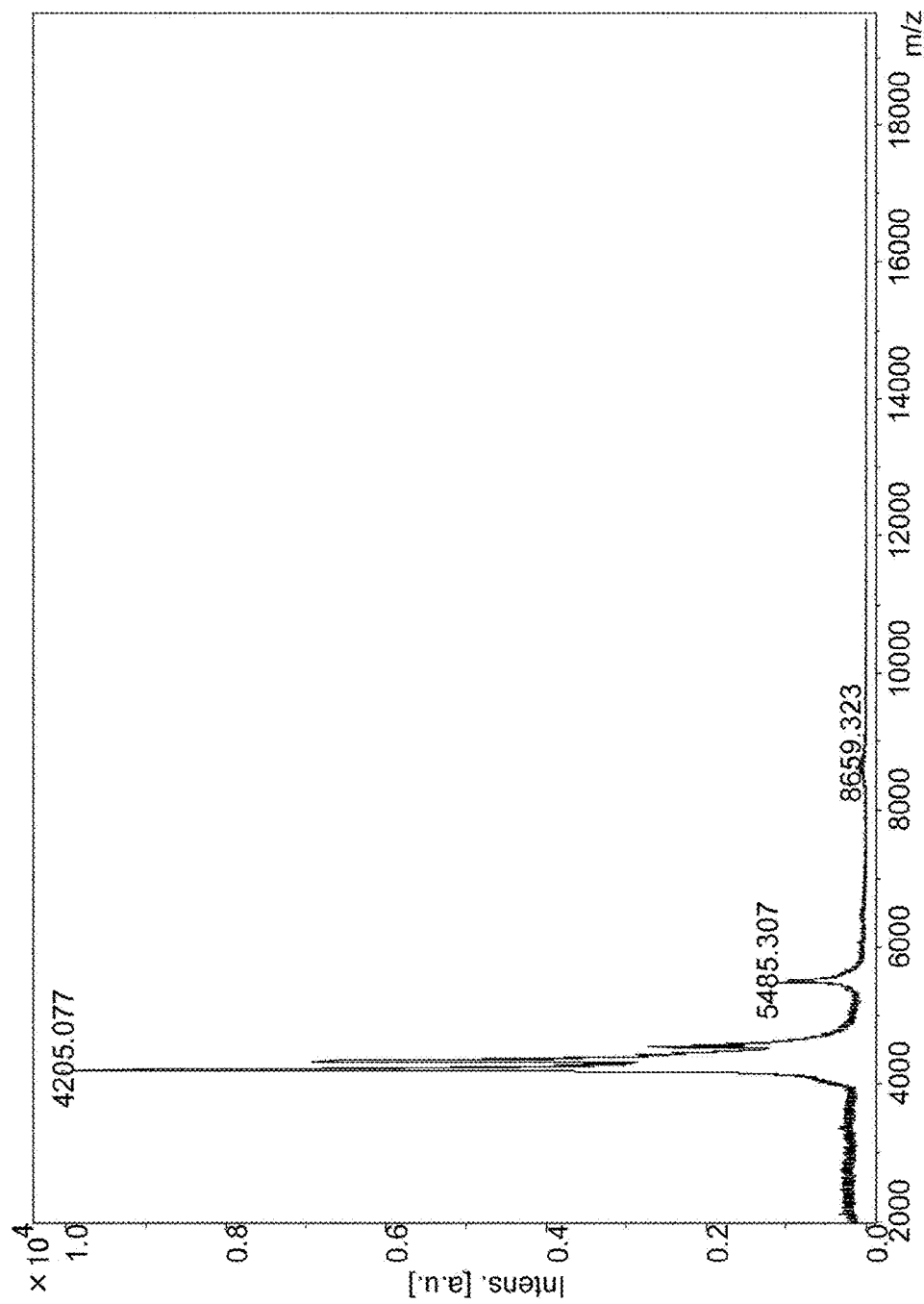
FIG. 38 illustrates the result of MS spectrum of LSL of Example 4.

NSL of Example 3 and LSL of Example in an amount of 10 μg, respectively, were separately dissolved in TA (a mixture in which 0.1% TFA and acetonitrile have a volume ratio of 2:1) by the same procedure as that of Example 1. Then, the mixture obtained by the saturated matrix dissolved in the TA and lectin TA solution at a volume ratio of 4:1 was dripped in an amount of 1.0 μl on a target plate to thereby prepare a sample. Mass spectrometry analysis apparatus of the Autoflex (Bruker Daltonics K.K.) was used to measure the molecular weights of NSL and LSL in the LP mode. The result showed that the molecular weight was about 4,500 (FIG. 37 and FIG. 38).
(Amino Acid Sequence Analysis)
The amino acid sequence of NSL of Example 3 was analyzed by Protein Peptide Sequencer PPSQ-21 System (SHIMADZU CORPORATION). NSL of Example 3 was a hybrid of the amino acid sequences shown in the sequence numbers 5 and 6. These sequences were both novel.

Similarly, the amino acid sequence of LSL of Example 4 was analyzed by the Protein Peptide Sequencer PPSQ-21 System (SHIMADZU CORPORATION). The result was shown in the sequence number 4. This sequence was also novel.

(4) Evaluation of Sugar Binding Specificity of NSL and LSL

With regard to NSL of Example 3 and LSL of Example 4, the specific binding properties to an L-fucose α1→6 sugar chain was evaluated in the same method as in Example 1. Specifically, the association constants (Ka) of the NSL and the LSL were calculated. The result is shown in Tables 11 to 13.

TABLE 11

| Sugar chain | Sugar chain No. | Example 3 NSL ($M^{-1}$) | Example 4 LSL ($M^{-1}$) |
|---|---|---|---|
| Sugar chain having α1→6 L-fucose | 015 | $3.6 \times 10^4$ | $1.9 \times 10^5$ |
| | 201 | $3.8 \times 10^4$ | $2.3 \times 10^5$ |
| | 202 | $3.9 \times 10^4$ | $2.3 \times 10^5$ |
| | 203 | $3.0 \times 10^4$ | $2.0 \times 10^5$ |
| | 401 | $5.1 \times 10^4$ | $2.2 \times 10^5$ |
| | 402 | $3.6 \times 10^4$ | $1.5 \times 10^5$ |
| | 403 | $5.2 \times 10^4$ | $2.2 \times 10^5$ |
| | 404 | $4.3 \times 10^4$ | $2.6 \times 10^5$ |
| | 405 | $5.0 \times 10^4$ | $2.2 \times 10^5$ |
| | 406 | $2.3 \times 10^4$ | $1.6 \times 10^5$ |
| | 407 | NT | NT |

TABLE 11-continued

| Sugar chain No. | Example 3 NSL ($M^{-1}$) | Example 4 LSL ($M^{-1}$) |
|---|---|---|
| 410 | $3.1 \times 10^4$ | $1.6 \times 10^5$ |
| 413 | NT | NT |
| 418 | $3.5 \times 10^4$ | $1.6 \times 10^5$ |
| 601 | NT | NT |
| 602 | $1.9 \times 10^4$ | $1.3 \times 10^5$ |

NT: Not tested

TABLE 12

| | Sugar chain No. | Example 3 NSL ($M^{-1}$) | Example 4 LSL ($M^{-1}$) |
|---|---|---|---|
| Sugar chain having L-fucose other than α1→6 L-fucose | 419 | $<1.0 \times 10^3$ | $<1.0 \times 10^3$ |
| | 420 | $<1.0 \times 10^3$ | $<1.0 \times 10^3$ |
| | 718 | $<1.0 \times 10^3$ | $<1.0 \times 10^3$ |
| | 719 | $<1.0 \times 10^3$ | $<1.0 \times 10^3$ |
| | 720 | $<1.0 \times 10^3$ | $<1.0 \times 10^3$ |
| | 721 | $<1.0 \times 10^3$ | $<1.0 \times 10^3$ |
| | 722 | $<1.0 \times 10^3$ | $<1.0 \times 10^3$ |
| | 723 | $<1.0 \times 10^3$ | $<1.0 \times 10^3$ |
| | 726 | $<1.0 \times 10^3$ | $<1.0 \times 10^3$ |
| | 727 | $<1.0 \times 10^3$ | $<1.0 \times 10^3$ |
| | 728 | $<1.0 \times 10^3$ | $<1.0 \times 10^3$ |
| | 729 | $<1.0 \times 10^3$ | $<1.0 \times 10^3$ |
| | 730 | $<1.0 \times 10^3$ | $<1.0 \times 10^3$ |
| | 731 | $<1.0 \times 10^3$ | $<1.0 \times 10^3$ |
| | 739 | $<1.0 \times 10^3$ | $<1.0 \times 10^3$ |
| | 909 | $<1.0 \times 10^3$ | $<1.0 \times 10^3$ |
| | 910 | $<1.0 \times 10^3$ | $<1.0 \times 10^3$ |
| | 931 | $<1.0 \times 10^3$ | $<1.0 \times 10^3$ |
| | 932 | $<1.0 \times 10^3$ | $<1.0 \times 10^3$ |
| | 933 | $<1.0 \times 10^3$ | $<1.0 \times 10^3$ |

TABLE 13

| | Sugar chain No. | Example 3 NSL ($M^{-1}$) | Example 4 LSL ($M^{-1}$) |
|---|---|---|---|
| Sugar chain not having L-fucose | 001 | $<1.0 \times 10^3$ | $<1.0 \times 10^3$ |
| | 002 | $<1.0 \times 10^3$ | $<1.0 \times 10^3$ |
| | 003 | $<1.0 \times 10^3$ | $<1.0 \times 10^3$ |
| | 004 | $<1.0 \times 10^3$ | $<1.0 \times 10^3$ |
| | 005 | $<1.0 \times 10^3$ | $<1.0 \times 10^3$ |
| | 006 | $<1.0 \times 10^3$ | $<1.0 \times 10^3$ |
| | 007 | $<1.0 \times 10^3$ | $<1.0 \times 10^3$ |
| | 008 | $<1.0 \times 10^3$ | $<1.0 \times 10^3$ |
| | 009 | $<1.0 \times 10^3$ | $<1.0 \times 10^3$ |
| | 010 | $<1.0 \times 10^3$ | $<1.0 \times 10^3$ |
| | 011 | $<1.0 \times 10^3$ | $<1.0 \times 10^3$ |
| | 012 | $<1.0 \times 10^3$ | $<1.0 \times 10^3$ |
| | 013 | $<1.0 \times 10^3$ | $<1.0 \times 10^3$ |
| | 014 | $<1.0 \times 10^3$ | $<1.0 \times 10^3$ |
| | 101 | $<1.0 \times 10^3$ | $<1.0 \times 10^3$ |
| | 103 | $<1.0 \times 10^3$ | $<1.0 \times 10^3$ |
| | 104 | $<1.0 \times 10^3$ | $<1.0 \times 10^3$ |
| | 105 | $<1.0 \times 10^3$ | $<1.0 \times 10^3$ |
| | 107 | $<1.0 \times 10^3$ | $<1.0 \times 10^3$ |
| | 108 | $<1.0 \times 10^3$ | $<1.0 \times 10^3$ |
| | 301 | $<1.0 \times 10^3$ | $<1.0 \times 10^3$ |
| | 304 | $<1.0 \times 10^3$ | $<1.0 \times 10^3$ |
| | 305 | $<1.0 \times 10^3$ | $<1.0 \times 10^3$ |
| | 307 | $<1.0 \times 10^3$ | $<1.0 \times 10^3$ |
| | 308 | $<1.0 \times 10^3$ | $<1.0 \times 10^3$ |
| | 313 | $<1.0 \times 10^3$ | $<1.0 \times 10^3$ |
| | 314 | $<1.0 \times 10^3$ | $<1.0 \times 10^3$ |
| | 323 | $<1.0 \times 10^3$ | $<1.0 \times 10^3$ |
| | 501 | $<1.0 \times 10^3$ | $<1.0 \times 10^3$ |
| | 502 | $<1.0 \times 10^3$ | $<1.0 \times 10^3$ |
| | 503 | $<1.0 \times 10^3$ | $<1.0 \times 10^3$ |
| | 504 | $<1.0 \times 10^3$ | $<1.0 \times 10^3$ |
| | 701 | $<1.0 \times 10^3$ | $<1.0 \times 10^3$ |
| | 702 | $<1.0 \times 10^3$ | $<1.0 \times 10^3$ |
| | 703 | $<1.0 \times 10^3$ | $<1.0 \times 10^3$ |
| | 704 | $<1.0 \times 10^3$ | $<1.0 \times 10^3$ |
| | 705 | $<1.0 \times 10^3$ | $<1.0 \times 10^3$ |
| | 706 | $<1.0 \times 10^3$ | $<1.0 \times 10^3$ |
| | 707 | $<1.0 \times 10^3$ | $<1.0 \times 10^3$ |
| | 708 | $<1.0 \times 10^3$ | $<1.0 \times 10^3$ |
| | 709 | $<1.0 \times 10^3$ | $<1.0 \times 10^3$ |
| | 710 | $<1.0 \times 10^3$ | $<1.0 \times 10^3$ |
| | 711 | $<1.0 \times 10^3$ | $<1.0 \times 10^3$ |
| | 712 | $<1.0 \times 10^3$ | $<1.0 \times 10^3$ |
| | 713 | $<1.0 \times 10^3$ | $<1.0 \times 10^3$ |
| | 715 | $<1.0 \times 10^3$ | $<1.0 \times 10^3$ |
| | 716 | $<1.0 \times 10^3$ | $<1.0 \times 10^3$ |
| | 717 | $<1.0 \times 10^3$ | $<1.0 \times 10^3$ |
| | 724 | $<1.0 \times 10^3$ | $<1.0 \times 10^3$ |
| | 725 | $<1.0 \times 10^3$ | $<1.0 \times 10^3$ |
| | 728 | $<1.0 \times 10^3$ | $<1.0 \times 10^3$ |
| | 732 | $<1.0 \times 10^3$ | $<1.0 \times 10^3$ |
| | 733 | $<1.0 \times 10^3$ | $<1.0 \times 10^3$ |
| | 734 | $<1.0 \times 10^3$ | $<1.0 \times 10^3$ |
| | 735 | $<1.0 \times 10^3$ | $<1.0 \times 10^3$ |
| | 736 | $<1.0 \times 10^3$ | $<1.0 \times 10^3$ |
| | 737 | $<1.0 \times 10^3$ | $<1.0 \times 10^3$ |
| | 738 | $<1.0 \times 10^3$ | $<1.0 \times 10^3$ |
| | 901 | $<1.0 \times 10^3$ | $<1.0 \times 10^3$ |
| | 902 | $<1.0 \times 10^3$ | $<1.0 \times 10^3$ |
| | 903 | $<1.0 \times 10^3$ | $<1.0 \times 10^3$ |
| | 905 | $<1.0 \times 10^3$ | $<1.0 \times 10^3$ |
| | 907 | $<1.0 \times 10^3$ | $<1.0 \times 10^3$ |

In the case of NSL of Example 3 and LSL of Example 4, only an L-fucose α1→6 sugar chain was detected and a non-L-fucose α1→6 sugar chain and a sugar chain not having L-fucose were not detected at all. Furthermore, NSL of Example 3 and LSL of Example 4 were also strongly bound to tri- and tetra-antenna of an L-fucose α1→6 sugar chain. Furthermore, even when sialic acid was added thereto, the association constant to an L-fucose α1→6 sugar chain was not lowered.

Finally, Table 14 showed the calculation result of homology between the proteins or peptides shown in the sequence numbers 2 to 6. As can be seen from this result, an L-fucose α1→6 specific lectin may be obtained when at least 37% homology is obtained to the amino acid sequence shown in any of the sequences 2 to 6.

TABLE 14

| | Sequence 2 | Sequence 3 | Sequence 4 | Sequence 5 | Sequence 6 |
|---|---|---|---|---|---|
| Sequence 2 | 100% | 61 to 74% | 52 to 73% | 69 to 79% | 65 to 70% |
| Sequence 3 | — | 100% | 46 to 64% | 58 to 72% | 43 to 64% |
| Sequence 4 | — | — | 100% | 46 to 64% | 37 to 55% |
| Sequence 5 | — | — | — | 100% | 87 to 92% |
| Sequence 6 | — | — | — | — | 100% |

What is claimed is:

1. An L-fucose α1→6 specific lectin that:
   (1) is extracted from basidiomycete or ascomycete,
   (2) has a molecular weight by sodium dodecyl sulfate-polyacrylamide gel electrophoresis (SDS-PAGE) of 4,000 to 40,000,
   (3) has an affinity to an L-fucose α1→6 sugar chain, the affinity being represented by an association constant of $1.0 \times 10^4 M^{-1}$ or more (at 25 degrees C.), and
   (4) has an association constant of $1.0 \times 10^3 M^{-1}$ or less (at 25 degrees C.) for a high mannose sugar chain and/or a glycolipid not including the fucose α1→6 sugar chain.

2. The L-fucose α1→6 specific lectin according to claim 1, wherein the L-fucose α1→6 sugar chain has sialic acid at the nonreducing terminus.

3. The L-fucose α1→6 specific lectin according to claim 1, wherein the L-fucose α1→6 specific lectin (5) has an affinity to L-fucose α1→6 mono-, di-, tri-, tetra-antennary N-glycan(s), the affinity being represented by an association constant of $1.0 \times 10^4 M^{-1}$ or more (at 25 degrees C.).

4. The L-fucose α1→6 specific lectin according to claim 1, wherein the basidiomycete belongs to Strophariaceae, Tricholomataceae, Amanitaceae, or Polyporaceae.

5. The L-fucose α1→6 specific lectin according to claim 1, wherein the basidiomycete is *Pholiota terrestris, Pholiota squarrosa, Pholiota adiposa, Stropharia rugosoannulata, Naematoloma sublateritium, Lepista sordida*, or *Amanita muscaria*.

6. The L-fucose α1→6 specific lectin according to claim 1, wherein the L-fucose α1→6 specific lectin further (6) includes an amino acid sequence shown in SEQ ID No. 1.

7. An L-fucose α1→6 specific lectin that is
protein or peptide consisting of an amino acid sequence shown in any of SEQ ID Nos. 2 to 6.

8. A method of manufacturing an L-fucose α1→6 specific lectin, comprising the steps of:
  subjecting an aqueous solvent extract of basidiomycete and/or ascomycete to any of following chromatography:
    (i) hydrophobic chromatography and reversed-phase chromatography,
    (ii) affinity chromatography, and
    (iii) ion-exchange chromatography and gel filtration; and
  obtaining lectin having:
    (vi) a molecular weight by SDS-PAGE of 4,000 to 40,000,
    (v) an affinity represented by an association constant to an L-fucose α1→6 sugar chain of $1.0 \times 10^4 M^{-1}$ or more, and
    (vi) an affinity represented by an association constant of $1.0 \times 10^3 M^{-1}$ or less (at 25 degrees C.) for a high mannose sugar chain and/or a glycolipid which does not contain a fucose α1→6 sugar chain.

9. The method of manufacturing the L-fucose α1→6 specific lectin according to claim 8, wherein the basidiomycete is selected from at least one of Strophariaceae, Tricholomataceae, Amanitaceae, and Polyporaceae.

10. The method of manufacturing the L-fucose α1→6 specific lectin according to claim 8, wherein the basidiomycete is at least one selected from *Pholiota terrestris, Pholiota squarrosa, Pholiota adiposa, Stropharia rugosoannulata, Naematoloma sublateritium, Lepista sordida*, and *Amanita muscaria*.

11. The method of manufacturing the L-fucose α1→6 specific lectin according to claim 8, wherein carpophores (Fruiting bodies) of the basidiomycete and/or ascomycete are used.

12. A method of detecting an L-fucose α1→6 sugar chain, comprising a step of causing a sugar chain to act on the L-fucose α1→6 specific lectin according to claim 1.

13. The method of detecting an L-fucose α1→6 sugar chain according to claim 12, wherein the sugar chain is a tumor marker.

14. A method of fractionating an L-fucose α1→6 sugar chain, comprising a step of causing a sugar chain to act on the L-fucose α1→6 specific lectin according to claim 1.

15. The method of fractionating an L-fucose α1→6 sugar chain according to claim 14, wherein the sugar chain is bound to an antibody.

16. A diagnostic agent or diagnostic agent kit for detecting an L-fucose α1→6 sugar chain, wherein the diagnostic agent includes the L-fucose α1→6 specific lectin according to claim 1 as an active ingredient.

* * * * *